US006808877B2

(12) United States Patent
Wang et al.

(10) Patent No.: US 6,808,877 B2
(45) Date of Patent: Oct. 26, 2004

(54) LIGANDS FOR FPR CLASS RECEPTORS THAT INDUCE A HOST IMMUNE RESPONSE TO A PATHOGEN OR INHIBIT HIV INFECTION

(75) Inventors: Ji-Ming Wang, Frederick, MD (US); Yingying Le, Frederick, MD (US); WangHua Gong, Frederick, MD (US); Bao Qun Li, Frederick, MD (US); Thomas Rogers, North Wales, PA (US); Philip Murphy, Rockville, MD (US); Joost J. Oppenheim, Bethesda, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 10/199,228

(22) Filed: Jul. 17, 2002

(65) Prior Publication Data

US 2003/0147883 A1 Aug. 7, 2003

Related U.S. Application Data

(63) Continuation of application No. PCT/US00/02842, filed on Feb. 4, 2000.

(51) Int. Cl.[7] .................. C12Q 1/70; G01N 33/53; C12N 5/06; A61K 39/00; A61K 39/12
(52) U.S. Cl. .................. 435/5; 435/7.24; 435/329; 424/184.1; 424/204.1; 424/208.1
(58) Field of Search ............... 435/5, 724, 339; 424/184.1, 204.1, 208.1

(56) References Cited

PUBLICATIONS

Bae, Y. S., et al. (1999) Trp–Lys–Tyr–Met–Val–D–Met stimulates superoxide generation and killing of *Staphylococcus aureus* via phospholipase D activation in human monocytes. J. Leukoc. Biol. 65:241–248.

Baek, S. H., et al. (1996) Identification of the Peptides That Stimulate the Phosphoinositide Hydrolysis in Lymphocyte Cell Lines from Peptide Libraries. J. Biol. Chem. 271(14):8170–8175.

Delézay, O., et al. (1996) SPC3, a V3 Loop–Derived Synthetic Peptide Inhibitor of HIV–1 Infection, Binds to Cell Surface Glycosphingolipids. Biochem. 35:15663–15671.

(List continued on next page.)

*Primary Examiner*—Hankyel T. Park
(74) *Attorney, Agent, or Firm*—Knobbe, Martens, Olson & Bear, LLP

(57) ABSTRACT

The present invention relates to the discovery of molecules that inhibit viral infection and promote a host immune response to a pathogen. More specifically, the invention disclosed herein concerns molecules that interact with a FPR class receptor, inhibit HIV infection, and stimulate an inflammatory response in a subject. Embodiments of the invention include biotechnological tools, prophylactics, therapeutics, and methods of use of the foregoing, for the study, treatment, and prevention of HIV infection and the induction of an inflammatory response in a subject.

9 Claims, 29 Drawing Sheets

PUBLICATIONS

Figure 1A:
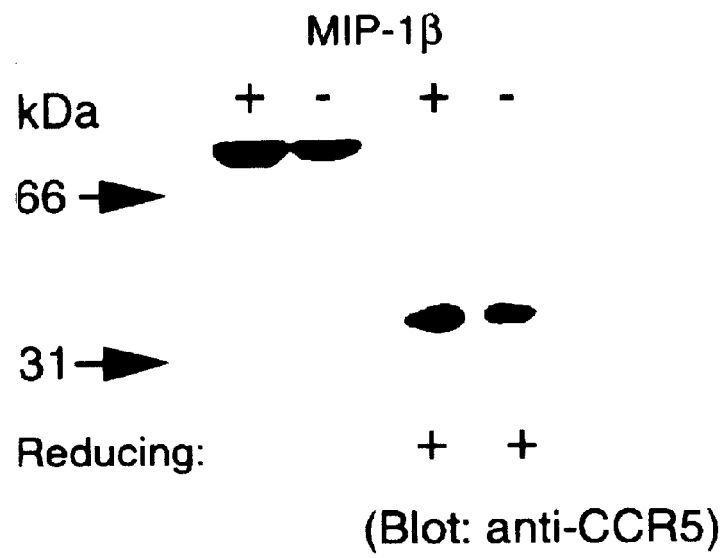

Deng, X., et al. (1999) A Synthetic Peptide Derived From Human Immunodeficiency Virus Type 1 gp120 Downregulates the Expression and Function of Chemokine Receptors CCR5 And CXCR4 in Monocytes by Activating the 7–Transmembrane G–Protein–Coupled Receptor FPRL1/LXA4R. Blood 94(4):1165–1173.

Le, Y., et al. (1999) A new insight into the role of "old" chemotactic peptide receptors FPR and FPRL1: down–regulation of chemokine receptors CCR5 and CXCR4. Trends in Exp. Clin. Med. 9:299–311. (Also Database Medline XP002154094 as referenced in IPER).

Le, Y., et al. (1999) Utilization of Two Seven–Transmembrane, G Protein–Coupled Receptors, Formyl Peptide Receptor–Like 1 and Formyl Peptide Receptor, by the Synthetic Hexapeptide WKYMVm for Human Phagocyte Activation. J. Immunol. 163(12):6777–6784.

Seo, J. K., et al. (1997) A Peptide with Unique Receptor Specificity. Stimulation of Phosphoinositide Hydrolysis and Induction of Superoxide Generation in Human Neutrophils. J. Immunol. 158:1895–1901.

Seo, J. K., et al. (1998) Distribution of the Receptor for a Novel Peptide Stimulating Phosphoinositide Hydrolysis in Human Leukocytes. Clin. Biochem. 31(3):137–141.

Shen, W., et al. (2000) Down–regulation of the chemokine receptor CCR5 by activation of chemotactic formyl peptide receptor in human monocytes. Blood 96:2887–2894.

Su, S. B., et al. (1999) T21/DP107, A Synthetic Leucine Zipper–Like Domain of the HIV–1 Envelope gp41, Attracts and Activates Human Phagocytes by Using G–Protein–Coupled Formyl Peptide Receptors, J. Immunol. 162:5924–5930.

Verrier, F., et al. (1999) Role of HIV Type 1 Glycoprotein 120 V3 Loop in Determining Coreceptor Usage. Aids Research and Human Retroviruses 15(8):731–743.

WO/00/66622, Nov. 9, 2000, filed as U.S. pat. appl No. 10/005,305.

WO 01/57074, Aug. 9, 2001, filed as U.S. pat. appl. No. 10/199,228.

WO 01/21188, Mar. 29, 2001, filed as U.S. pat. appl. No. 10/099,782.

Deng et al., A Synthetic Peptide Derived From Human Immunodeficiency: Virus Type 1 gp120 Downregulates the Expression and Function of Chemokine Receptors CCR5 and CXDR4 in Monocytes by Activating the 7–Transmembrane G–Protein–Coupled Receptor FPRL/LXA4R, Blood, 94: 1165–1173 (Aug 1999).

Le et al., Utilization of two Seven–Transmembrane, G. Protein–Coupled Receptors, Formyl Peptide Receptor–Like 1 and Formyl Peptide Receptor, by the Synthetic Hexapeptide WKYMVm for Human Phagocyte Activation, J of Immunology, 163:6777–6784 (Dec 1999).

Le et al., A new insight into the role of "old" chemotactic peptide receptors FPR and FPRL1: down–regulation of chemokine receptors CCR5 and CXCR4, Trends in Experimental and Clinical Medicine, 9:299–311 (Oct–Dec 1999).

Li et al., The synthetic peptide WKYMVm attenuates the function of the chemokine receptors CCR5 and CXCR4 through activation of formyl peptide receptor–like 1, Blood, 97: 2941–2947 (May 2001).

Shen et al., Down–regulation of the chemokine receptor CCR5 by activation of chemotactic formyl peptide receptor in human monocytes, Blood, 96: 2887–2894 (Oct. 2000).

Shen et al., Activation of the Chemotactic Peptide Receptor FPRL1 in Monocytes Phosphorylates the Chemokine Receptor CCR5 and Attenuates Cell Responses to Selected Chemokines, Biochemical and Biophysical Research Comm, 272:276–283 (May 2000).

Su et al., T20/DP178, an Ectodomain Peptide of Human Immunodeficiency Virus Type 1 gp41, Is an Activator of Human Phagocyte N–Formyl Peptide Receptor, Blood, 93: 3885–3892 (Jun. 1999).

Su et al., T21/DP107, A Synthetic Leucine Zipper–Like Domain of the HIV–1 Envelope gp41, Attracts and Activates Human Phagocytes by Using G–Protein–Coupled Formyl Peptide Receptors, J of Immunology, 162: 5924–5930 (May 1999).

Su et al., A Seven–transmembrane, G Protein–coupled Receptor, FPRL1, Mediates the Chemotactic Activity of Serum Amyloid A for Human Phagocytic Cells, J. of Experimental Med, 189: 395–402 (Jan 1999).

Monocytes

CCR5/293

Time-course (MIP-1β 1μg/ml)

(IP: anti-PS, Blot: anti-CCR5)

(Blot: anti-CCR5)

Dose-response (MIP-1β)

(IP: anti-PS, Blot: anti-CCR5)

(IP: anti-PS, Blot: anti-CCR5)

(IP: anti-PS, Blot: anti-CCR5)

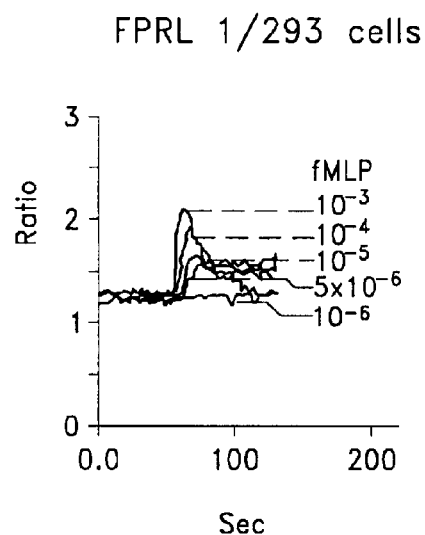
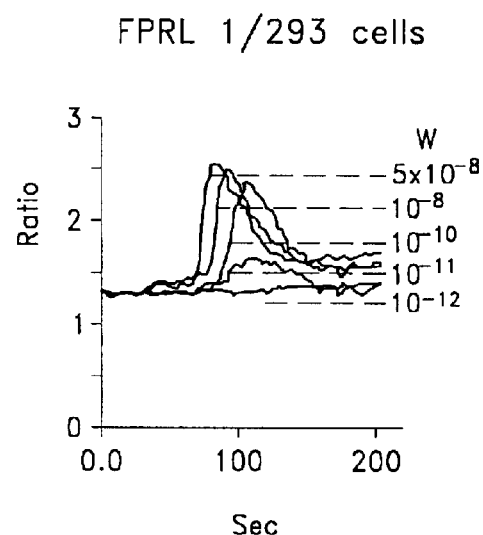
*FIG. 13E*
*FIG. 13F*
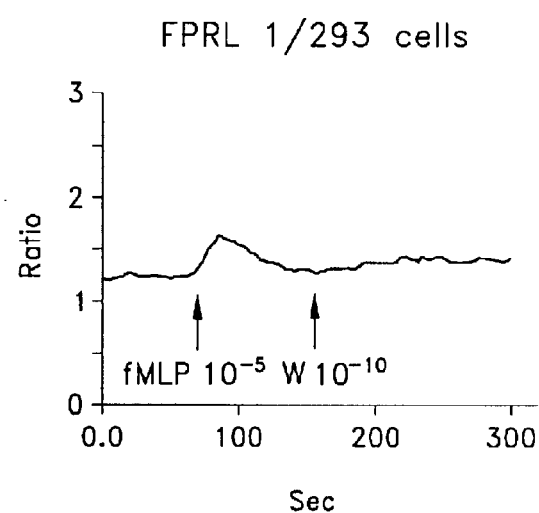
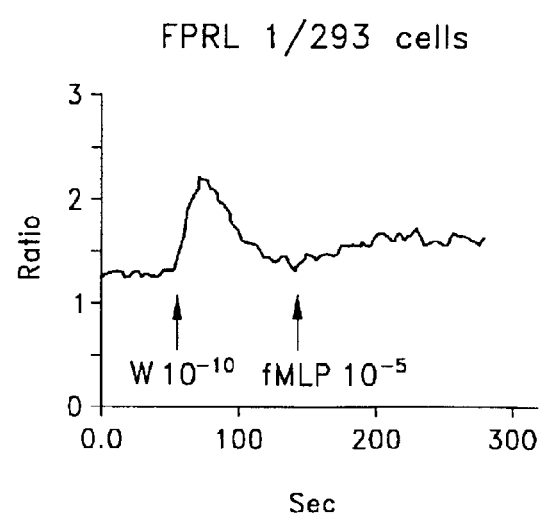
*FIG. 13G*
*FIG. 13H*

LIGANDS FOR FPR CLASS RECEPTORS THAT INDUCE A HOST IMMUNE RESPONSE TO A PATHOGEN OR INHIBIT HIV INFECTION

CROSS-REFERENCE TO RELATED APPLICATIONS

This application is a continuation of international application number PCT/US00/02842 and claims the benefit of priority of international application number PCT/US00/02842 having international filing date of Feb. 4, 2000, designating the United States of America and published in English, which is hereby expressly incorporated by reference in its entirety.

FIELD OF THE INVENTION

The present invention relates to the discovery of molecules that inhibit viral infection and promote an immune response to a pathogen. More specifically, the invention disclosed herein concerns molecules that interact with a FPR class receptor, inhibit HIV infection, and stimulate an inflammatory response in a subject.

BACKGROUND OF THE INVENTION

Human monocytes express a wide variety of seven transmembrane (STM), G-protein coupled receptors including chemokine receptors and receptors for classic chemotactic factors such as the bacterial chemotactic peptide N-formyl-methionyl-leucyl-phenylalanine (fMLP), activated complement component 5 (C5a), and leukotriene B4 (LTB4). (Murphy. *Annu Rev Immunol*, 12:593 (1994); Murphy, "The N-formyl peptide chemotactic receptors," *Chemoattractant ligands and their receptors*, CRC Press, Boca Raton, 1996:269; and Prossnitz and Ye, *Pharmacol Ther*, 74:73 (1997)). Both classical chemoattractants and chemokines bind and activate these G-protein-coupled, STM receptors, which in turn, induce signaling cascades that promote cellular calcium ($Ca^{2+}$) mobilization, phosphoinositide hydrolysis, chemotaxis, and activation of mitogen-activated protein kinase. (Schiffmann et al., *Proc. Natl. Acad. Sci. U.S.A.*, 72:1059–1062 (1975); Oppenheim et al., *Annu. Rev. Immunol.*, 9:617–648 (1991); Murphy, "The N-formyl peptide chemotactic receptors," *Chemoattractant ligands and their receptors*, CRC Press, Boca Raton, vol. 269 (1996); and Balkwill, *J. Viral Hepatitis*, 5:1–14 (1998)). Cells activated in this manner are essential participants in a host immune response to a pathogen.

The FPR class receptors are G-protein-coupled, STM receptors that bind the chemoattractant fMLP and are involved in monocyte chemotaxis and the induction of a host immune response to a pathogen. The prototype FPR class receptor, FPR, binds fMLP with high affinity and is activated by low concentrations of fMLP. The binding of FPR by fMLP induces a cascade of G protein-mediated signaling events leading to phagocytic cell adhesion, chemotaxis, release of oxygen intermediates, enhanced phagocytosis and bacterial killing, as well as MAP kinase activation and gene transcription. (Krump et al., *J Biol Chem* 272:937 (1997); Prossnitz et al., *Pharmacol Ther* 74:73 (1997); Murphy, *Annu. Rev. Immuno.* 12: 593 (1994); and Murphy, The N-formyl peptide chemotactic receptors, *Chemoattractant ligands and their receptors*. CRC Press, Boca Raton, p. 269 (1996)). Another FPR class receptor is the highly homologous variant of FPR, named FPRL1 (also referred to as FPRH2 and LXA4R). FPRL1 was originally cloned as an orphan receptor (Murphy et al., *J. Biol. Chem.*, 267:7637–7643 (1992); Ye et al., *Biochem. Biophys. Res. Commun.*, 184:582–589 (1992); Bao et al., *Genomics*, 13:437–440 (1992); Gao, J. L. and P. M. Murphy, *J. Biol. Chem.*, 268:25395–25401 (1993); and Nomura et al., *Int. Immunol.*, 5:1239–1249 (1993)) but was subsequently found to mediate $Ca^{2+}$ mobilization in response to high concentrations of fMLP. (Ye et al., *Biochem. Biophys. Res. Commun.*, 184:582–589 (1992); and Gao, J. L. and P. M. Murphy, *J. Biol. Chem.*, 268:25395–25401 (1993)).

The chemokine receptor CCR5 is another G-protein-coupled, STM receptor and is a major fusion-cofactor exploited by most primary isolates of the human immunodeficiency virus type 1 (HIV-1). (Horuk, *Immunol Today*, 20:89 (1999); Dimitrov and Broder, "HIV and Membrane Receptors," *HIV and membrane fusion: Medical Intelligence Unit*, Landes Bioscience, Austin, Tex., 1997:99; and Berger, *AIDS* 11, Suppl A:S3 (1997)). Individuals that fail to express CCR5 are largely resistant to HIV-1 infection. (Paxton, et al., *Nat Med*, 2:412 (1996); Dean, et al., *Science*, 273:1856 (1996)). Due to its prominent role in HIV-1 fusion and entry, investigators have foccussed considerable reasearch on developing molecules that interrupt the interaction between the HIV-1 envelope and CCR5. Chemokine ligands and antibodies specific for CCR5, for example, have been shown to inhibit HIV-1 entry and replication. (Cocchi et al., *Science*, 270:1811 (1995); Wu et al., *J Exp Med*, 186:373 (1997); Proudfoot et al., *J Biol Chem*, 271:2599 (1996); Arenzana-Seisdedos et al., *Nature*, 383:400 (1996); Gong et al., *J Biol Chem*, 273:4289 (1998)).

BRIEF SUMMARY OF THE INVENTION

One aspect of the invention concerns novel ligands for FPR class receptors that modulate a host immune response to a pathogen. Another aspect of the invention concerns the discovery that activated FPR class receptors promote phosphorylation and downregulation of CCR5, which, in turn, inhibits HIV infection. Several different ligands were found to interact with FPR class receptors and stimulate Ca+2 mobilization and chemotaxis in phagocytes. It was also found that the interaction of several of these ligands with the FPR class receptors resulted in the phosphorylation and downregulation of CCR5 and/or the inhibition of HIV infection.

In initial experiments, it was observed that binding of fMLP to an FPR class receptor resulted in phosphorylation and downregulation of CCR5 and the inhibition of HIV infection. Other experiments revealed that a synthetic peptide derived from the V3 region of gp120 (called "V3 peptide"), a synthetic peptide corresponding to a region in the C-terminus of the ectodomain of gp41 (called "T20/DP178" or "T20"), and serum amyloid A ("SAA") activated FPR class receptors and induced the phosphorylation of CCR5. Additionally, it was found that a synthetic hexapeptide known as the leukocyte activating peptide or "W peptide" activated an FPR class receptor, induced $Ca^{+2}$ mobilization and chemotaxis in phagocytes, and inhibited HIV-1 infection.

Embodiments of the invention include methods of identifying agents that inhibit HIV infection by interacting with an FPR class receptor. One approach involves techniques in rational drug design, whereby, compounds that resemble ligands for FPR class receptors (also referred to as "binding partners") are designed and created using computer based homology searching, protein modeling, and combinatorial chemistry. These candidate binding partners are then evaluated for the ability to phosphorylate CCR5 and/or inhibit HIV infection in "binding partner characterization assays". Agents that inhibit HIV infection are identified by their ability to phosphorylate CCR5 and/or inhibit HIV infection in the binding partner characterization assays. By another approach, random libraries of molecules are contacted to cells expressing CD4, CCR5, and an FPR class receptor and agents that inhibit HIV infection are identified by their ability to phosphorylate CCR5 and/or inhibit HIV infection. Still another approach utilizes two hybrid systems (e.g., yeast or mammalian two-hybrid systems) to identify agents that inhibit HIV infection. Many of these approaches are amenable to high throughput analysis.

Binding partners for FPR class receptors are preferably formulated into pharamceuticals and administered to subjects in need of a medicament that stimulates an immune response to a pathogen and/or treats and prevents HIV infection. Preferably, molelcules that interact with FPR class receptors are provided to human dendritic cells (DC), which express both FPR class receptors and CCR5. Further, since DCs present in human mucosal tissues are implicated as a major target cell for HIV, molecules of the invention can be delivered to the mucosal tissues (e.g., anal-vaginal mucosa) so as to reduce the risk of HIV transmission. These pharmaceuticals can be delivered by any conventional route including, but not limited to, transdermal, topical, parenteral, gastrointestinal, transbronchial, and transalveolar. A preferred application concerns the use of binding partners in a coating for medical devices.

Methods of inducing a host immune response to a pathogen and methods of inhibiting HIV infection are also embodiments. Accordingly, a method of inducing a host immune response to a pathogen involves identifying a subject in need of a compound that interacts with an FPR class receptor and providing said subject a therapeutically sufficient amount of V3 peptide or W peptide or a fragment, derivative, or modification thereof. A method of inhibiting HIV infection, according to one aspect of the invention, involves identifying a subject at risk for contracting HIV infection or a subject already afflicted with HIV infection and providing said subject a therapeutically sufficient amount of a binding partner for a FPR class receptor. Additional embodiments of the invention include a method of inducing phosphorylation of CCR5, a method inhibiting HIV fusion, and a method of treating and preventing HIV infection. These methods involve identifying a subject in need of a molecule that induces phosphorylation of CCR5 or a molecule that inhibits HIV fusion or a molecule that treats and prevents HIV infection, respectively, and administering to said subject a therapeutically sufficient amount of a binding partner for a FPR class receptor.

BRIEF DESCRIPTION OF THE DRAWINGS

FIGS. 1 (A–D) MIP-1β induces phosphorylation of CCR5.

Human monocytes (A) or CCR5 transfected human kidney embryonic 293 cells (B) were incubated in the presence or absence of MIP-1β for 1 min at 37° C. Cell lysates (20 μg) were separated by electrophoresis in the presence (reducing+) or absence of 2-mercaptoethanol and were then transferred to Immobilon P membranes. The proteins on the membrane were subsequently probed with a polyclonal anti-CCR5 antibody. Human monocytes, incubated at designated times (C) or with designated concentrations (D) of MIP-1β were lysed and 200 μg of cell lysate was immunoprecipitated with an anti-phosphoserine antibody. The immunocomplexes were subjected to SDS-PAGE followed by immunoblotting with anti-CCR5 antibody. The inset in panel (C) shows the detection by immunoblot of CCR5 in 20 μg of cell lysate prior to immunoprecipitation.

FIGS. 2 (A–D) fMLP and T20 induce phosphorylation of CCR5.

Monocytes preincubated with the designated concentrations of fMLP (A) or with $10^{-6}$ M fMLP for designated time intervals (B) were lysed and lysates (200 μg) were subjected to immunoprecipitation with an anti-phosphoserine antibody followed by immunoblotting with an anti-CCR5 antibody. Chemokine MIP-1α at 1 μg/ml (37° C., 1 min) was used as a positive control. Panel (C) shows monocyte cell lysates that were examined for serine phosphorylation of CCR5. Monocytes were preincubated with or without calphostin C (50 ng/ml, 2.5 h at 37° C.) and were stimulated with MIP-1β (1 μg/ml, 37° C., 1 min) or fMLP ($10^{-6}$ M, 37° C., 60 min). Panel (D) shows the CCR5 phosphorylation of monocytes that were treated with different concentrations of T20 peptide. MIP-1α treatment at 1 μg/ml (37° C., 1 min) was used as a positive control.

FIGS. 3 (A–C) fMLP reduces the response of CCR5 to chemokine ligands.

In panel (A), binding of $^{125}$I-MIP-1β to monocytes that were preincubated with medium or fMLP ($10^{-6}$ M, 37° C., 60 min) was examined. Unlabeled MIP-1β (1 μg/ml) and fMLP ($10^{-6}$ M) were used to compete with $^{125}$I-MIP-1β for binding. Aliquots of monocytes were preincubated with calphostin C (50 ng/ml, 2.5 h at 37° C., C+fMLP) or staurosporine (1.4 ng/ml, 60 min, 37° C., S+fMLP) prior to treatment with fMLP. The asterisk (*) indicates the significant reduction in binding of $^{125}$1-MIP-1β on cells treated with fMLP as compared to untreated cells (P<0.01). Panel (B) shows the migration of monocytes in response to MIP-1β (100 ng/ml) after incubation with fMLP ($10^{-6}$ M, 37° C.) for the designated time intervals. Cells preincubated with calphostin C (50 ng/ml, 2.5 h, 37° C.) followed by fMLP treatment were tested in parallel. Results are expressed as net number of migrated monocytes in 3 high powered field (HPF) after subtraction of spontaneous migration in response to medium (55±7 cells) (*P<0.01). In panel (C), the calcium mobilization of monocytes in response to chemokines was evaluated. Monocytes were preincubated with medium (Medium), calphostin C (50 ng/ml, 2.5 h) followed by fMLP ($10^{-6}$ M, 37° C., 60 min) (C+fMLP), or fMLP ($10^{-6}$ M, 37° C., 60 min) (fMLP). The $Ca^{2+}$ mobilization in response to fMLP ($10^{-6}$ M) or the chemokines RANTES or MIP-1α (1 μg/ml) was then measured.

FIGS. 4 (A–E) fMLP downregulates CCR5 expression.

Monocytes incubated with different reagents were stained with a FITC-conjugated anti-CCR5 monoclonal antibody (2D7) and were analyzed for the percentage of positively stained populations by flow cytometry. In panel (A), cells were incubated with medium and were then stained with FITC-conjugated mouse IgG. In panel (B) cells were incubated with medium and were then stained with FITC-anti-CCR5. In panel (C) cells were treated with MIP-1α (1 μg/ml, 15 min, 37° C.) and were then stained with FITC-anti-CCR5. In panel (D) cells were treated with fMLP ($10^{-6}$ M, 60 min, 37° C.) were then stained with FITC-anti-CCR5. In panel (E) cells were pretreated with staurosporine (1.4 ng/ml, 30 min, 37° C.) followed by fMLP ($10^{-6}$ M, 60 min, 37° C.) and were then stained with FITC-anti-CCR5.

FIGS. 5 (A–D) Activation of an FPR class receptor inhibits monocytotropic HIV-1 envelope fusion and viral infection.

In panel (A), HOS/CD4/CCR5 cells that were stably contransfected with FPR cDNA were treated with MIP-1α

(1 μg/ml, 1 min, 37° C.) or fMLP ($10^{-6}$ M, 60 min, 37° C.) and were subsequently examined for CCR5 phosphorylation by immunoprecipitation with an anti-phosphoserine antibody and immunoblotting with anti-CCR5 antibody. Panel (B): HeLa cells infected with recombinant vaccinia encoding the envelope protein from HIV-1 Bal 31 were fused with HOS/CD4/CCR5 cells with (FPR/CCR5/CD4) or without FPR (Mock/CCR5/CD4). Chemokines (10 μg/ml) or fMLP were added when env-expressing HeLa cells and target cells were mixed. Panel (C): Human monocytes cultivated for 48 h in the absence of fetal bovine serum were also fused with HeLa cells expressing the HIV-1Bal 31 env in the presence or absence of fMLP. Results are the mean (±SD) from two separate experiments. (*) Denotes significantly reduced β-galactosidase. Panel (D): Expression of HIV-1 p24 protein following HIV-1 infection of macrophages. rhM-CSF-induced peripheral blood macrophages were exposed to fMLP for 1 h followed by infection with $HIV_{JRFL}$. Four hours later, the cells were washed and placed in culture for 6 days. The supernatants were then collected for analysis of p24 by enzyme-linked immunosorbent assay. (*) denotes significantly reduced p24 production. Similar results were obtained with HOS cells transfected with CD4, CCR5, as well as, the fMLP receptor FPR.

Figure 6B:
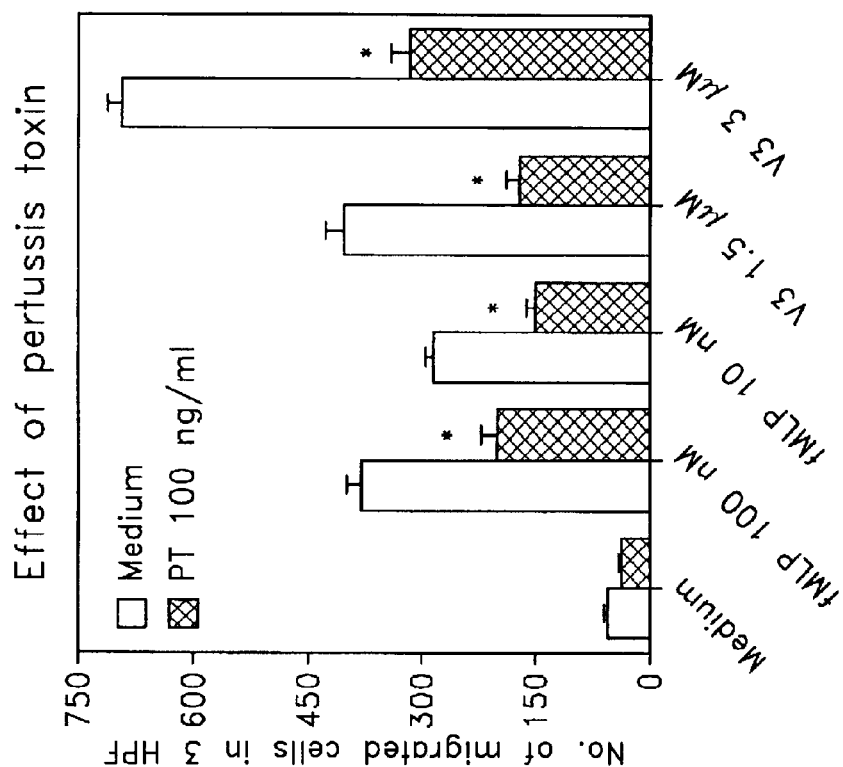
Figure 6A:
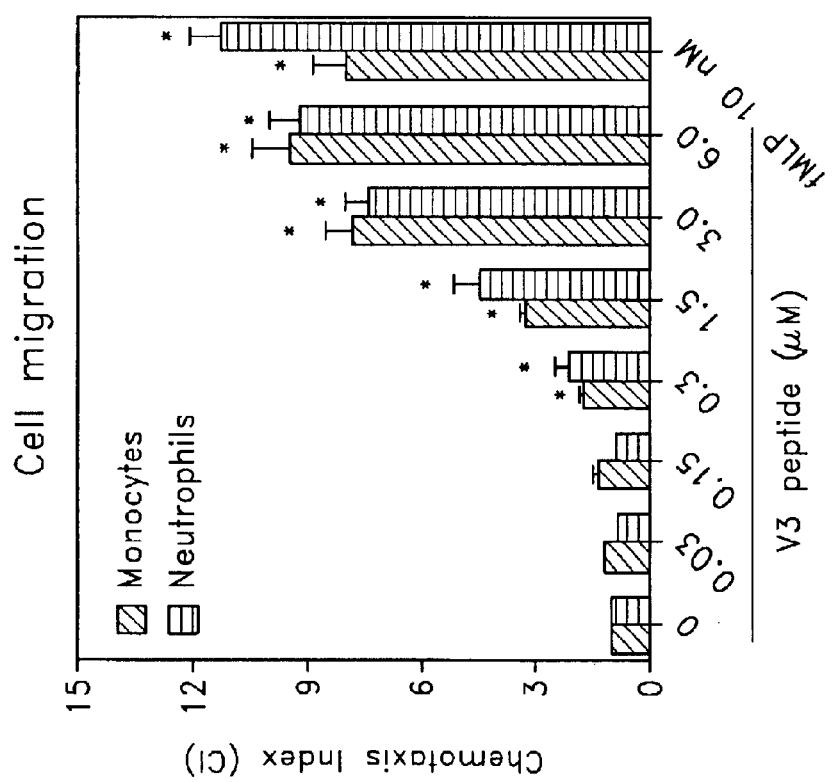

FIGS. 6 (A and B) V3 peptide induces phagocyte migration.

Panel (A) shows the fold increase (chemotaxis index) of human phagocyte migration in response to V3 peptide (over control medium. * P<0.01), as compared to spontaneous migration. Panel (B) shows that pertussis toxin (PT) inhibits V3 peptide induced cell migration. Cells preincubated with 100 ng/ml pertussis toxin (PT) at 37° C. for 30 minutes were washed and examined for migration induced by fMLP and V3 peptide. (*P<0.01, compared with migration of monocytes incubated with medium alone (Medium)).

FIGS. 7 (A–H) V3 peptide induces calcium mobilization in phagocytes.

Panels (A and B) show that $Ca^{2+}$ mobilization in monocytes and neutrophils is induced by V3 peptide. Panels (C–F) show the effect of V3 peptide (1.5 μM) on chemokine induced $Ca^{2+}$ flux in monocytes. Panels (G and H) show that V3 (1.5 μM) induced signaling in monocytes and neutrophils can be cross-desensitized with fMLP (1 μM).

Figure 8A:
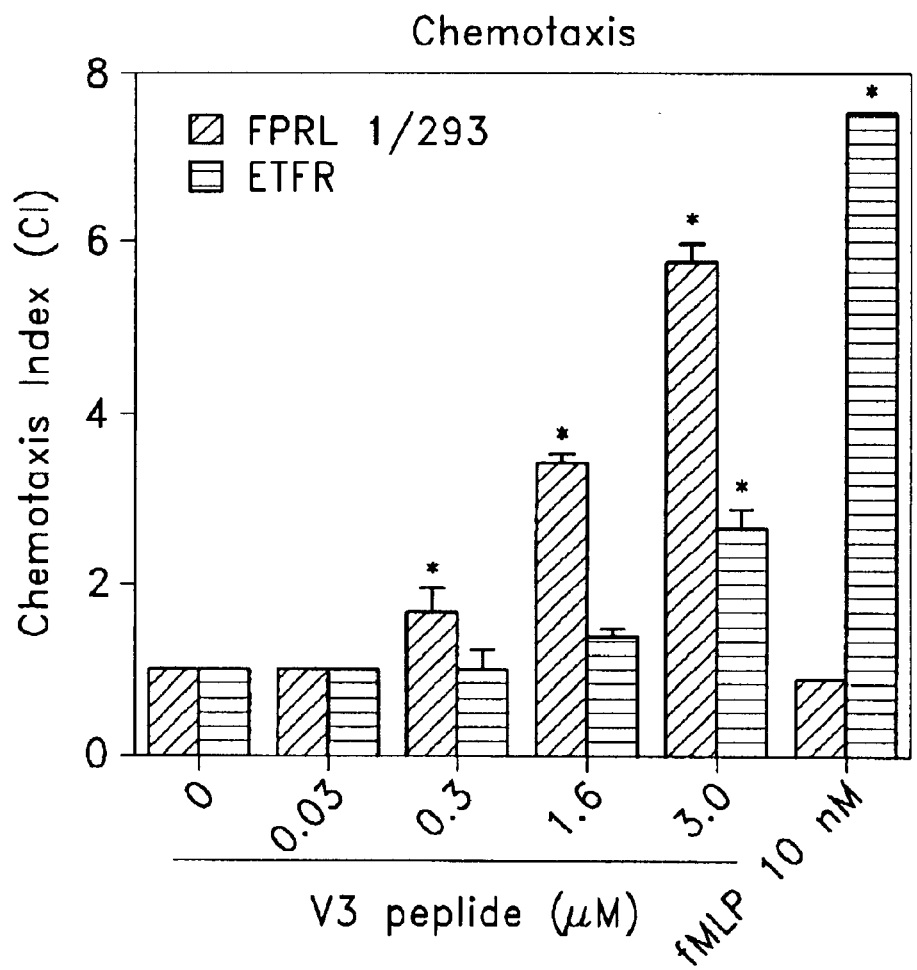
Figure 8B:
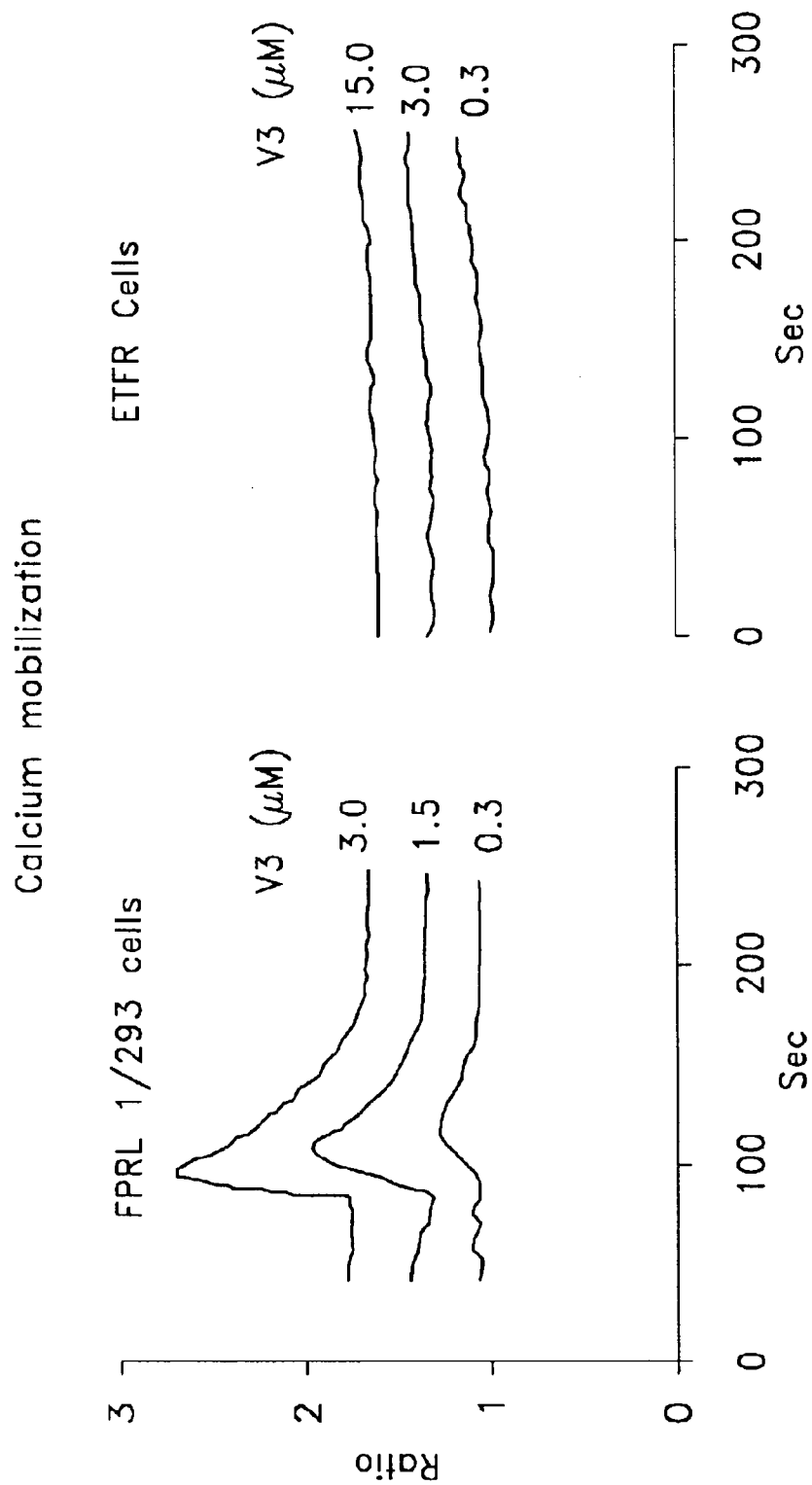

FIGS. 8 (A and B) V3 peptide induces migration and $Ca^{2+}$ flux in FPR (ETFR) and FPRL1 (FPRL1/293) expressing cells.

Panel (A) shows that FPR receptor expressing cells migrate in response to V3 peptide. fMLP was used as a control. Panel (B) shows that V3 peptide induces a $Ca^{2+}$ flux in FPRL1/293 ETFR cells.

FIGS. 9 (A–D) V3 peptide reduces cellular responses to chemokines.

Monocytes loaded with Fura-2 were preincubated with medium (Medium) or V3 peptide (V3) for 60 min at 37° C. After washing, the cells were measured for $Ca^{2+}$ mobilization in response to chemokines (10 nM) RANTES (A), SDF-1α (B) MCP-1 (C), or fMLP (10 nM) (D). In parallel experiments, cells were first treated with staurosporine (2.5 ng/ml, 30 min at 37° C.) followed by V3 peptide (1.5 μM, 37° C., 60 min, Stauro+V3), then were measured for $Ca^{2+}$ flux in response to chemokines or fMLP.

FIGS. 10 (A–H) V3 peptide and SAA induce phosphorylation of CCR5 in monocytes.

Panel (A) shows monocytes treated with MIP-1β at 100 nM for different time periods (min) at 37° C. Panel (B) shows monocytes treated with different concentrations of MIP-1β for 1 min at 37° C. Panel (C) shows an immunoblot of total cell lysates from monocytes treated with V3 peptide or MIP-1β (1 min). The anti-CCR5 antibody was used. Panel (D) shows monocytes treated with different concentrations of V3 peptide for 60 min at 37° C., cells treated with MIP-1α (100 nM) and MIP-1β (100 nM) for 1 min were used as control. Panel (E) shows monocytes treated with V3 peptide (1.5 μM) for different time points. Cells treated with MIP-1α (100 nM) for 1 min or with fMLP (1 μM) for 60 min were used as control. Panel (F) shows the effect of staurosporine (Stauro, 2.5 ng/ml, 30 min) on CCR5 phosphorylation induced by MIP-1β (100 nM, 1 min at 37° C.) or V3 peptide (1.5 μM, 60 min). Panel (G) shows monocytes treated with SAA at 10 μg/ml for different time periods (min) at 37° C. Panel (H) shows monocytes treated with different concentrations of SAA for 60 min at 37° C. The inset shows the immunoblotting of 20 μg whole monocyte lysates with anti-CCR5 antibody.

FIGS. 11 (A and B) W peptide induces phagocyte migration.

Different concentrations of W peptide were placed in the lower wells of the chemotaxis chamber, cell suspension was placed in the upper wells. The upper and lower wells were separated by polycarbonate filters. After incubation, the cells that had migrated across the filters were stained and counted. Panel (A) shows the fold increase of monocyte and neutrophil migration in response to W peptide over control medium. A chemotaxis index greater than 1.8 is statistically significant compared to spontaneous migration in the absence of chemoattractant. Panel (B) shows the inhibition of monocyte migration in response to W peptide by pretreatment of the cells with 100 ng/ml pertussis toxin (PT) or cholera toxin (CT) at 37° C. for 30 min. The peptide T21, a FPRL1 stimulating peptide domain of HIV-1 envelope gp41, was used as a control. (*P<0.01 compared to migration of cells incubated with medium alone).

FIGS. 12 (A–H) W peptide induces calcium ($Ca^{2+}$) mobilization in phagocytes

Human monocytes or neutrophils were loaded with Fura-2 and then were stimulated with various concentrations of W peptide panels (A and E). The ratio of fluorescence at 340 and 380 nm wave length was recorded and calculated using the FLWinLab program. Desensitization of W peptide induced $Ca^{2+}$ flux by fMLP in monocytes panels (B and C) or neutrophils panels (F and G) and was measured by sequentially stimulating the cells with both agonists and vice versa panels (D and H).

FIGS. 13 (A–H) W peptide induces calcium mobilization in ETFR and FPRL1/293 cells ETFR cells (upper panels) and FPRL1/293 cells (lower panels) were used to evaluate $Ca^{2+}$ flux induced by fMLP (panel (A and E)) or W peptide (panel (B and F)). Panels (C, D, G, and H) show cross-desensitization of cell signaling between W peptide and fMLP.

FIGS. 14 (A–D) W peptide induces migration of FPRL1/293 and ETFR cells in response to W peptide.

Panels (A, B and C) show the fold increase (chemotaxis index) of FRPL1/293 cell or ETFR cell migration in response to W peptide or fMLP over control medium. A CI greater than 1.8 was statistically significant compared to spontaneous cell migration in the absence of chemoattractant. Panel (D) shows the inhibition of FPRL1/293 cell migration in response to W peptide by pretreatment of the cells with 100 ng/ml pertussis toxin (PT) at 37° C. for 30 min. (*P<0.01 compared to migration of cells incubated with medium alone.)

Figure 15:
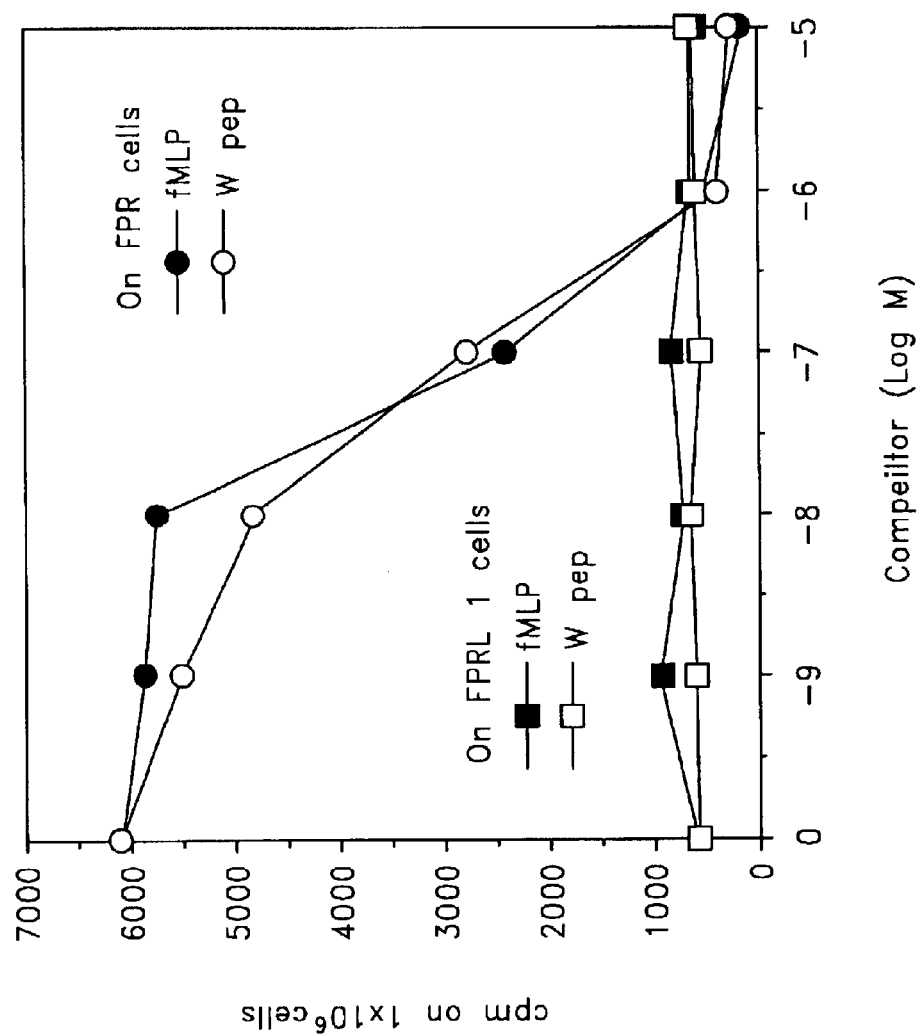

FIG. 15 W peptide can displace $^3$H-fMLP that is bound to ETFR or FPRL1/293 cells.

Aliquots of cells (2×10$^6$/200 μl) were incubated with $^3$H-fMLP (0.2 nM) in the presence of different concentrations of unlabeled fMLP or W peptide at 37° C. for 30 min. The cells were then washed with ice-cold PBS (phosphate buffered saline) and filtered onto Whatman discs. The radioactivity associated with the cells was measured with a β counter. Three experiments were performed and yielded similar results.

FIGS. 16 (A and B) W peptide inhibits HIV infection.

Hos cells expressing CD4/CCR5/FPRL1 receptors were first treated with W peptide at designated concentrations for 1 hour followed by infection with HIV-1$_{JRFL}$ for one hour. The infected cells were washed three times with medium and placed in culture. The levels of p24 were measured by ELISA at 48 hours and 72 hours post-infection. Panel (A) shows that exposure of W peptide [10$^{-5}$M] at the initial step of HIV-1 infection significantly reduced HIV-1 infectivity in FPRL1 transfectants but not mock transfected cells. Panel (B) shows that W peptide can reduce HIV-1 infectivity at concentrations as low as 10$^{-11}$M. These experiments were performed in triplicate and the data shown represents the findings of one experiment. *P is less than or equal to 0.01.

DETAILED DESCRIPTION OF THE INVENTION

The discovery of several new ligands for FPR class receptors is provided in this disclosure. Additionally, it is shown that ligands for FPR class receptors induce the phosphorylation and downregulation of CCR5 receptors and inhibit HIV infection. Preferably, molelcules that interact with FPR class receptors are provided to human dendritic cells (DC), which express both FPR class receptors and CCR5. Since DCs present in human mucosal tissues are implicated as a major target cell for HIV, molecules of the invention can be deleivered to the mucosal tissues (e.g., anal-vaginal mucosa) so as to reduce the risk of HIV transmission. These pharmaceuticals can be delivered by any conventional route including, but not limited to, transdermal, topical, parenteral, gastrointestinal, transbronchial, and transalveolar. A preferred application concerns the use of binding partners in a coating for medical devices. Embodiments of the invention also include biotechnological tools, prophylactics, therapeutics, and methods of use of the foregoing, for the study, treatment, and prevention of HIV infection and the induction of a host immune response to a pathogen.

In a first group of experiments, it was found that the classic chemotactic factor, the bacterial chemotactic peptide N-formyl-methionyl-leucylphenylalanine (fMLP), rapidly induced serine phosphorylation and downregulation of CCR5. The binding of fMLP to an FPR class receptor also resulted in significant attenuation of cell responses to CCR5 ligands and the inhibition of HIV-1 envelope glycoprotein-mediated fusion and infection of cells expressing CD4, CCR5, and FPR. In a second group of experiments, it was found that a synthetic peptide domain derived from the V3 region of the HIV-1 gp120 activates an FPR class receptor. By binding to an FPR class receptor, the V3 peptide induced phagocyte chemotaxis and serine phosphorylation of CCR5. Additionally, it was discovered that other FPR class receptor ligands including SAA and T20 induce the phosphorylation of CCR5. In another group of experiments, it was discovered that the synthetic leukocyte activating peptide or "W peptide" Trp-Lys-Tyr-Met-Val-Met (WKYMVM) (SEQ. ID. No. 1), wherein the methionine at the NH$_2$ end is a D-type amino acid, activates an FPR class receptor and, thereby, induces a calcium flux, chemotaxis, and the inhibition of HIV infection.

By enhancing or inhibiting ("modulating") the induction of an FPR class receptor, cellular responses such as signal transduction, leukocyte migration, immune system response, inflammatory response, and HIV fusion, entry, and propagation can be selectively altered. Embodiments of the invention include the use of molecules that modulate the induction of an FPR class receptor. Throughout this disclosure, the term "FPR class receptor" refers to receptors that can be activated by fMLP and have at least 80% homology to FPR and/or FPRL1. Molecules that interact with an FPR class receptor are referred to, for the purposes of this discussion, as "binding partners for an FPR class receptor" or "binding partners". Desirable binding partners of the invention interact with an FPR class receptor and, thereby, induce a host immune response to a pathogen and/or phosphorylate CCR5, downregulate the expression of CCR5, and inhibit HIV infection.

The use of several different binding partners for the induction of an immune response to a pathogen, the phosphorylation and downregulation of CCR5 receptors, and the inhibition of HIV infection are contemplated. For example, fMLP, V3 peptide, SAA, T20, and W peptide, and fragments or derivatives of these molecules can be provided to a subject in need to induce an immune response to a pathogen and/or to phosphorylate CCR5 receptors, downregulate the expression of CCR5 receptors, and inhibit HIV infection. Chemicals and peptidomimetics that resemble FPR class receptor ligands or fragments thereof and protease stable derivatives of the FPR class receptor ligands or fragments thereof can also be used to induce a host immune response to a pathogen and/or phosphorylate and downregulate expression of the CCR5 receptor and inhibit HIV infection.

Further, methods are provided that allow for the identification of additional binding partners that induce a host immune response to a pathogen and/or phosphorylate and downregulate expression of the CCR5 receptor and inhibit HIV infection. One approach involves the use of techniques in rational drug design. Accordingly, molecules that resemble identified binding partners, and fragments or derivatives of these molecules, are designed and created using computer based homology searching, protein modeling, and combinatorial chemistry. For example, a database comprising nucleic acid or protein sequences corresponding to fMLP, V3 peptide, SAA, T20, or W peptide, or fragments or derivatives of these molecules are accessed by a search program that compares the sequence to other sequences in publicly or commercially available databases so as to identify homologous ligands. By another rational approach, techniques in protein modeling (e.g., x-ray crystallography, NMR, and computer modeling) are employed to construct models of the binding partners. From these models, rational drug design can be accomplished. Additionally, protein models comprising FPR class receptors can be created, ligand binding sites can be identified, and this information can be used to rationally design more candidate binding partners.

Once the candidate binding partners are designed and created, it is preferred that they are evaluated for their ability to bind to an FPR class receptor and, thereby induce phosphorylation of CCR5, downregulation of CCR5, and inhibition of HIV infection. Approaches that evaluate the ability of a candidate binding partner or binding partner to interact with an FPR class receptor, induce phosphorylation of CCR5, induce the downregulation of CCR5, and inhibit HIV infection are collectively referred to in this disclosure as "binding partner characterization assays". Binding partner characterization assays also include approaches to evaluate the ability of a candidate binding partner or a binding partner to induce a host immune response to a pathogen (e.g., chemotaxis assays, $Ca^{+2}$ mobilization assays, and desensitization assays). Binding partner characterization assays can also include computer approaches that access the ability of a binding partner to interact with a FPR class receptor. For example, the evaluation of computer simulated ligand interactions with an FPR class receptor is, for the purposes of this disclosure, a binding characterization assay. After evaluating the candidate binding partner in the binding partner characterization assays, a binding partner that inhibits HIV infection is identified by its ability to phosphorylate CCR5, downregulate the expression of CCR5, and/or inhibit HIV infection.

In addition to conducting rational drug design, high throughput techniques can be employed to rapidly screen random libraries of molecules for binding partners that inhibit HIV infection. Such techniques exploit support-bound FPR class receptors, cell-based systems, and two-hybrid approaches. For example, multimeric supports having an FPR class receptor can be screened against molecules present in a combinatorial library so as to identify candidate binding partners. These candidate ligands can then be contacted to cells that express CD4, CCR5, and an FPR class receptor and the ability of the binding partner to phosphorylate CCR5, downregulate CCR5 expression, and/or inhibit HIV infection can be determined. Alternatively, cells that express CD4, CCR5, and an FPR class receptor can be contacted with molecules from a combinatorial library without first identifying a class of candidate binding partners by using a multimeric support having an FPR class receptor.

Further, two hybrid systems (e.g., yeast or mammalian two-hybrid approaches) can be exploited to identify binding partners. For example, a first fusion protein having a DNA binding domain (e.g., Gal-4) joined to an FPR class receptor and a second fusion protein having random peptides joined to an activating protein (e.g., VP-16) can be created. Constructs encoding these fusion proteins can be transfected into cells that have a template DNA comprised of one or more Gal-4 binding sites, a minimal promoter, and a reporter molecule (e.g, Green Fluorescent Protein or "GFP"). If the random peptide joined to the activating protein corresponds to a binding partner, then a reporter signal will be detected. By using a combination of rational drug design and high throughput techniques, several binding partners that induce phosphorylation of CCR5, downregulation of CCR5 expression, and the inhibition of HIV infection can be identified.

Therapeutic and prophylactic formulations having binding partners are also embodiments of the invention. These pharmaceuticals can be delivered by any conventional routes including, but not limited to, transdermal, parenteral, gastrointestinal, transbronchial, and transalveolar. In addition to the active ingredients mentioned above, the pharmaceutical embodiments can comprise carriers, proteins, supports, adjuvants, or components that facilitate or enhance drug delivery. A preferred application concerns the use of binding partners in a coating for medical devices including, but not limited to, gloves, vaginal instruments, and condoms.

The pharmaceutical embodiments can be employed in therapeutic protocols for induction of an immune response to a pathogen and/or the treatment and prevention of HIV infection. By one approach, a subject in need of an agent that interacts with an FPR class receptor and, thereby, induces a host immune response to a pathogen is identified and said subject is provided a therapeutically sufficient amount of V3 peptide or W peptide. By another approach a subject in need of an agent that inhibits HIV infection is identified and said subject is provided a therapeutically effective amount of a binding partner for an FPR class receptor. Similarly, an approach to treat and prevent HIV infection is provided in which a subject at risk of contracting an HIV infection or a subject already afflicted with an HIV infection is identified and is then provided a therapeutically sufficient amount of a binding partner for an FPR class receptor. In the section below, a discussion of the experiments that revealed that fMLP can induce phosphorylation of CCR5 is provided.

fMLP and T20 Induce Phosphorylation of CCR5

The effect of CCR5 ligands on the phosphorylation patterns of CCR5 in peripheral blood monocytes was initially investigated. Several studies have shown that CCR5 can be rapidly phosphorylated upon binding of its native ligands such as RANTES and MIP-1β (Oppermann et al., *J Biol Chem*, 274:8875 (1999); Olbrich et al., *J Leukoc Biol*, 65:281 (1999); Aramori et al., *EMBO J*, 16:4606 (1997); and Rodriguez-Frade et al., *J Cell Biol*, 144:755 (1999)). These studies, however, were performed in cell lines transfected to express CCR5, not native cells in which the signaling molecules coupled to CCR5 can differ.

Figure 1B:
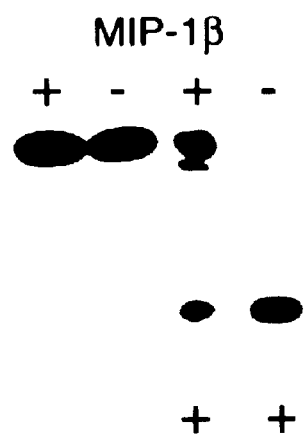
Figure 1C:
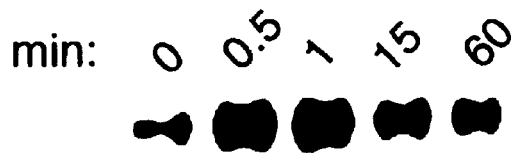
Figure 1C:
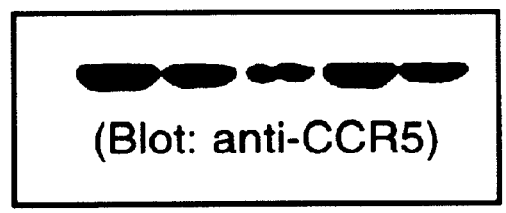
Figure 1D:
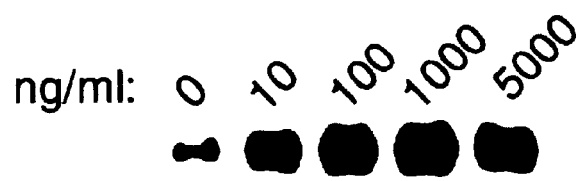

A polyclonal anti-CCR5 antibody was tested for its ability to detect CCR5 in lysates prepared from monocytes and CCR5-transfected HEK 293 cells (CCR5/293). CCR5 was detected by immunoblotting as a single protein species at about 75 kDa under non-reducing conditions, and a 40 kDa species under reducing conditions in both monocytes (FIG. 1A) and CCR5/293 cells (FIG. 1B). These results established that CCR5 in monocytes exists in the form of homodimers. In addition, stimulation of CCR5/293 cells, but not monocytes, with specific chemokines further promoted the dimerization of CCR5, which was detectable even under reducing conditions (FIG. 1B). The phosphorylation of CCR5 in monocytes was next examined by using immunoprecipitation with an anti-phosphoserine antibody followed by immunoblotting with anti-CCR5 antibody. CCR5 phosphorylation has been reported to occur exclusively on serine residues at the C-terminus of the receptor. (Dean, et al., *Science*, 273:1856 (1996)). As shown in FIGS. 1C and D, although in resting moncocytes, a low level of phosphorylation of CCR5 could be consistently observed, there was a rapid (within 1 min, FIG. 1C) and ligand concentration-dependent (FIG. 1D) increase in CCR5 phosphorylation upon cell stimulation with CCR5 agonists.

Figure 2A:
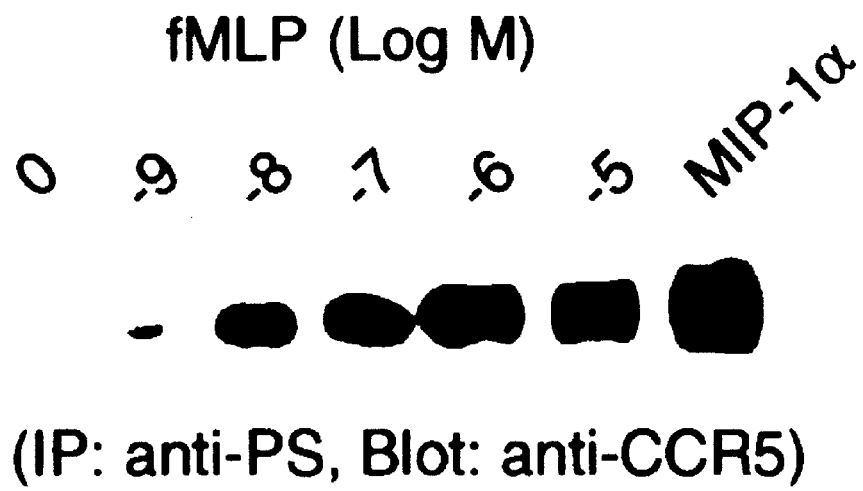
Figure 2B:
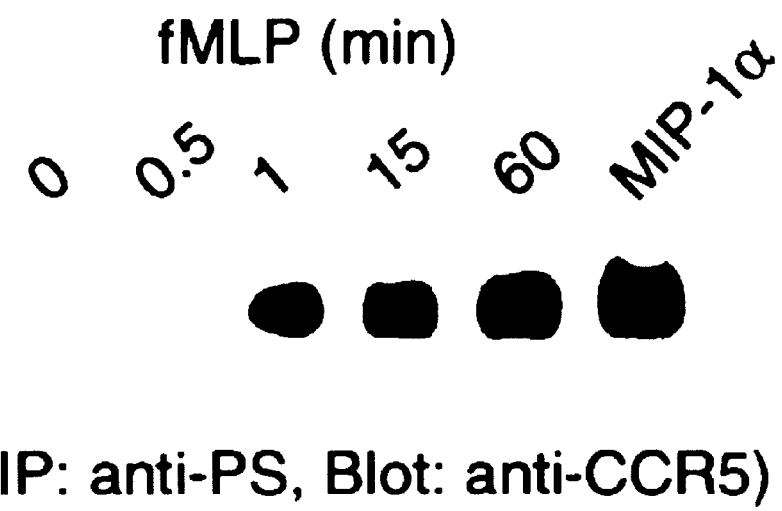

Agonist-induced phosphorylation of STM receptors such as CCR5 can result in homologous desensitization and internalization of the receptors. (Oppermann et al., *J Biol Chem*, 274:8875 (1999); Olbrich et al., *J Leukoc Biol*, 65:281 (1999); Aramori et al., *EMBO J*, 16:4606 (1997); Rodriguez-Frade et al., *J Cell Biol*, 144:755 (1999)). STM receptors can also be subjected to "heterologous desensitization" if the cells are activated by agonists using certain unrelated STM receptors. Since monocytes express a variety of STM chemoattractant receptors including the high affinity fMLP receptor, FPR, the ability of fMLP to affect the phosphorylation and expression of CCR5 was next investigated. As shown in FIG. 2A, incubation of monocytes with low nanomolar concentrations of fMLP resulted in an increased level of CCR5 phosphorylation. Furthermore, an increase in phosphorylation of CCR5 in monocytes was observed within 1 min after stimulation with fMLP (FIG.

2B) and maximal phosphorylation was observed at 60 min. These results provide evidence that the mechanisms of chemokine-induced and fMLP-induced phosphorylation of CCR5 in monocytes are distinct.

Figure 2C:
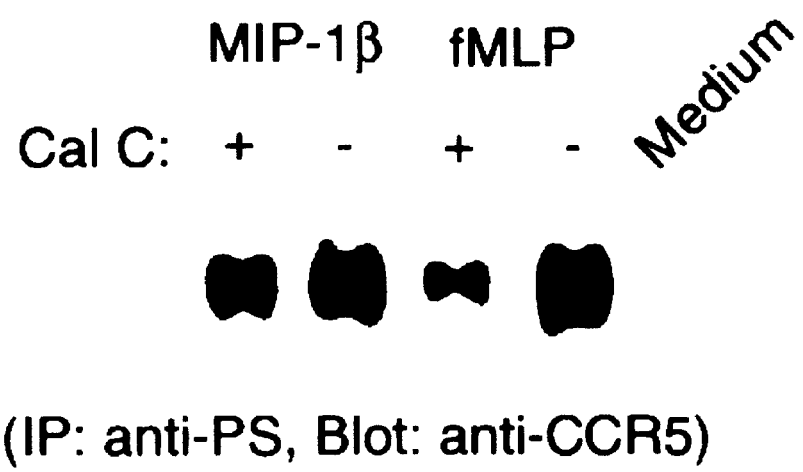

Phosphorylation of CCR5 induced by native chemokine ligands is dependent on the coupling of G-protein receptor kinases (Oppermann et al., *J Biol Chem*, 274:8875 (1999); Olbrich et al., *J Leukoc Biol*, 65:281 (1999); Aramori et al., *EMBO J*, 16:4606 (1997); Rodriguez-Frade et al., *J Cell Biol*, 144:755 (1999)). Alternatively, fMLP can exert its effect on CCR5 through a receptor "cross-desensitization" pathway, which may involve the activation of protein kinase C. (Ali et al., *J Biol Chem*, 274:6027 (1999); Ali et al., *Med Clin North Am*, 81:1 (1997); Tomhave et al., *J Immunol*, 153:267 (1994)). To test this possibility, monocytes were incubated with the specific protein kinase C ("PKC") inhibitors staurosporine or calphostin C and were subsequently stimulated with fMLP. As shown in FIG. 2C, the level of CCR5 phoshporylation induced by fMLP was markedly reduced in monocytes preincubated with calphostin C. In contrast, calphostin C had little effect on MIP-1β-induced CCR5 phosphorylation. These results support the view that fMLP-induced CCR5 phosphorylation is dependent on the activation of PKC.

Figure 2D:
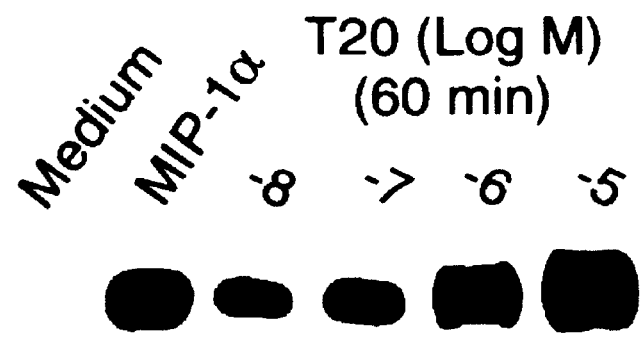

Next, the FPR class receptor ligand T20/DP178 was analyzed for its ability to activate an FPR class receptor and, thereby, induce the phosphorylation of CCR5. (Su et al., *Blood*, 93:3885 (1999); (Kilby et al., *Nat Med*, 4:1302 (1998); Lawless et al., *Biochemistry*, 35:13697 (1996); Wild et al., *AIDS Res Hum Retroviruses*, 9:1051 (1993); Wild et al., *Proc Natl Acad Sci USA*, 91:9770 (1994); and Chen et al., *J Virol*, 69:3771 (1995)). As with fMLP, the synthetic peptide T20/DP178 induced a significant and dose-dependent phosphorylation of CCR5 in monocytes (FIG. 2D), providing more evidence that activation of FPR in monocytes transduces signals leading to CCR5 phosphorylation. In the section below, a discussion of the experiments that revealed that fMLP can downregulate expression of CCR5 is provided.

fMLP-Mediated Activation of FPR Class Receptors Downregulates CCR5 Expression

Figure 3A:
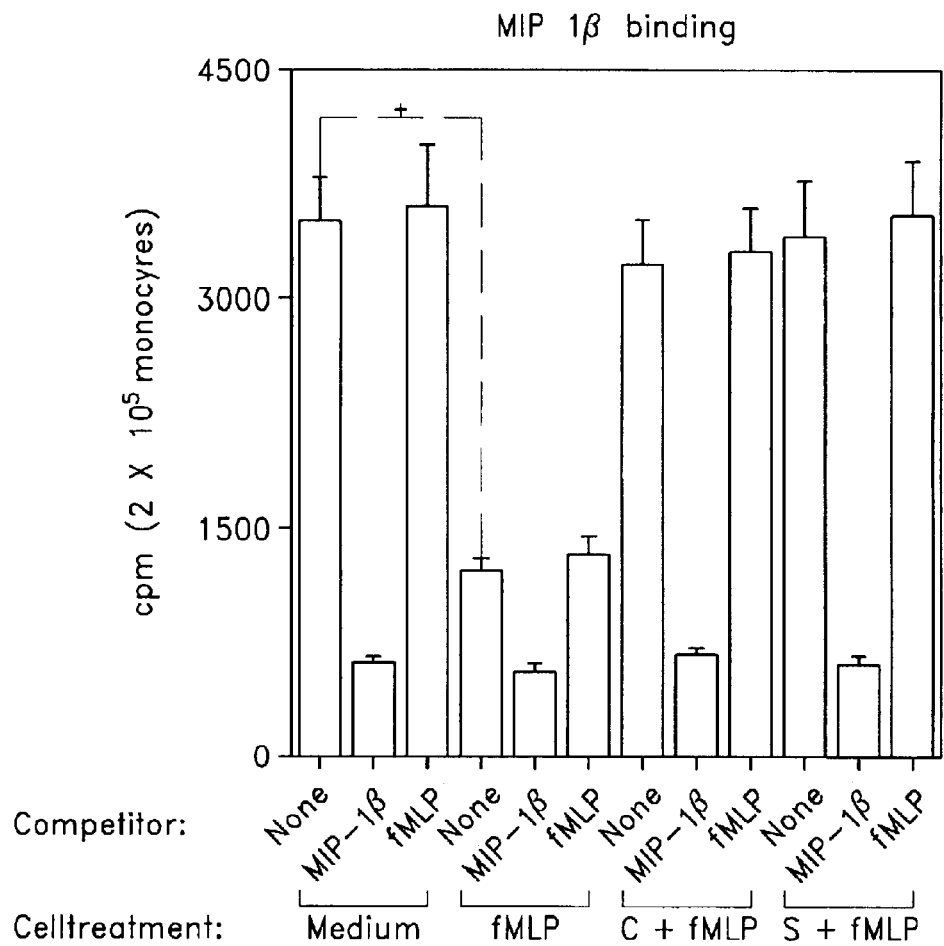

The biological consequences of fMLP-induced phosphorylation of CCR5 were studied by assaying the expression and function of CCR5 in monocytes. Freshly isolated human monocytes expressed specific binding sites for radioiodinated MIP-1β as most of the cell-associated $^{125}$I-MIP-1β could be displaced by a 1000 fold excess of unlabeled ligand. (FIG. 3A). In contrast, high concentrations of fMLP did not displace any $^{125}$I-MIP-1β binding, demonstrating that these two ligands use distinct cell surface receptors. Monocytes treated with fMLP for up to 30 min at 37° C. showed only a marginally reduced binding of $^{125}$I-MIP-1β. Treatment with fMLP for 1 h, however, markedly reduced the level of specific binding for $^{125}$I-MIP-1β and this reduction of binding was reversed if the cells were pretreated with PKC inhibitors. (FIG. 3A).

Figure 3B:
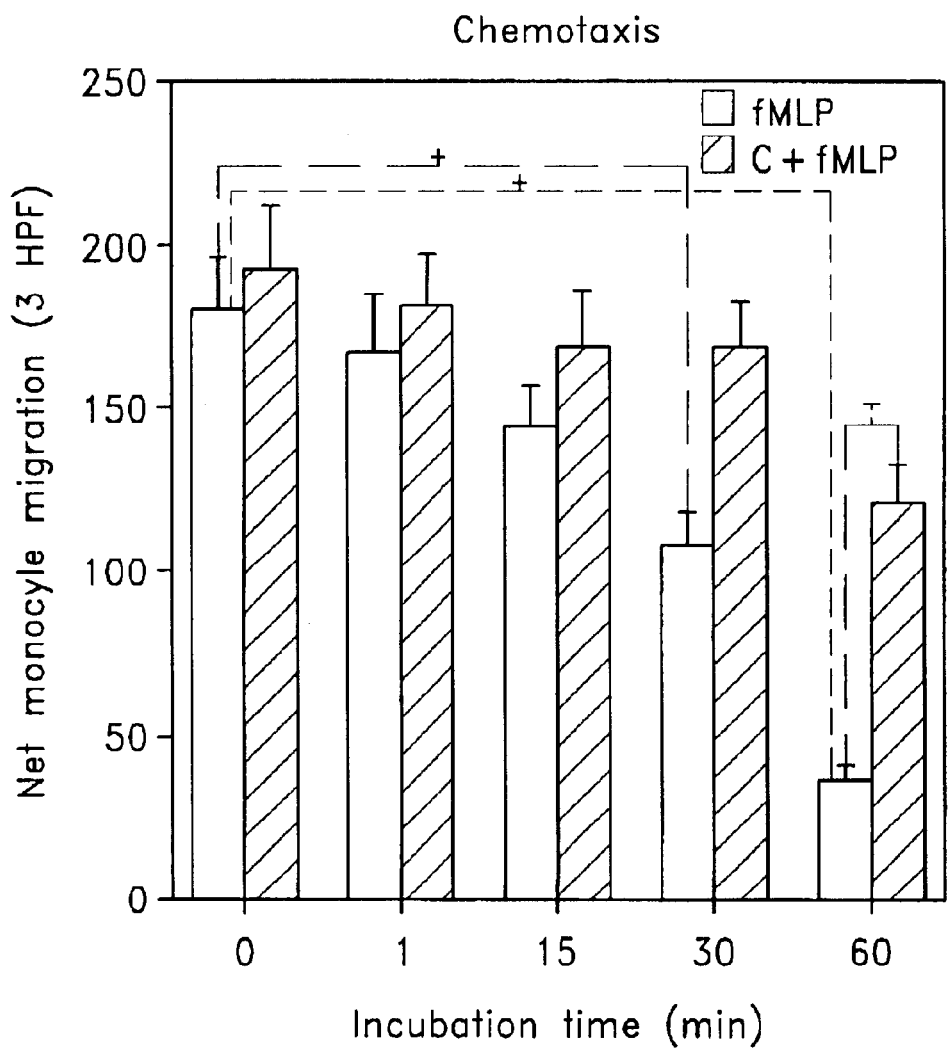
Figure 3C:
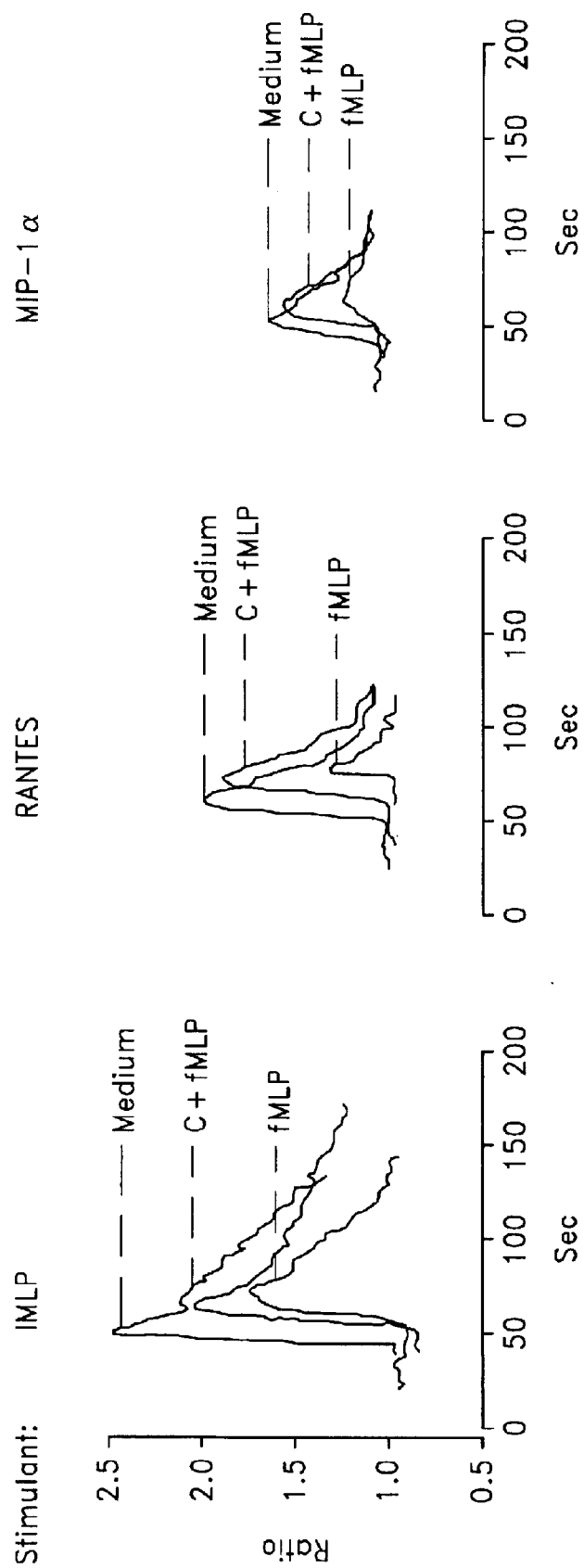

In agreement with the ligand binding results, monocytes pretreated with fMLP showed a progressively reduced chemotactic response to the CCR5 agonist MIP-1β (FIG. 3B). The functional capacity of monocytes in response to CCR5 ligands after treatment with fMLP was also examined by calcium ($Ca^{2+}$) mobilization experiments. Since MIP-1β, is a poor inducer of $Ca^{2+}$ flux in monocytes, MIP-1α and RANTES, two chemokines that activate multiple receptors including CCR5 and are marked inducers of phosphorylation of CCR5 were used. (FIGS. 2A and B). Both RANTES and MIP-1α induced a transient rise in $Ca^{2+}$ in monocytes (FIG. 3C). Cells pre-treated with fMLP, however, showed a reduced $Ca^{2+}$ flux in response to these chemokines. In contrast, monocytes pretreated with PKC inhibitors showed a virtually normal chemotactic and $Ca^{2+}$ flux response to CCR5 ligands. (FIGS. 3B and C).

Figure 4A:
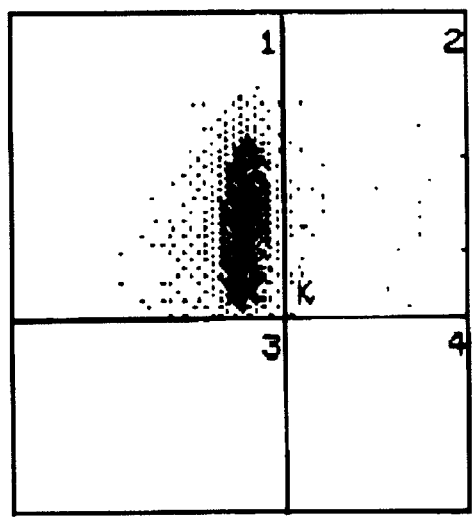
Figure 4B:
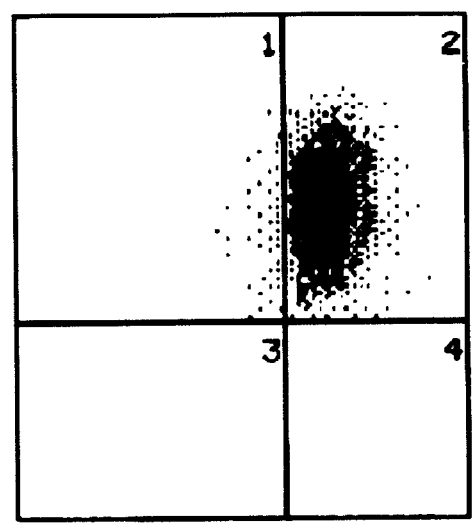
Figure 4C:
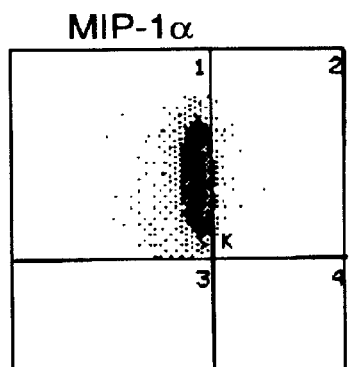
Figure 4D:
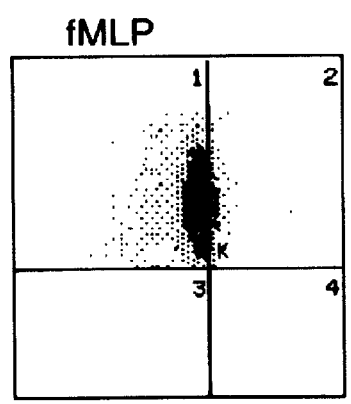
Figure 4E:
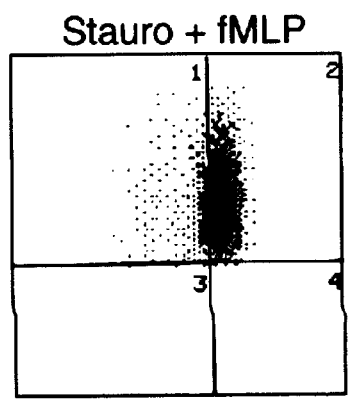

Surface expression of CCR5 on monocytes was also examined by using an anti-CCR5 antibody and flow cytometry. A substantial proportion of freshly isolated human monocytes expressed CCR5 on the cell surface (FIGS. 4A and B) and CCR5 expression was downregulated by the chemokine ligands MIP-1α, MIP-1β, or RANTES. (FIG. 4C). The expression of CCR5 on monocytes was also markedly downregulated by prior treatment of the cells with fMLP (FIG. 4D), whereas, cells preincubated with PKC inhibitors showed a level of CCR5 on the surface comparable to that on native monocytes. (FIG. 4E). These results provide evidence that phosphorylation of CCR5 induced by fMLP in monocytes resulted in the downregulation of CCR5 from the cell surface accompanied by reduced signaling capacity of cells to chemokines that use CCR5 as a functional receptor. In addition, the desensitizing effect of fMLP on the monocyte response could be reversed by PKC inhibitors, which supports the view that PKC is a critical molecule in mediating fMLP-induced CCR5 desensitization. In the section below, a discussion of the experiments that revealed that fMLP can inhibit HIV infection is provided.

fMLP-induced Activation of FPR Class Receptors Inhibits HIV Infection

Figure 5A:
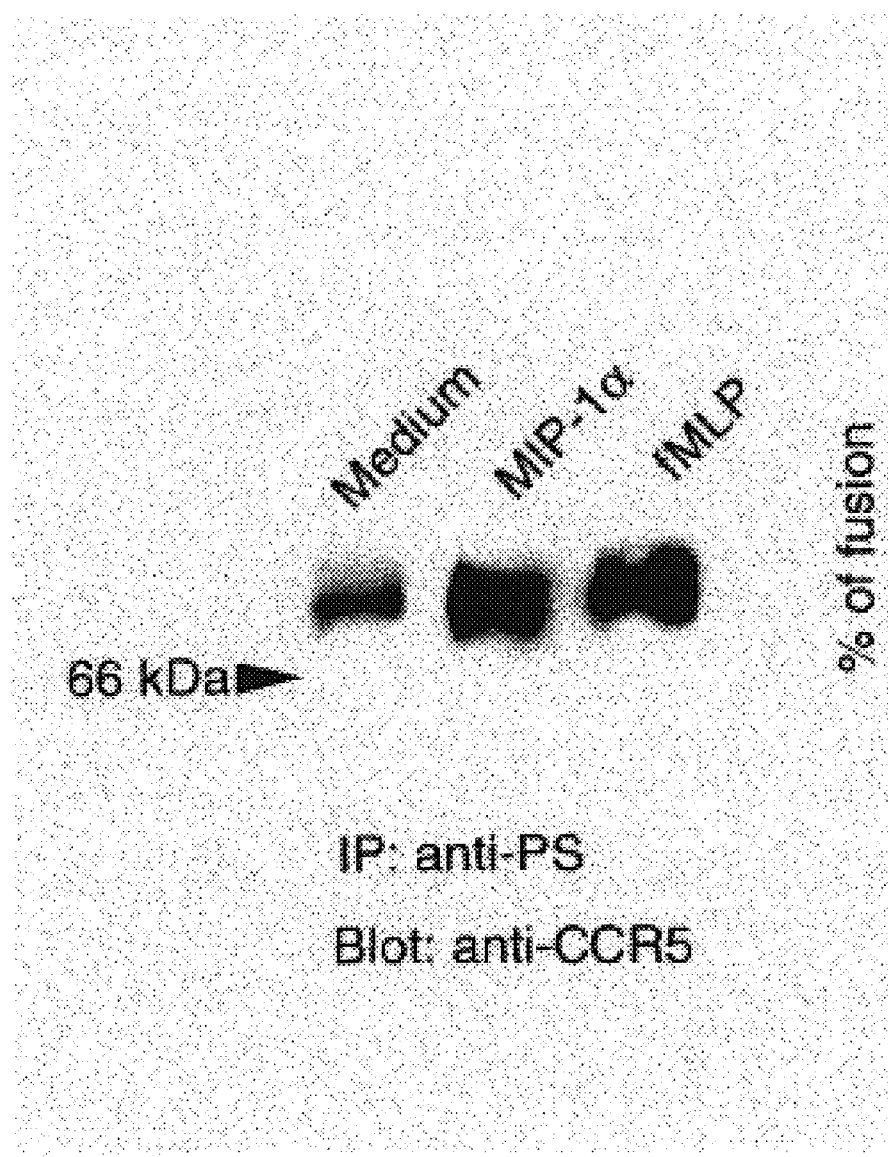

Experiments that sought to determine whether activation of an FPR class receptor can effect HIV-1 envelope fusion and HIV-1 infection were conducted as follows. The FPR class receptor, FPR, was stably transfected into the human osteosarcoma cell line (HOS), which already expressed both CD4 and CCR5. After transfection with FPR, the cells migrated and mobilized $Ca^{2+}$ in response to both fMLP and CCR5 agonists. In addition, treatment of HOS/CD4/CCR5 cells co-expressing FPR with fMLP or MIP-1α induced an increase in phosphorylation of CCR5 (FIG. 5A), establishing that both CCR5 and FPR were functionally expressed in these cells. In the presence or absence of FPR, the HOS/CD4/CCR5 cells supported HIV-1BAL-env-mediated fusion (FIG. 5B), as assessed by a quantitative β-galactosidase gene activation assay system using recombinant vaccinia virus expressing monocyte tropic HIV-1BAL-env or the reporter gene.

Figures 5B, 5C, 5D:
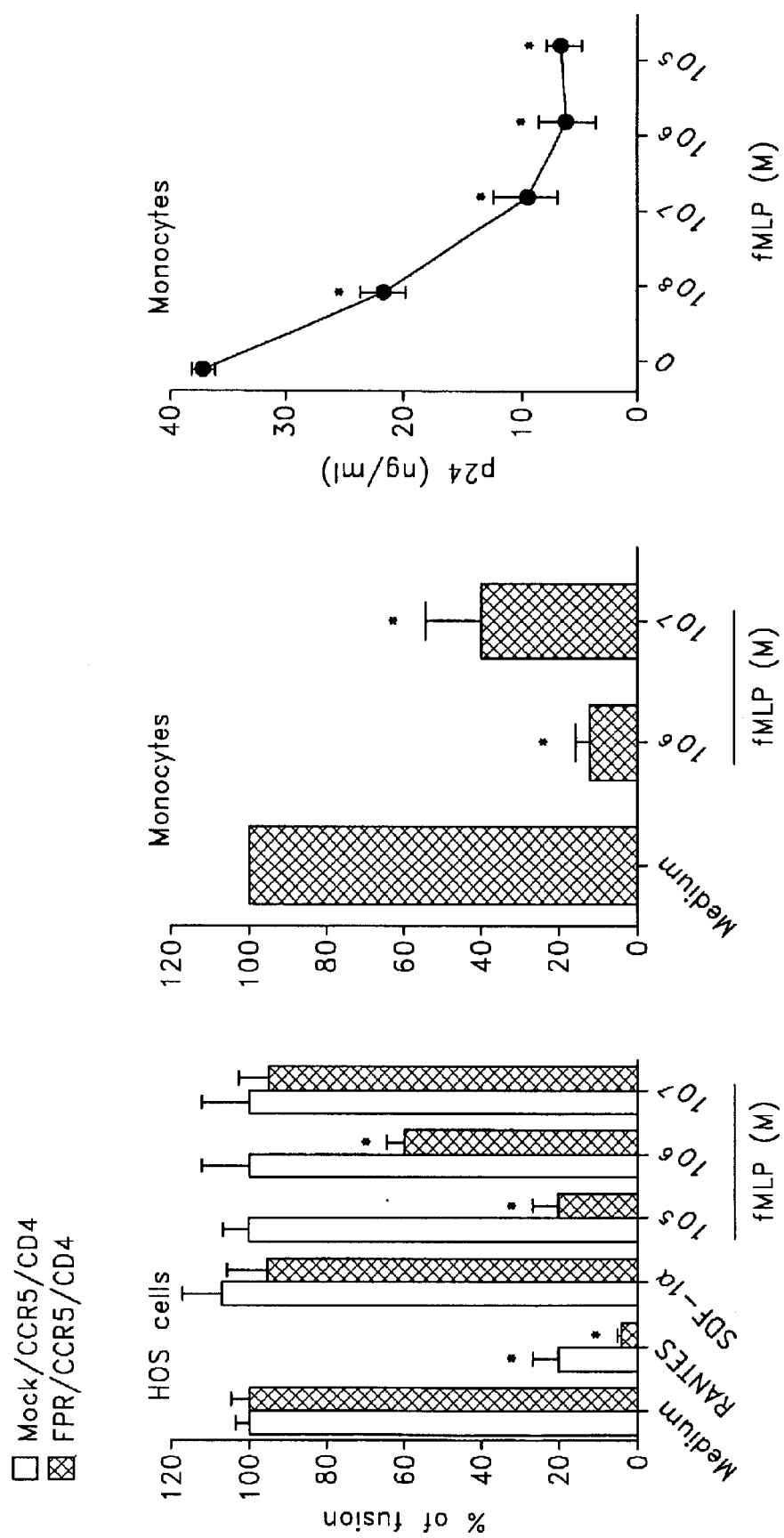

HIV-1 env fusion was inhibited by CCR5-specific chemokines. Additionally, fMLP markedly inhibited HIV-1BAL-env-mediated fusion in cells co-expressing FPR, but not in the cells expressing CD4 and CCR5 only. The effect of fMLP on HIV-1 env-mediated fusion with FPR-expressing cells was rapid, since simultaneous addition of fMLP into the fusion assay system with env-expressing cells significantly inhibited fusion (FIG. 5B). The inhibition of HIV-1 env fusion with blood monocytes in the presence of fMLP was also observed (FIG. 5C). It was also confirmed that in both FPR-transfected HOS cells and in peripheral blood monocyte/macrophages, treatment with fMLP significantly reduced the fusion and infection of the cells by monocyte tropic strains of HIV-1, as measured by syncytia formation and p24 production. (FIG. 5D). These results establish that the rapidly increased phosphorylation of CCR5 induced by fMLP effectively impaired the capacity of CCR5 to act as an HIV-1 fusion co-receptor.

The results from these initial experiments provide evidence that the expression and critical functions of the chemokine receptor CCR5 can be suppressed by a ligand for an FPR class receptor. The results establish that CCR5 in monocytes is a target of FPR activation-induced phosphorylation and that this rapid and progressively increased level of CCR5 phosphorylation is accompanied by down-regulation of the surface expression and function of CCR5 in monocytes. These results above also underscore the important role of FPR in an orchestration of multiple leukocyte chemoattractants at sites of local inflammation. Significantly, the expression and function of CCR5 can be downregulated by peptides that use an unrelated receptor. These observations spurred further investigations to identify more ligands for FPR class receptors that induce phosphorylation of CCR5, downregulation of CCR5 expression, and inhibition of HIV infection. The section below provides a discussion of the experiments that revealed that the "V3 peptide" can induce a host immune response to a pathogen.

The V3 Peptide can Induce a Host Immune Response to a Pathogen

The V3 region of HIV-1 gp120 is thought to play a major role in determining cell tropism of the HIV-1. (O'Brien et al., Nature (London), 348:69 (1990); (Sakaida et al., J. Virol., 72:9763 (1998); Shioda et al., Nature (London), 349:167 (1991); Hwang et al., Science, 253:71 (1991); and Berger, AIDS 11 (suppl A):S3 (1997)). Initially, the ability of synthetic V3 peptides to interact directly with the viral fusion co-factors such as CCR5 and CXCR4 was determined. Synthetic V3 domains, either linear or cyclized, of the T-tropic HIV strains IIIB and EL1, have been reported to directly bind CXCR4 and induce migration of both CD4$^+$ and CD8$^+$ T lymphocytes. A synthetic V3 peptide domain derived from the MN strain of the HIV-1 was tested and it was found that this V3 peptide was a potent chemoattractant for human monocytes and neutrophils (FIG. 6A) but was a weak chemoattractant for T lymphocytes. Since the chemotaxis response of human phagocytes to V3 peptide was inhibited by preincubation of the cells with pertussis toxin (FIG. 6B), it was realized that this V3 peptide activated G protein coupled STM receptor(s).

Figure 7A:
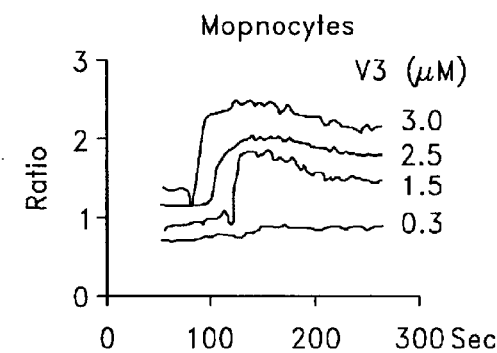
Figure 7B:
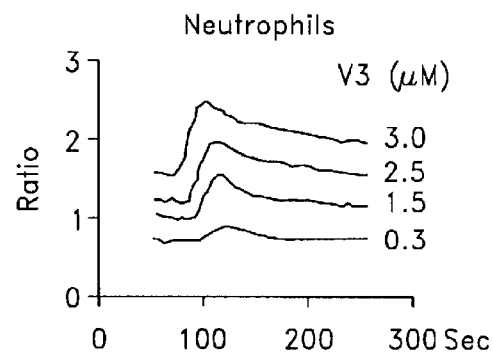
Figure 7C:
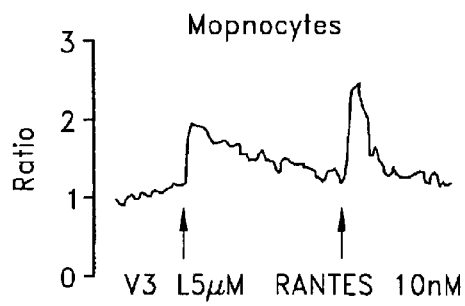
Figure 7D:
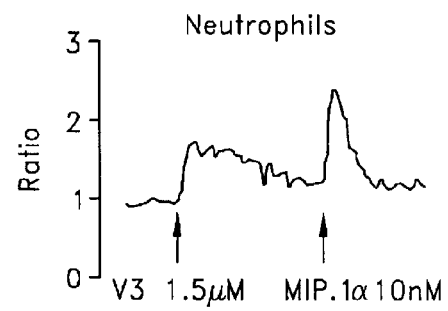
Figure 7E:
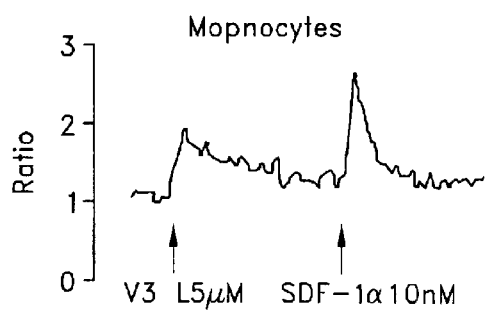
Figure 7F:
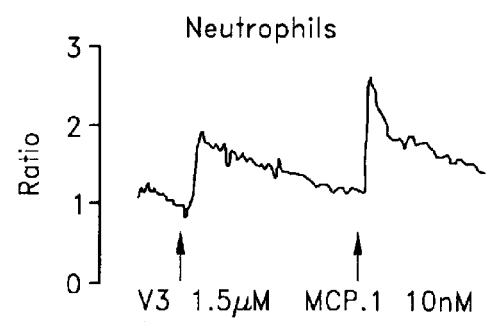
Figure 7G:
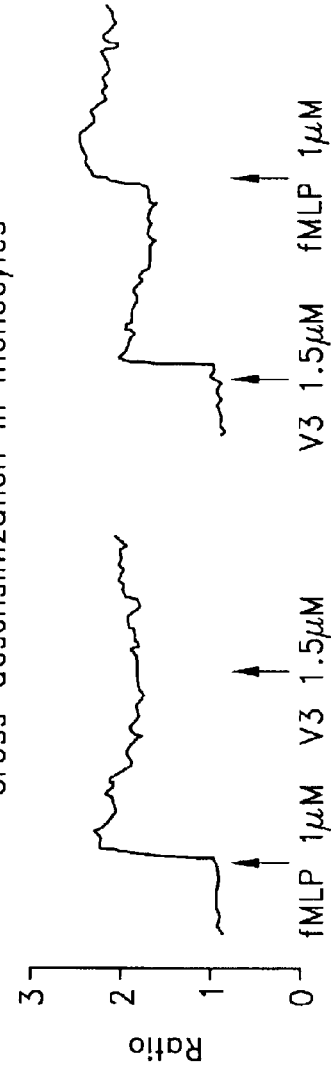
Figure 7H:
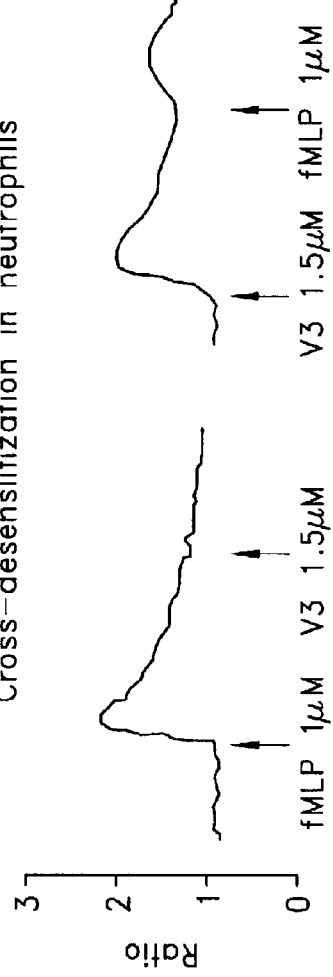

While trying to characterize the nature of the receptor(s) used by this V3 peptide, it was discovered that both monocytes and neutrophils mobilized Ca$^{2+}$ after stimulation with the peptide (FIGS. 7A and B). V3 peptide did not, however, attenuate the cell response to a number of chemokines including SDF-1α, which is a cognate ligand for the receptor CXCR4. (FIGS. 7C–F). In contrast, the signaling of V3 peptide in phagocytes was attenuated by a high concentration of fMLP or vice versa (FIGS. 7G and H), providing evidence that V3 peptide activates a low affinity receptor for fMLP. More evidence that V3 peptide activates a low affinity receptor for fMLP was obtained by analyzing cells transfected to express FPRL1. As shown in FIGS. 8A and B, V3 peptide induced both Ca$^{2+}$ mobilization and chemotaxis of HEK293 cells transfected to express FPRL1. In contrast, V3 peptide induced a low level of chemotaxis response (FIG. 8A), but not Ca$^{2+}$ mobilization in cells overexpressing FPR (FIG. 8C). These results showed that FPRL1 is a major functional receptor used by V3 peptide. The section below provides a discussion of the experiments that revealed that the V3 peptide and SAA can induce phosphorylation of the CCR5 receptor.

V3 Peptide and SAA can Induce Phosphorylation of the CCR5 Receptor

Figure 9A:
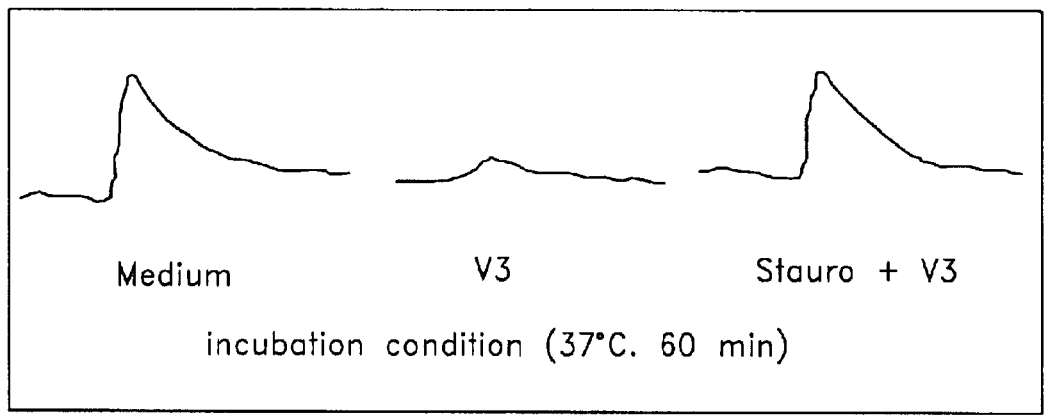
Figure 9B:
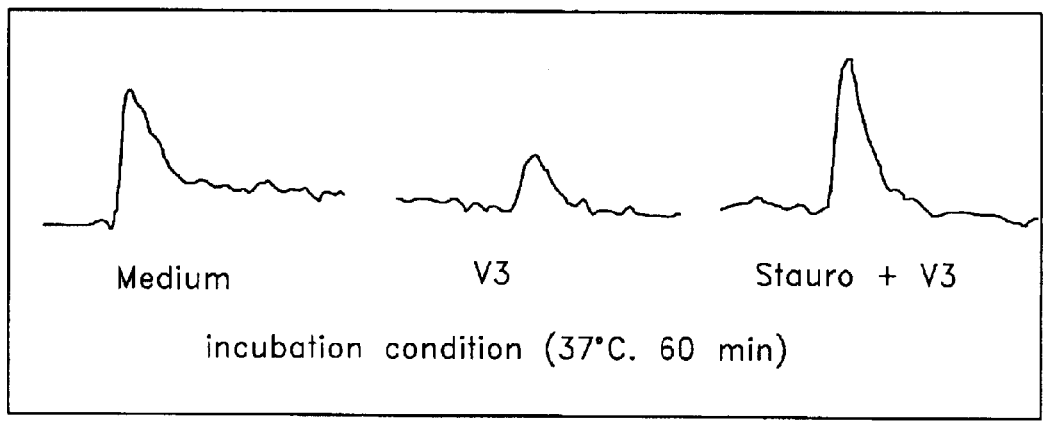
Figure 9C:
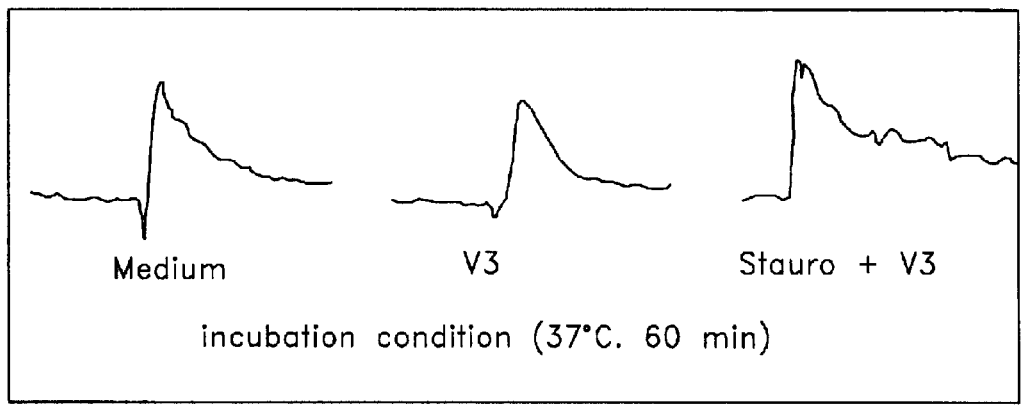
Figure 9D:
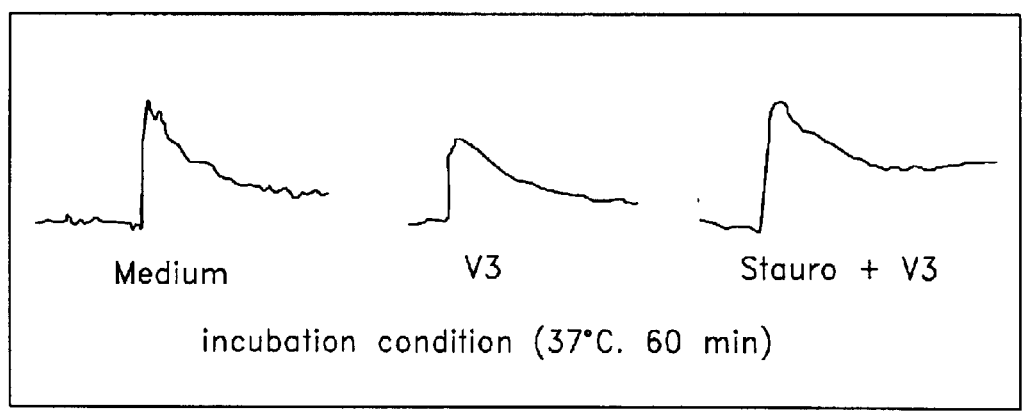

Because the stimulation of human phagocytes with V3 peptide did not attenuate the Ca$^{2+}$ flux response to subsequent challenge with chemokines, it was believed that the V3 peptide does not share receptors with the chemokines. Experiments were performed to determine whether a prolonged treatment of monocytes with V3 peptide could attenuate the cell response to chemokines, presumably through "heterologous" desensitization. The chemokines RANTES, SDF-1α, and MCP-1 all induced a significant Ca$^{2+}$ mobilization in monocytes preincubated with the culture medium. When monocytes were preincubated with V3 peptide (1.5 μM) at 37° C. for 60 min, however, the cell response to RANTES and SDF-1α, was significantly reduced. (FIGS. 9A and B). In contrast, monocytes preincubated with the protein kinase C (PKC) inhibitor staurosporine followed by V3 peptide showed almost normal Ca$^{2+}$ mobilization in response to RANTES or SDF-1α. These results provided evidence that the V3 peptide, caused a heterologous desensitization of the cell response to these chemokines by activating FPRL1 receptors to induce PKC mediated signal transduction pathway. The cell response to another chemokine, MCP-1, and the chemotactic peptide fMLP was minimally affected by preincubation with V3 peptide. (FIGS. 9C and D).

Next, experiments were performed to ascertain whether the chemokine receptor CCR5 could be phosphorylated by stimulation of monocytes with V3 peptide. The CCR5 receptors in both monocytes and receptor transfected HEK293 cells (CCR5/293 cells) were detected by immunoblotting with a polyclonal anti-CCR5 antibody as a dimerized protein species at about 75 kDa under non-reducing conditions, and an approximately 40 kDa species under reducing conditions, in agreement with the results obtained by other investigators with CCR5 transfected cell lines. (Rodriguez-Frade et al., J. Cell. Biol., 144:755 (1999)). In addition, stimulation of CCR5/293 cells, but not monocytes, with specific chemokines further promoted the dimerization of CCR5, which could be detected under non-reducing conditions.

Figures 10A, 10B, 10C, 10D:
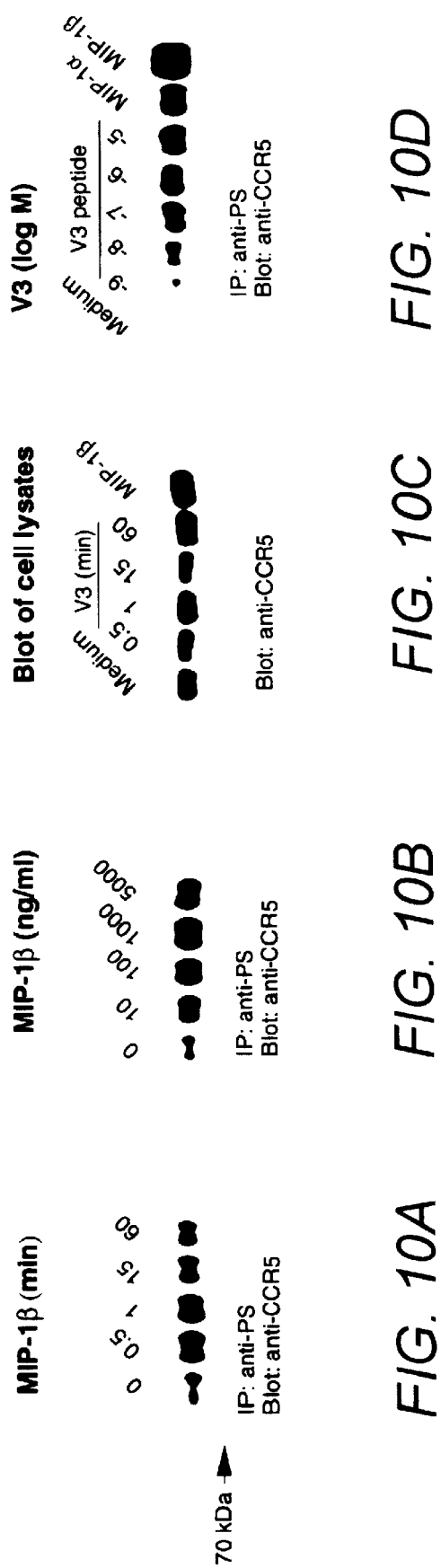
Figures 10E, 10F, 10G, 10H:
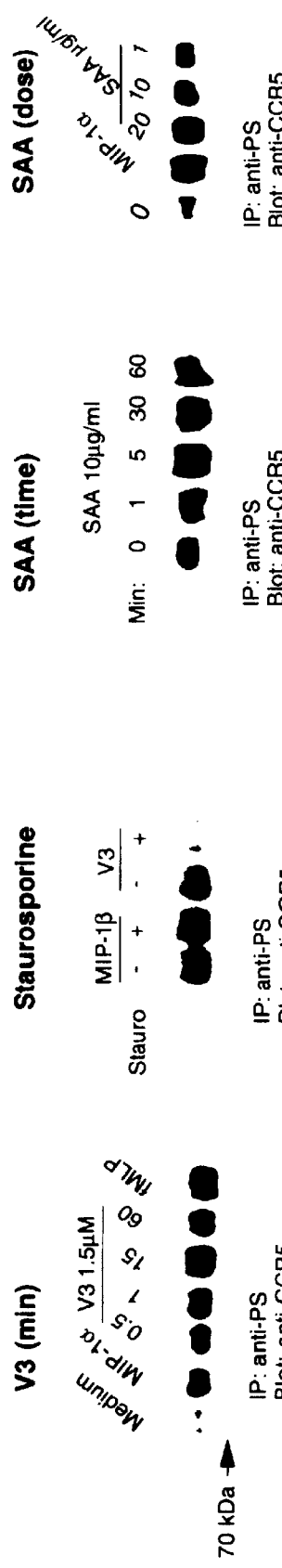

An anti-phosphoserine antibody was used to immunoprecipitate cell lysates and phosphorylated CCR5 was detected by immunoblotting the anti-phosphoserine immunoprecipitates with the polyclonal anti-CCR5 antibody. These experiments showed that CCR5 could be rapidly phosphorylated by stimulation of the cells with CCR5 chemokine agonists MIP-1α, RANTES, and MIP-1β. (FIGS. 10A and B) with the maximal level of phosphorylation occurring at 1 min. Immunoblotting of the total monocyte lysates with anti-CCR5 antibody yielded a protein species at the same molecular weight position (FIG. 10C). Although stimulation of monocytes with V3 peptide also induced significant serine phosphorylation of CCR5, the maximal level of CCR5 phosphorylation was observed at 15 min after stimulation (FIGS. 10D and E). These results are in agreement with the notion that heterologous receptor desensitization can require a longer incubation time with the stimulants and an accumulation of second messengers that culminates in phosphorylation of an unrelated STM receptor. In fact, when monocytes were pretreated with the PKC inhibitor staurosporine, V3 peptide no longer significantly induced phosphorylation of CCR5, whereas staurosporine treatment did not affect MIP-1β-induced CCR5 phosphorylation. (FIG. 10F).

The FPR class receptor ligand SAA was also analyzed for its ability to activate an FPR class receptor and induce the phosphorylation of CCR5. As with fMLP and T20, SAA induced a significant and dose-dependent phosphorylation of CCR5 in monocytes. (FIGS. 10G and H). The bacterial chemotactic peptide fMLP which uses primarily the receptor FPR in monocytes, induced CCR5 phosphorylation (FIG. 10E) with a maximal level of effect at 60 min.

The experiments above demonstrate that a synthetic V3 peptide domain of gp120 from HIV-1 MN strain induced migration and $Ca^{2+}$ mobilization in human monocytes and neutrophils by preferentially activating a G protein-coupled STM receptor FPRL1. Further, the data presented in this second group of experiments provided more evidence that activation of FPR class receptors induced phosphorylation of the chemokine receptor CCR5 in association with attenuation of the cell signaling in response to selected chemokines. Interestingly, a cyclized V3 peptide derived from HIV-1 gp120 of the MN strain (NIH AIDS Research and Reference Reagent Program) did not activate monocytes or neutrophils and both linealized or cyclized V3 peptide of the gp120 (MN) did not interact with CXCR4. These findings support the view that a secondary or tertiary structure of the peptide is crucial for the formation of a specific binding domain for CXCR4 and V3 domains of different HIV-1 strains can have divergent capacity to interact directly with chemokine fusion coreceptors. The section below provides a discussion of the experiments that revealed that the "W peptide" can induce a host immune response to a pathogen.

The W Peptide can Induce a Host Immune Response to a Pathogen

The W peptide has been reported to induce a series of signaling events in human leukocytes that were mediated by one or more G-protein coupled STM receptors but the receptor(s) for this peptide has not been identified. (Baek et al., *J. Biol. Chem.*, 271:8170–8175 (1996); Seo et al., *J. Immunol*, 158:1895–1901 (1997); Seo et al., *Clin. Biochem.*, 31:137–141 (1998); and Bae et al., *J. Leuko. Bio.*, 65:241–248 (1999)). Initial experiments foccussed on the identification of the W peptide receptor and the ability of the W peptide to induce migration of human phagocytes.

Figures 11A, 11B:
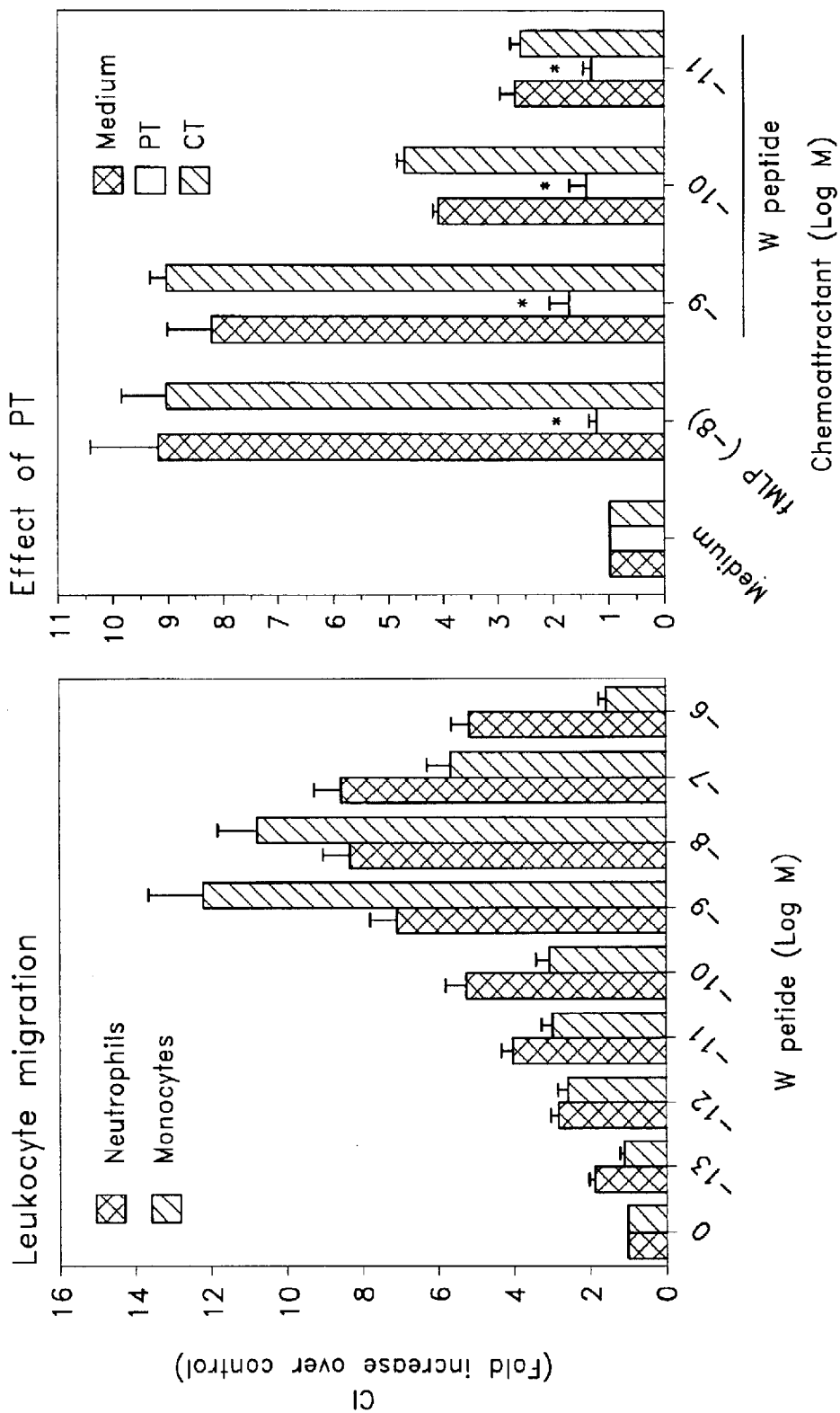

Human peripheral blood monocytes and neutrophils migrated in a dose-dependent manner in response to a concentration gradient of W peptide (FIG. 11A). The chemotactic activity of W peptide was very potent and evident at picomolar (pM) concentrations for both monocytes and neutrophils. The dose response curves were bell-shaped with maximal cell migration at low nanomolar (nM) peptide concentrations. Next, experiments were performed that accessed whether the observed phagocyte migration induced by W peptide was based on chemotaxis or chemokinesis. Checkerboard analyses showed that monocytes migrated well only when higher concentrations of W peptide were present in the lower wells of the chemotaxis chamber (Table 1). There was no increased cell migration when higher concentrations of W peptide were present in the upper wells. Equal concentrations of W peptide in both upper and lower wells induced a slight but significant increase in cell migration. These results provided evidence that the cell migration induced by W peptide was due to a chemotactic effect with a minor contribution based on chemokinesis.

TABLE 1

Checkerboard Analysis of Monocyte Migration in Response to W Peptide[a]

| W peptide in | Number of migrated cells in 1 HPF (mean ± SE) W peptide in upper wells (M) | | | |
|---|---|---|---|---|
| lower wells (M) | Medium | $10^{-10}$ | $10^{-9}$ | $10^{-8}$ |
| Medium | 26 ± 3 | 31 ± 3 | 28 ± 3 | 29 ± 2 |
| $10^{-10}$ | 84 ± 5[b] | 52 ± 6 | 47 ± 3 | 31 ± 3 |
| $10^{-9}$ | 183 ± 11[b] | 160 ± 13[b] | 120 ± 15[b] | 49 ± 4 |
| $10^{-8}$ | 326 ± 21[b] | 297 ± 32[b] | 236 ± 5[b] | 105 ± 6[b] |

[a]Different concentrations of W peptide were placed in the upper and/or lower wells of the chemotaxis chamber, monocytes at 2 × 10⁶/ml were placed in the upper wells. The upper and lower wells were separated by a polycarbonate filter. After incubation, the non-migrating cells were removed and the filter was fixed, stained and the cells migrated across the filter were counted in three high powered fields (HPF, 400 x). The results are expressed as the mean number (± SE) of the cells in 1 HPF.
[b]$P < 0.01$ compared with migration in the presence of medium alone in both upper and lower wells as determined by Student's t test.

Figure 12A:
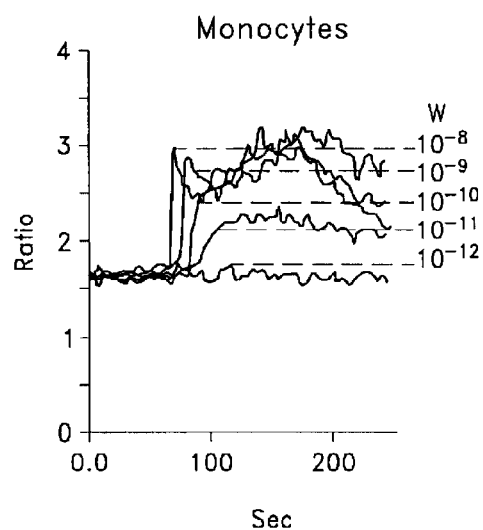

Migration of phagocytes in response to W peptide was completely inhibited by pretreatment of the cells with pertussis toxin (PT), but not by cholera toxin (CT) (FIG. 11B) or herbimycin A, providing evidence that a Gi protein coupled receptor was involved. This finding was further supported by evidence that the W peptide potently induced a dose-dependent, and pertussis toxin sensitive, calcium ($Ca^{2+}$) mobilization in monocytes and neutrophils. (FIGS. 12A and E). In agreement with the observed W peptide-mediated chemotactic activity, $Ca^{2+}$ mobilization was detected when the W peptide was provided at pM concentrations.

Figure 12B:
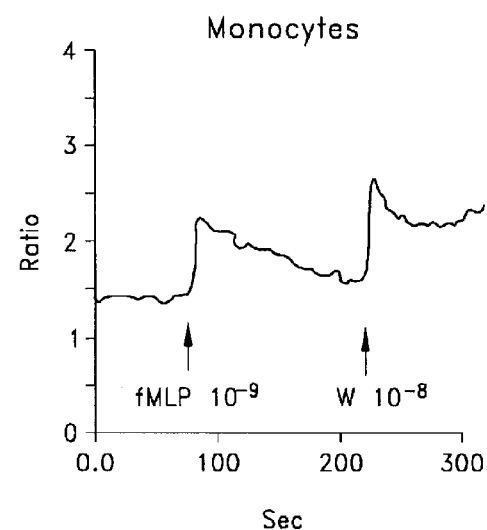
Figure 12C:
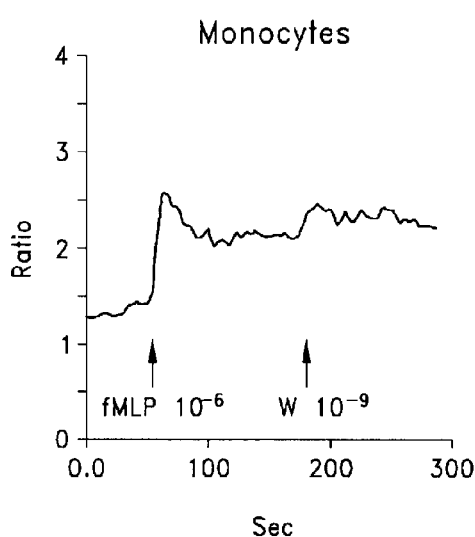
Figure 12D:
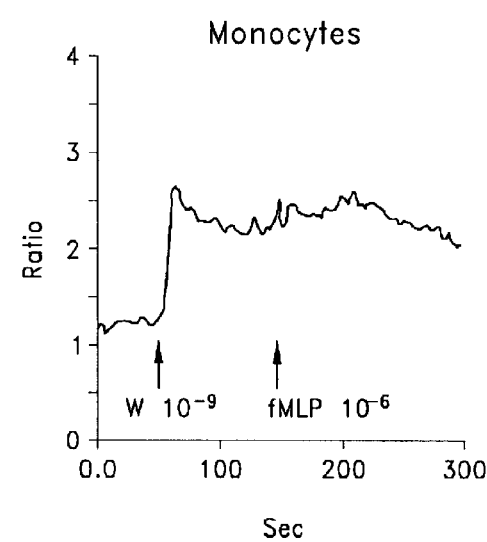
Figure 12E:
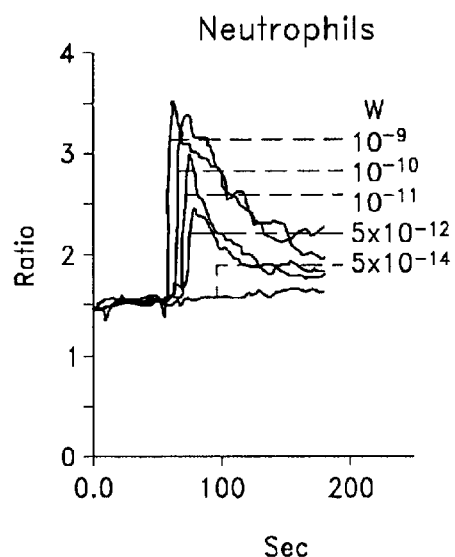
Figure 12F:
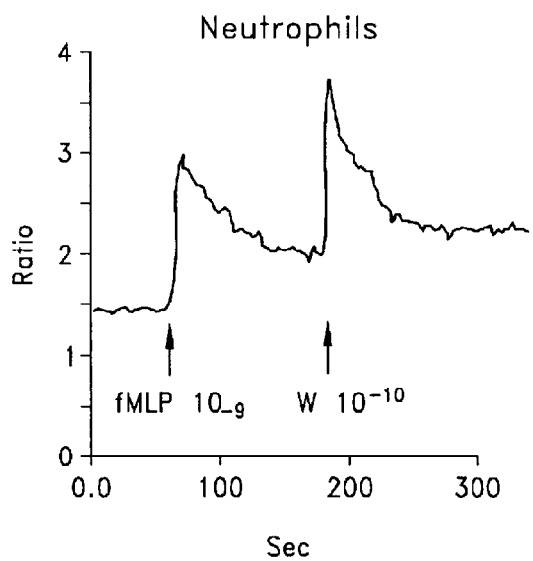
Figure 12G:
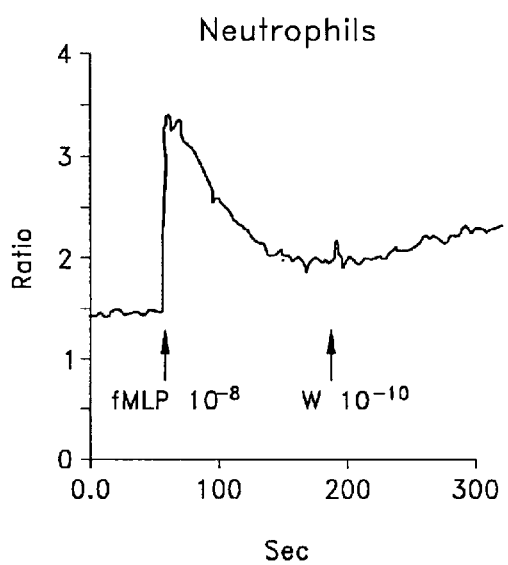
Figure 12H:
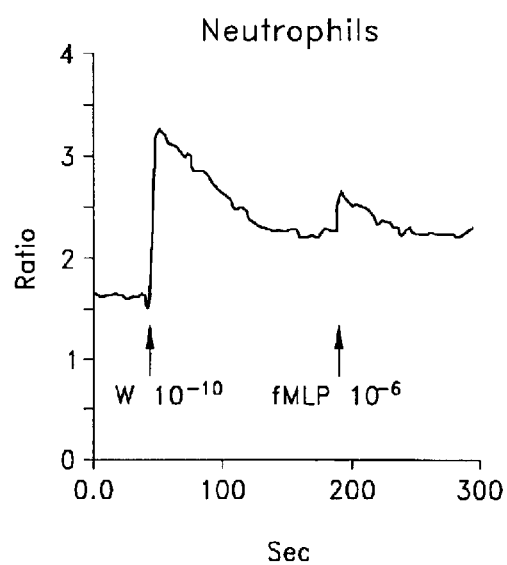

To further characterize the W peptide receptor on phagocytic cells, a series of experiments examining cross-desensitization of $Ca^{2+}$ mobilization were performed using a variety of chemoattractants. The $Ca^{2+}$ flux induced by W peptide in monocytes or neutrophils was not desensitized by various chemokines including MCP-1, RANTES, MCP-3, MIP-1α, IL-8, and SDF-1α. These results suggested that W peptide did not share a receptor with any of these chemokines. Low concentrations (in the nM range) of fMLP also had a limited effect on W peptide-induced $Ca^{2+}$ flux. (FIGS. 12B and F). When the concentrations of fMLP were increased to the micromolar range, however, the response to W peptide in monocytes (FIG. 12C) or neutrophils (FIG. 12G) was significantly attenuated. Moreover, W peptide was able to desensitize the $Ca^{2+}$ flux response to $10^{-3}$–$10^{-4}$ fold higher concentrations of fMLP in both monocytes (FIG. 12D) and neutrophils (FIG. 12H). These results support the view that W peptide shares receptor(s) with fMLP on human phagocytic cells and activates the receptor(s) with much higher efficiency than fMLP.

Figure 13A:
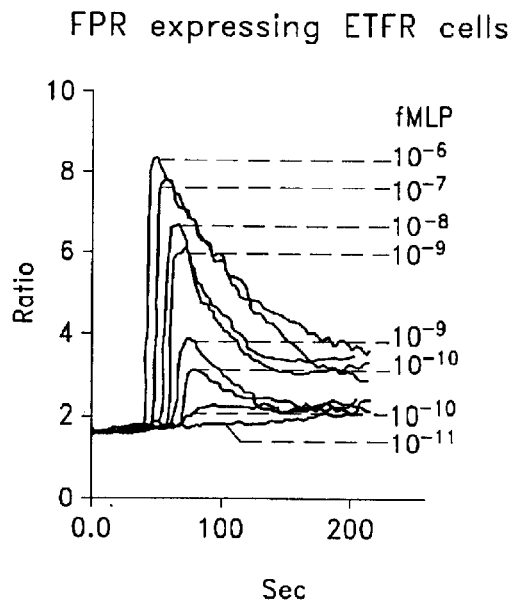
Figure 13B:
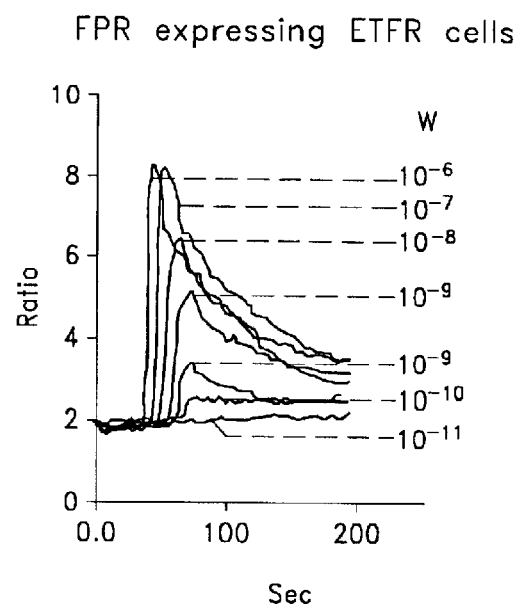

Next, the effect of W peptide on cells transfected to express FPR or FPRL1 was analyzed. fMLP was provided over a wide range of concentrations and induced $Ca^{2+}$ mobilization in an FPR-transfected rat basophil leukemia cell line (ETFR cells), with a minimal effective dose at $10^{-10}$ M. (FIG. 13A). In contrast, the minimal effective concentration for fMLP to induce $Ca^{2+}$ mobilization in FPRL1 transfected cells (FPRL1/293 cells) was in the μM range (FIG. 13E). The W peptide also induced $Ca^{2+}$ mobilization in cells transfected with either of these FPR class receptors (FIGS. 13B and F). The minimal effective doses for W peptide to activate both FPR and FPRL1, however, were at $10^{-11}$ M, which demonstrates that W peptide activates these receptors with higher efficiency than fMLP.

Figure 13C:
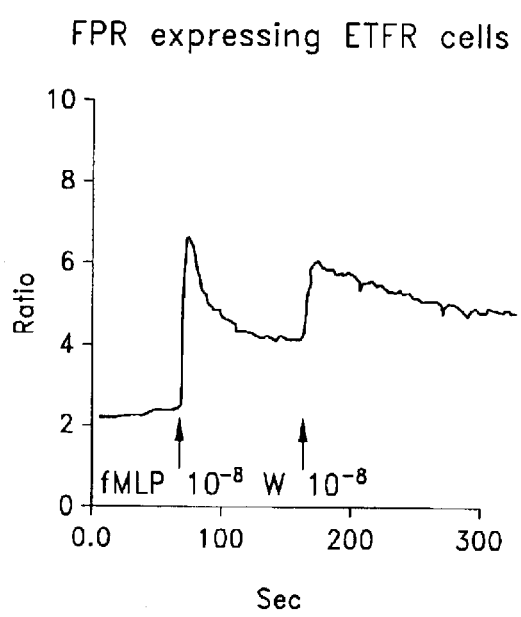
Figure 13D:
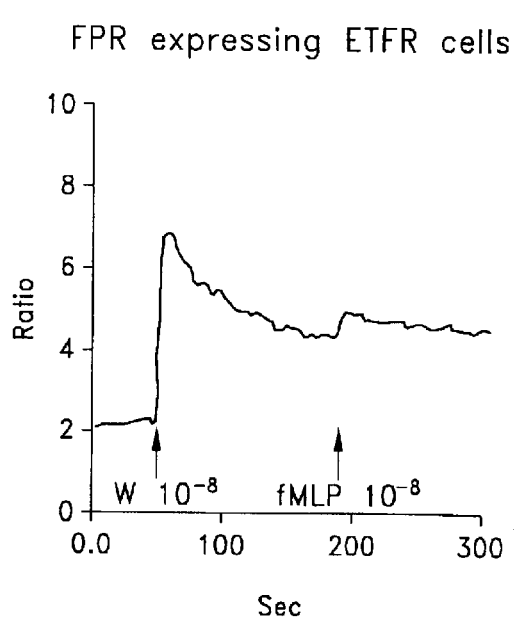

This finding was further supported by cross-desensitization of $Ca^{2+}$ flux between W peptide and fMLP in both receptor transfectants. As shown in FIGS. 13G and H, although sequential stimulation of the cells expressing FPRL1 with W peptide and fMLP resulted in bidirectional desensitization, a $10^5$ fold excess of fMLP was required to desensitize the effect of W peptide in FPRL1/293 cells. Likewise, in ETFR cells, with equal concentrations, W peptide more potently desensitized the effect of fMLP. (FIGS. 13C and D). In control experiments, W peptide and fMLP did not induce $Ca^{2+}$ mobilization in parental or mock transfected rat basophil cell line and HEK 293 cells. These results provide evidence that W peptide activates both FPR and FPRL1 receptors with high potency.

Figure 14A:
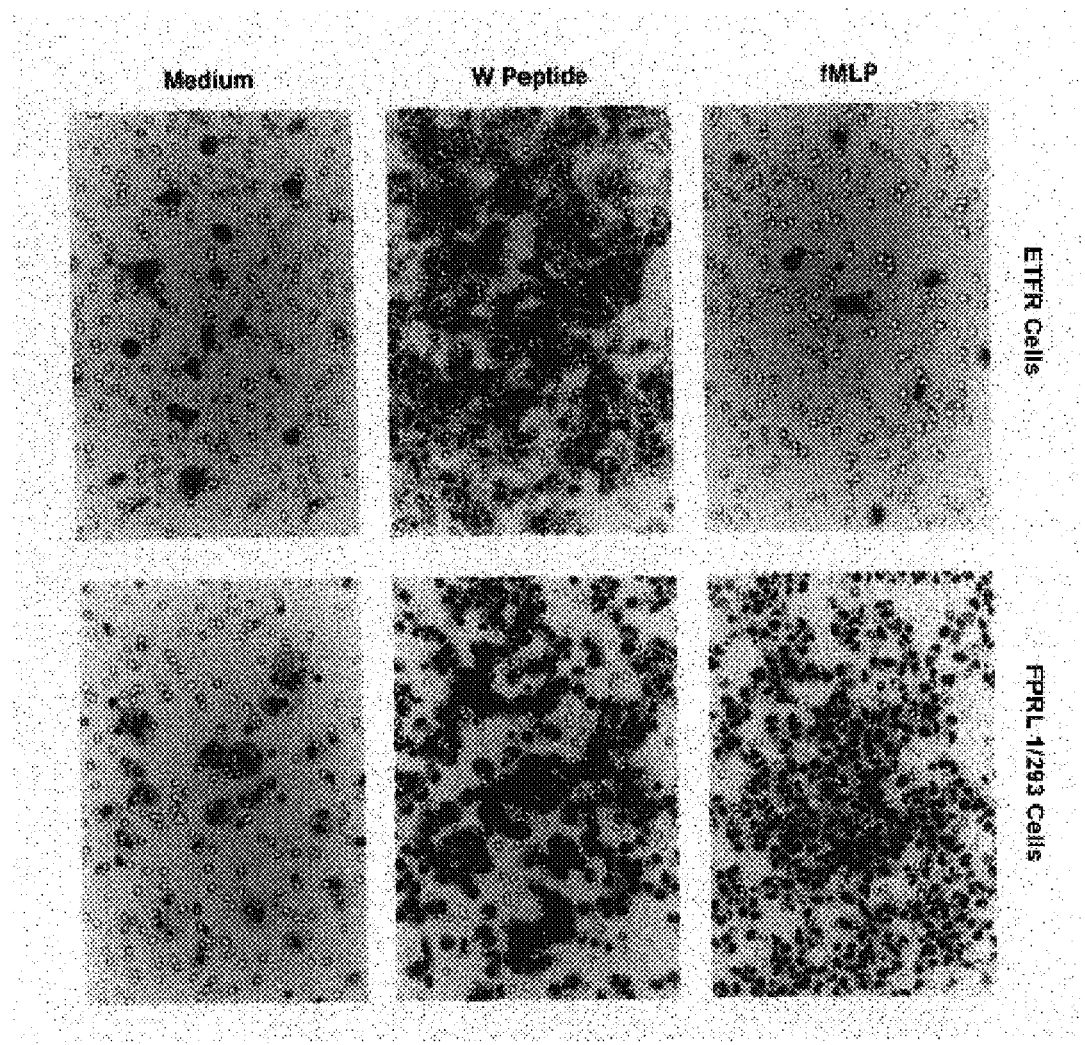
Figures 14B, 14C, 14D:
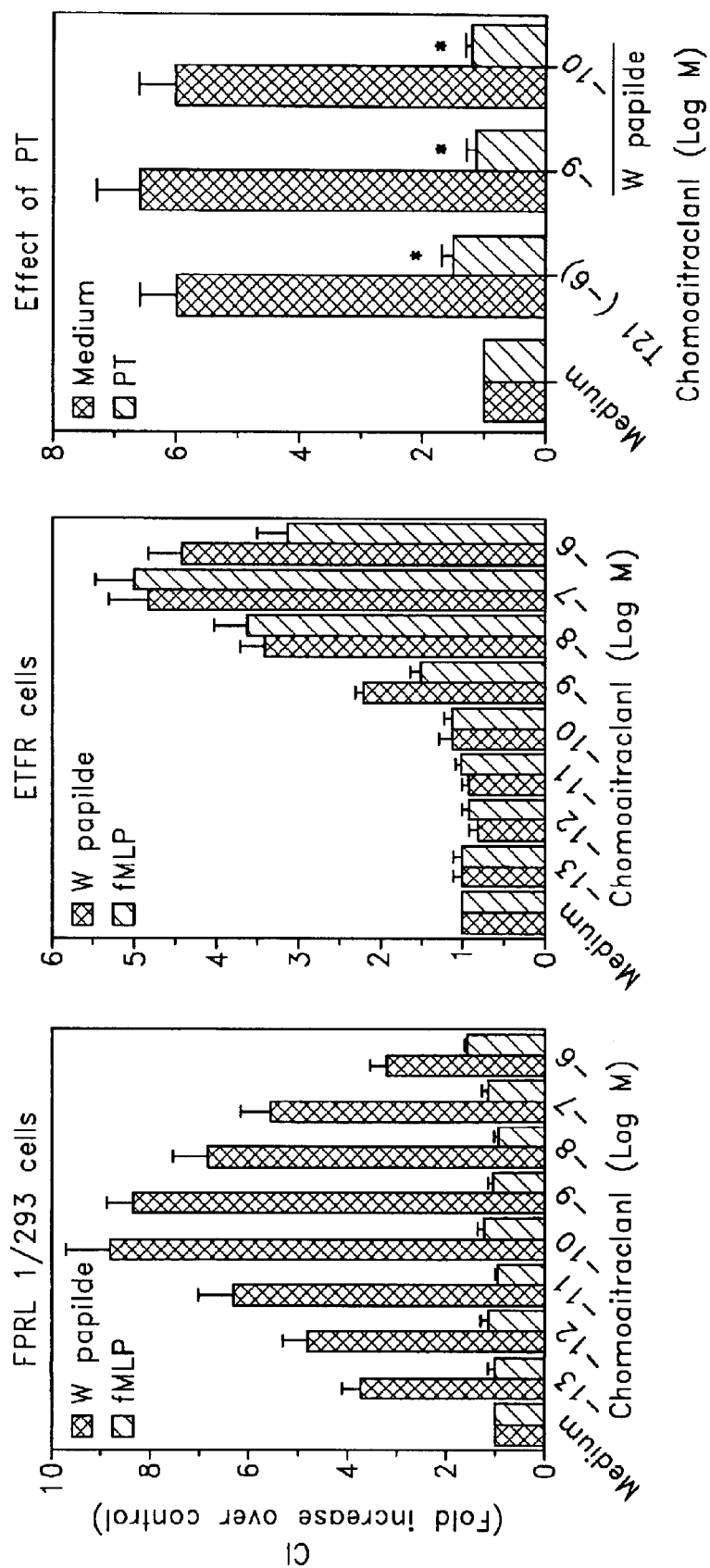

The ability of W peptide to induce migration of cells transfected with FPR or FPRL1 was also tested. FPRL1/293 cells showed a marked migratory response to W peptide with an EC50 of ~1 pM (FIGS. 14A and B), but these cells failed to migrate in response to a wide concentration range of fMLP (FIGS. 14A and B). On the other hand, both fMLP and W peptide induced the migration of the ETFR cells with comparable dose-response curves (FIGS. 14A and C). These chemotaxis experiments demonstrate that fMLP is only a partial and low affinity agonist for FPRL1 since it does not induce migration of FPRL1 expressing cells. W peptide, on the other hand, was found to be a very efficient agonist for both FPR and FPRL1, with even higher efficacy for FPRL1 than FPR; as low picomolar concentrations of W peptide are sufficient to induce both $Ca^{2+}$ flux and chemotaxis in these cells.

As observed with phagocytic cells, the W peptide induced migration of FPRL1/293 (FIG. 14D) and ETFR cells was inhibited by pretreatment of the cells with pertussis toxin. To further confirm that W peptide shares receptors with fMLP, ligand binding competition experiments with $^3$H-labeled fMLP were performed. In agreement with the chemotactic and $Ca^{2+}$ mobilization activity for the ETFR cells, W peptide effectively competed with $^3$H-fMLP for binding to ETFR cells (FIG. 15). $^3$H-fMLP did not significantly bind to FPRL1/293 cells, presumably due to its low affinity for FPRL1. The results presented in this section demonstrate that W peptide can induce chemotaxis and $Ca^{+2}$ mobilization, cellular events associated with a host immune response to a pathogen, by interacting with FPR class receptors. The section below discusses experiments that show that W peptide can inhibit HIV infection.

W Peptide Inhibits HIV Infection

Figures 16A, 16B:
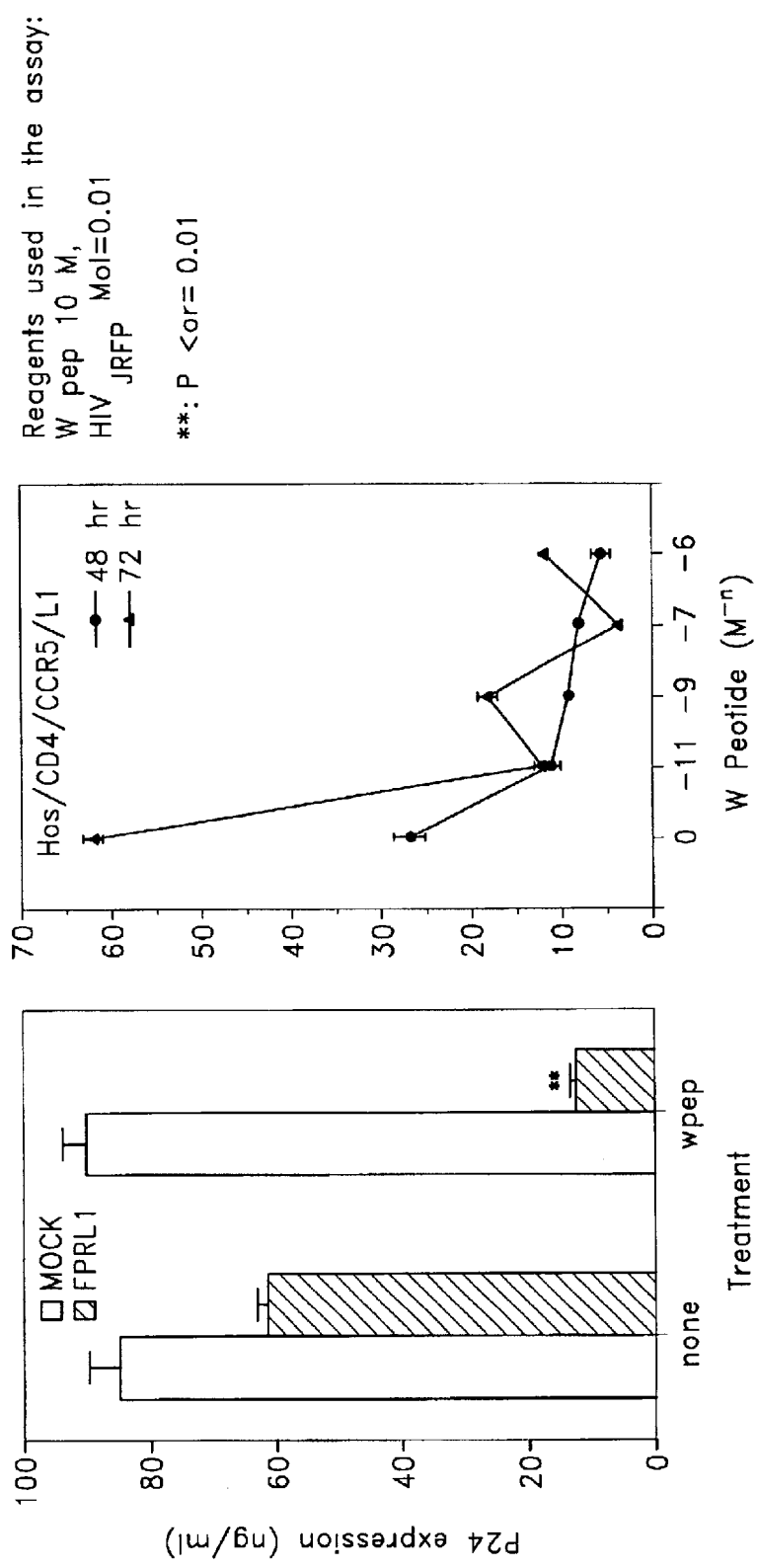

After discovering that the W peptide activates FPR class receptors and induces cellular events associated with a host immune response to a pathogen, experiments were performed to determine whether W peptide can inhibit HIV infection. The FPR class receptor, FPRL1, was stably transfected into the human osteosarcoma cell line (HOS), which already expressed both CD4 and CCR5. Hos cells expressing CD4/CCR5/FPRL1 receptors were first treated with W peptide at designated concentrations for 1 hour followed by infection with HIV-1$_{JRFL}$ for one hour. The infected cells were washed three times with medium and placed in culture. The levels of p24 were measured by ELISA at 48 hours and 72 hours post-infection. FIG. 16A shows that exposure of W peptide [$10^{-5}$M] at the initial step of HIV-1 infection significantly reduced HIV-1 infectivity in FPRL1 transfectants but not mock transfected cells. W peptide was found to reduce HIV-1 infectivity at concentrations as low as $10^{-11}$M. FIG. 16B. In accordance with the HIV infectivity experiments performed in the presence of fMLP, W peptide effectively inhibited the propagation of HIV. These results also establish that ligands that interact with either FPR or FPRL1 can inhibit HIV infection.

W peptide was derived from a biologically active peptide WKYMVM-NH$_2$ (SEQ. ID. No. 1). isolated from a peptide library. (Seo et al., J. Immunol., 158:1895–1901 (1997)). WKYMVM-NH$_2$ (SEQ. ID. No. 1) stimulates phosphoinositide hydrolysis in a human B cell line and based on its inhibition by pertussis toxin, the usage of a Gi protein coupled, STM receptor was postulated. (Baek et al., J. Biol. Chem., 271:8170–8175 (1996)). A modification of the methionine at the NH$_2$ end with D-type amino acid yielded WKYMVM ("W peptide" SEQ. ID. No. 1), which exhibited more than a hundred fold increase in its biological effect than its prototype WKYMYM-NH$_2$ (SEQ. ID. No. 4) and stimulated a variety of STM, G-protein receptor mediated signaling events in human monocytes (Bae et al., J. Leuko. Bio., 65:241–248 (1999)) and neutrophils (Seo et al., J. Immunol., 158:1895–1901 (1997)) in addition to B lymphocytes.

The combined results from the experiments above provide evidence that activation of FPR class receptors (e.g., either FPR and FPRL1) by several different ligands induces the phosphorylation of CCR5, the downregulation of CCR5, and the inhibition of HIV infection. More specifically, the data above has shown that fMLP, T20, V3 peptide, and SAA activate FPR class receptors and, thereby, phosphorylate CCR5. The data above also has shown that phosphorylation of CCR5 results in the downregulation of CCR5 from the cell surface and an attenuation of signaling through CCR5 by chemokines. Furthermore, the data above has shown that fMLP can inhibit HIV-1 infection by interacting with FPR and W peptide can inhibit HIV-1 infection by interacting with FPRL1. It is therefore contemplated that several ligands, which interact with FPR class receptors, can activate these receptors to transduce a signal that results in phosphorylation of CCR5, which in turn, downregulates CCR5 from the cell surface resulting in an inhibition of fusion and, thus, propagation of HIV-1.

Although early studies indicated that the N-formyl group present on fMLP was essential for optimal agonist potency, recent studies have shown that non-formylated peptides can also bind and activate FPR. (Freer et al., Biochemistry, 21:257 (1982); Higgins et al., J Med Chem, 39:1013 (1996); both references are herein incorporated by reference). The synthetic pentapeptide Met-Ile-Leu-Phe-Phe-OH (SEQ. ID. No. 2), either N-formylated or N-acetylated, is more potent than parental fMLP in the induction of $Ca^{2+}$ flux in human neutrophils, for example. (Murphy. Annu Rev Immunol, 12:593 (1994); Murphy, "The N-formyl peptide chemotactic receptors," Chemoattractant ligands and their receptors, CRC Press, Boca Raton, 1996:269; Prossnitz and Ye, Pharmacol Ther, 74:73 (1997); both references are herein incorporated by reference). Amino terminal urea-substituted and carbomate-modified peptides are also efficacious agonists for the FPR. (Higgins et al., J Med Chem, 39:1013 (1996), herein incorporated by reference). The results above also established that molecules that do not bear any sequence identity to the reported FPR agonists, such as T20/DP178, V3 peptide, and W peptide are effective at inhibiting HIV infection. Moreover, several peptides derived from a plasmid based random library have been shown also to be highly efficacious agonists for FPRL1. (Klein et al., Nat. Biotechnol., 16:1334–1337 (1998)).

In addition to peptide and protein agonists, a lipid metabolite lipoxin A4 (LXA4) has been reported to be a high affinity ligand and potent agonist for FPRL1 (also thus termed LXA4R). (Fiore et al., J. Exp. Med., 180:253–260 (1994)). LXA4 is an eicosanoid generated during a number of host reactions such as inflammation, thrombosis and atherosclerosis, and was initially discovered as an inhibitor of immune responses. LXA4 bound to Chinese Hamster Ovary cells (CHO cells) transfected with FPRL1(LXA4R) with high affinity and increased GTPase activity and the release of esterified arachidonate. (Fiore et al., *J. Exp. Med.*, 180:253–260 (1994)). Thus, many different classes of molecules can interact with FPR class receptors. The section below provides a discussion of several binding partners for FPR class receptors that induce a host immune response to a pathogen and/or inhibit HIV infection.

The use of binding partners for FPR class receptors to induce a host immune response to a pathogen and/or inhibit HIV infection In several embodiments, fMLP, V3 peptide, SAA, T20, and W peptide, and fragments or derivatives of these molecules are incorporated into biotechnological tools and pharmaceuticals for therapeutic and prophylactic application. Desirably, fMLP, V3 peptide, SAA, T20, and W peptide, and fragments or derivatives of these molecules are provided to subjects to induce a host immune response to a pathogen and/or inhibit HIV infection. Often times isolated or purified fMLP, V3 peptide, SAA, T20, and W peptide, and fragments or derivatives of these molecules are used. The term "isolated" requires that the material be removed from its original environment (e.g., the natural environment if it is naturally occurring). For example, a naturally occurring protein present in a living cell is not isolated, but the same protein, separated from some or all of the coexisting materials in the natural system, is isolated. The term "purified" does not require absolute purity; rather it is intended as a relative definition. For example, proteins are routinely purified to electrophoretic homogeneity, as detected by Coomassie staining, and are suitable in several assays despite having the presence of contaminants.

Preferably, the fMLP, V3 peptide, SAA, T20, and W peptide, and fragments or derivatives of these molecules correspond to sequences involved in assembly of the ligand/FPR class receptor complex. Desirable peptides are between three amino acids and 100 amino acids in length and have at least some portion of the sequence of a peptide that is involved in assembly of the ligand/FPR class receptor complex. Additionally, peptidomimetics that resemble fMLP, V3 peptide, SAA, T20, and W peptide, and fragments or derivatives of these molecules of between three and 100 amino acids are used with embodiments of the invention. For example, an oligopeptide for use in aspects of the invention can have three amino acids, four amino acids, five amino acids, six amino acids, seven amino acids, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty nine, or forty or fifty or sixty or seventy or eighty or ninety or one-hundred or more amino acids. Similarly, peptidomimetics of the invention can have structures that resemble three amino acids, four amino acids, five amino acids, six amino acids, seven amino acids, eight, nine, ten, eleven, twelve, thirteen, fourteen, fifteen, sixteen, seventeen, eighteen, nineteen, twenty, twenty-one, twenty-two, twenty-three, twenty-four, twenty-five, twenty-six, twenty-seven, twenty-eight, twenty-nine, thirty, thirty-one, thirty-two, thirty-three, thirty-four, thirty-five, thirty-six, thirty-seven, thirty-eight, thirty nine, or forty or fifty or sixty or seventy or eighty or ninety or one-hundred or more amino acids.

Peptides for use in aspects of the invention can also be modified, e.g., the peptides can have substituents not normally found on a peptide or the peptides can have substituents that are normally found on the peptide but are incorporated at regions of the peptide that are not normal. The peptides for use in aspects of the invention can be acetylated, acylated, or aminated, for example. Substituents which can be included on the peptide so as to modify it include, but are not limited to, H, alkyl, aryl, alkenyl, alkynyl, aromatic, ether, ester, unsubstituted or substituted amine, amide, halogen or unsubstituted or substituted sulfonyl or a 5 or 6 member aliphatic or aromatic ring. As used throughout this disclosure, the term "binding partner" can refer to a modified or unmodified peptide and a chemical or a peptidomimetic that structurally (three-dimensionally or two-dimensionally) resembles a modified or unmodified fMLP, V3 peptide, SAA, T20, and W peptide, and fragments or derivatives of these molecules. A "V3 peptide mimic" is a binding partner that resembles the V3 peptide and a "W peptide mimic" is a binding partner that resembles the W peptide. V3 peptide and W peptide mimics can be peptidomimetics, peptides, modified peptides, and derivatized peptides and thus, are members of the class of binding partners. Binding partners also include ligands for FPR class receptors identified by the methods of rational drug design detailed below.

The binding partners resembling fMLP, V3 peptide, SAA, T20, and W peptide, and fragments or derivatives of these molecules (e.g., V3 peptide mimics and W peptide mimics) not only include those molecules containing as a primary amino acid sequence all or part of the amino acid sequence of fMLP, V3 peptide, SAA, T20, and W peptide, and fragments or derivatives of these molecules found in nature but also altered sequences in which functionally equivalent amino acid residues are substituted for residues within the sequence resulting in a silent change. Accordingly, one or more amino acid residues within the sequence of fMLP, V3 peptide, SAA, T20, and W peptide, and fragments or derivatives of these molecules can be substituted by another amino acid of a similar polarity that acts as a functional equivalent, resulting in a silent alteration. Substitutes for an amino acid within the sequence can be selected from other members of the class to which the amino acid belongs. For example, the non-polar (hydrophobic) amino acids include alanine, leucine, isoleucine, valine, proline, phenylalanine, tryptophan, and methionine. The uncharged polar neutral amino acids include glycine, serine, threonine, cysteine, tyrosine, asparagine and glutamine. The positively charged (basic) amino acids include arginine, lysine, and histidine. The negatively charged (acidic) amino acids include aspartic acid and glutamic acid. The aromatic aminoacids include phenylalanine, tryptophan, and tyrosine. In other aspects of the invention, fMLP, V3 peptide, SAA, T20, and W peptide, and fragments or derivatives of these molecules, which are differentially modified during or after translation, e.g., by phosphorylation, glycosylation, cross-linking, acylation, proteolytic cleavage, linkage to an antibody molecule, membrane molecule, or other ligand, are contemplated. (Ferguson et al., Ann. Rev. Biochem. 57:285–320 (1988)).

In addition to the naturally occuring binding partners for FPR class receptors or fragments thereof, embodiments of the invention can use derivative or modified molecules that produce a more desirable cellular response. For example, a derivative binding partner can include a polypeptide that has been engineered to have one or more cystine residues incorporated into the protein so as to promote the formation of a more stable derivative through disulfide bond formation. (See e.g., U.S. Pat. No. 4,908,773). In the past, investigators have employed computers and computer graphics programs to aid in assessing the appropriateness of potential cystine linkage sites. (Perry, L. J., & Wetzel, R., *Science*, 226:555–557 (1984); Pabo, C. O., et al., *Biochemistry*, 25:5987–5991 (1986); Bott, R., et al., European Patent Application Ser. No. 130,756; Perry, L. J., & Wetzel, R., *Biochemistry*, 25:733–739 (1986); Wetzel, R. B., European Patent Application Ser. No. 155,832). The introduction of a cystine residue in a polypeptide can be accomplished using conventional molecular biology.

Additional binding partner derivatives include peptidomimetics that resemble a polypeptide of interest. The naturally occurring amino acids employed in the biological production of peptides all have the L-configuration. Synthetic peptides can be prepared employing conventional synthetic methods, utilizing L-amino acids, D-amino acids, or various combinations of amino acids of the two different configurations. Synthetic compounds that mimic the conformation and desirable features of a particular peptide, e.g., an oligopeptide, once such peptide has been found, but that avoids the undesirable features, e.g., flexibility (loss of conformation) and bond breakdown are known as a "peptidomimetics". (See, e.g., Spatola, A. F. Chemistry and Biochemistry of Amino Acids. Peptides, and Proteins (Weistein, B, Ed.), Vol. 7, pp. 267–357, Marcel Dekker, New York (1983), which describes the use of the methylenethio bioisostere [$CH_2 S$] as an amide replacement in enkephalin analogues; and Szelke et al., In peptides: Structure and Function, Proceedings of the Eighth American Peptide Symposium, (Hruby and Rich, Eds.); pp. 579–582, Pierce Chemical Co., Rockford, Ill. (1983), which describes renin inhibitors having both the methyleneamino [$CH_2NH$] and hydroxyethylene [$CHOHCH_2$] bioisosteres at the Leu-Val amide bond in the 6–13 octapeptide derived from angiotensinogen).

In general, the design and synthesis of a peptidomimetic involves starting with the sequence of the peptide and the conformation data (e.g., geometry data, such as bond lengths and angles) of a desired peptide (e.g., the most probable simulated peptide), and using such data to determine the geometries that should be designed into the peptidomimetic. Numerous methods and techniques are known in the art for performing this step, any of which could be used. (See, e.g., Farmer, P. S., Drug Design, (Ariens, E. J. ed.), Vol. 10, pp. 119–143 (Academic Press, New York, London, Toronto, Sydney and San Francisco) (1980); Farmer, et al., in TIPS, 9/82, pp. 362–365; Verber et al., in TINS, 9/85, pp. 392–396; Kaltenbronn et al., in J. Med. Chem. 33: 838–845 (1990); and Spatola, A. F., in Chemistry and Biochemistry of Amino Acids. Peptides, and Proteins, Vol. 7, pp. 267–357, Chapter 5, "Peptide Backbone Modifications: A Structure-Activity Analysis of Peptides Containing Amide Bond Surrogates. Conformational Constraints, and Relations" (B. Weisten, ed.; Marcell Dekker: New York, pub.) (1983); Kemp, D. S., "Peptidomimetics and the Template Approach to Nucleation of .beta.-sheets and alpha.-helices in Peptides," Tibech, Vol. 8, pp. 249–255 (1990). Additional teachings can be found in U.S. Pat. Nos. 5,288,707; 5,552,534; 5,811,515; 5,817,626; 5,817,879; 5,821,231; and 5,874,529. In the discussion that follows, several methods of molecular modeling and rational drug design are described. These techniques can be applied to identify additional ligands that resemble fMLP, V3 peptide, SAA, T20, and W peptide, and fragments or derivatives of these molecules. Further, these techniques can be applied to identify binding partners that do not resemble fMLP, V3 peptide, SAA, T20, and W peptide, and fragments or derivatives of these molecules but induce a host immune response to a pathogen and/or inhibit HIV infection.

Methods of Rational Drug Design

Rational drug design involving polypeptides requires identifying and defining a first peptide with which the designed drug is to interact, and using the first target peptide to define the requirements for a second peptide. With such requirements defined, one can find or prepare an appropriate peptide or non-peptide ligand that meets all or substantially all of the defined requirements. Thus, one goal of rational drug design is to produce structural or functional analogs of biologically active polypeptides of interest or of small molecules with which they interact (e.g., agonists, antagonists, null compounds) in order to fashion drugs that are, for example, more or less potent forms of the ligand. (See, e.g., Hodgson, *Bio. Technology* 9:19–21 (1991)). An example of rational drug design is the development of HIV protease inhibitors. (Erickson et al., *Science* 249:527–533 (1990)). Combinatorial chemistry is the science of synthesizing and testing compounds for bioactivity en masse, instead of one by one, the aim being to discover drugs and materials more quickly and inexpensively than was formerly possible. Rational drug design and combinatorial chemistry have become more intimately related in recent years due to the development of approaches in computer-aided protein modeling and drug discovery. (See e.g., U.S. Pat. Nos. 4,908,773; 5,884,230; 5,873,052; 5,331,573; and 5,888,738).

The use of molecular modeling as a tool for rational drug design and combinatorial chemistry has dramatically increased due to the advent of computer graphics. Not only is it possible to view molecules on computer screens in three dimensions but it is also possible to examine the interactions of ligands with various macromolecules such as enzymes and receptors and rationally design derivative molecules to test. (See Boorman, *Chem. Eng. News* 70:18–26 (1992). A vast amount of user-friendly software and hardware is now available and virtually all pharmaceutical companies have computer modeling groups devoted to rational drug design. Molecular Simulations Inc. (www.msi.com), for example, sells several sophisticated programs that allow a user to start from an amino acid sequence, build a two or three-dimensional model of the protein or polypeptide, compare it to other two and three-dimensional models, and analyze the interactions of compounds, drugs, and peptides with a three dimensional model in real time. Accordingly, in some embodiments of the invention, software is used to compare regions of fMLP, V3 peptide, SAA, T20, and W peptide, and fragments or derivatives of these molecules, as well as, FPR class receptors and fragments and derivatives of these receptors with other molecules, such as peptides, peptidomimetics, and chemicals, so that therapeutic interactions of new binding partners can be predicted and designed. (Schneider, *Genetic Engineering News* December: page 20 (1998), Tempczyk et al., *Molecular Simulations Inc. Solutions* April (1997) and Butenhof, *Molecular Simulations Inc. Case Notes* (August 1998)).

As a starting point to rational drug design, a two or three dimensional model of a polypeptide of interest is created (e.g., fMLP, V3 peptide, SAA, T20, and W peptide, or a fragment or derivative of these molecules or an FPR class receptor or a fragment or derivative of these receptors). In the past, the three-dimensional structure of proteins has been determined in a number of ways. Perhaps the best known way of determining protein structure involves the use of x-ray crystallography. A general review of this technique can be found in Van Holde, K. E. Physical Biochemistry, Prentice-Hall, N.J. pp. 221–239 (1971). Using this technique, it is possible to elucidate three-dimensional structure with good precision. Additionally, protein structure can be determined through the use of techniques of neutron diffraction, or by nuclear magnetic resonance (NMR). (See, e.g., Moore, W. J., Physical Chemistry, 4$^{th}$ Edition, Prentice-Hall, N.J. (1972)).

Alternatively, protein models of a polypeptide of interest can be constructed using computer-based protein modeling techniques. By one approach, the protein folding problem is solved by finding target sequences that are most compatible with profiles representing the structural environments of the residues in known three-dimensional protein structures. (See, e.g., U.S. Pat. No. 5,436,850). In another technique, the known three-dimensional structures of proteins in a given family are superimposed to define the structurally conserved regions in that family. This protein modeling technique also uses the known three-dimensional structure of a homologous protein to approximate the structure of a polypeptide of interest. (See e.g., U.S. Pat. Nos. 5,557,535; 5,884,230; and 5,873,052). Conventional homology modeling techniques have been used routinely to build models of proteases and antibodies. (Sowdhamini et al., *Protein Engineering* 10:207, 215 (1997)). Comparative approaches can also be used to develop three-dimensional protein models when the protein of interest has poor sequence identity to template proteins. In some cases, proteins fold into similar three-dimensional structures despite having very weak sequence identities. For example, the three-dimensional structures of a number of helical cytokines fold in similar three-dimensional topology in spite of weak sequence homology.

The recent development of threading methods and "fuzzy" approaches now enables the identification of likely folding patterns and functional protein domains in a number of situations where the structural relatedness between target and template(s) is not detectable at the sequence level. By one method, fold recognition is performed using Multiple Sequence Threading (MST) and structural equivalences are deduced from the threading output using the distance geometry program DRAGON that constructs a low resolution model. A full-atom representation is then constructed using a molecular modeling package such as QUANTA.

According to this 3-step approach, candidate templates are first identified by using the novel fold recognition algorithm MST, which is capable of performing simultaneous threading of multiple aligned sequences onto one or more 3-D structures. In a second step, the structural equivalences obtained from the MST output are converted into interresidue distance restraints and fed into the distance geometry program DRAGON, together with auxiliary information obtained from secondary structure predictions. The program combines the restraints in an unbiased manner and rapidly generates a large number of low resolution model confirmations. In a third step, these low resolution model confirmations are converted into full-atom models and subjected to energy minimization using the molecular modeling package QUANTA. (See e.g., Aszódi et al., Proteins: Structure, Function, and Genetics, Supplement 1:38–42 (1997)).

In a preferred approach, the commercially available "Insight II 98" program (Molecular Simulations Inc.) and accompanying modules are used to create a two and/or three dimensional model of a polypeptide of interest from an amino acid sequence. Insight II is a three-dimensional graphics program that can interface with several modules that perform numerous structural analysis and enable real-time rational drug design and combinatorial chemistry. Modules such as Builder, Biopolymer, Consensus, and Converter, for example, allow one to rapidly create a two dimensional or three dimensional model of a polypeptide, carbohydrate, nucleic acid, chemical or combinations of the foregoing from their sequence or structure. The modeling tools associated with Insight II support many different data file formats including Brookhaven and Cambridge databases; AMPAC/MOPAC and QCPE programs; Molecular Design Limited Molfile and SD files, Sybel Mol2 files, VRML, and Pict files.

Additionally, the techniques described above can be supplemented with techniques in molecular biology to design models of the protein of interest. For example, a polypeptide of interest can be analyzed by an alanine scan (Wells, Methods in Enzymol. 202:390–411 (1991)) or other types of site-directed mutagenesis analysis. In alanine scan, each amino acid residue of the polypeptide of interest is sequentially replaced by alanine in a step-wise fashion (i.e., only one alanine point mutation is incorporated per molecule starting at position #1 and proceeding through the entire molecule), and the effect of the mutation on the peptide's activity in a binding partner characterization assay is determined. Each of the amino acid residues of the peptide is analyzed in this manner and the regions important for assembly of the ligand/FPR class receptor complex are identified. These functionally important regions can be recorded on a computer readable medium, stored in a database in a computer system, and a search program can be employed to generate a protein model of the functionally important regions.

Once a model of the polypeptide of interest is created, it can be compared to other models so as to identify new binding partners ("candidate binding partners") that can effect assembly of the ligand/FPR class receptor complex. By starting with the amino acid sequence or protein model, for example, molecules having two-dimensional and/or three-dimensional homology to a known binding partner can be rapidly identified. In one approach, a percent sequence identity can be determined by standard methods that are commonly used to compare the similarity and position of the amino acid of two polypeptides. Using a computer program such as BLAST or FASTA, two polypeptides can be aligned for optimal matching of their respective amino acids (either along the full length of one or both sequences, or along a predetermined portion of one or both sequences). Such programs provide "default" opening penalty and a "default" gap penalty, and a scoring matrix such as PAM 250 (a standard scoring matrix; see Dayhoff et al., in: Atlas of Protein Sequence and Structure, Vol. 5, Supp. 3 (1978)) can be used in conjunction with the computer program. The percent identity can then be calculated as:

$$\frac{\text{total number of identical matches}}{\left[\begin{array}{c}\text{length of the longer sequence within the matched span} + \\ \text{number of gaps introduced into the longer sequence in order to} \\ \text{align the two sequences}\end{array}\right]} \times 100$$

Accordingly, the protein sequence corresponding to fMLP, V3 peptide, SAA, T20, and W peptide, or a fragment or derivative of these molecules can be compared to known sequences on a protein basis. Protein sequences corresponding to fMLP, V3 peptide, SAA, T20, and W peptide, or a fragment or derivative of these molecules are compared, for example, to known amino acid sequences found in Swissprot release 35, PIR release 53 and Genpept release 108 public databases using BLASTP with the parameter W=8 and allowing a maximum of 10 matches. In addition, the protein sequences encoding these binding partners are compared to publicly known amino acid sequences of Swissprot using BLASTX with the parameter E=0.001. The candidate ligands desirably have at least 50% homology and preferably have 60% or 70% or 80% or 90% or greater homology to fMLP, V3 peptide, SAA, T20, or W peptide. The candidatebinding partners can have the following degrees of homology to fMLP, V3 peptide, SAA, T20, or W peptide, for example: 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, and 99%. The candidate bind partners having greater than or equal to 50% homology are identified and are subsequently examined using a binding partner characterization assay. Binding partners that can activate an FPR class receptor and thereby, induce a host immune response to a pathogen and/or induce a phosphorylation of CCR5 and inhibition of HIV infection can then be identified.

In another embodiment, computer modeling and the sequence-to-structure-to-function paradigm is exploited to identify more binding partners that induce a host immune response to a pathogen and/or induce a phosphorylation of CCR5 and inhibition of HIV infection. By this approach, first the structure of a binding partner having a known response in a binding partner characterization assay is determined from its sequence using a threading algorithm, which aligns the sequence to the best matching structure in a structural database. Next, the protein's active site (i.e., the site important for a desired response in the characterization assay) is identified and a "fuzzy functional form" (FFF)—a three-dimensional descriptor of the active site of a protein—is created. (See e.g., Fetrow et al., *J. Mol. Biol.* 282:703–711 (1998) and Fetrow and Skolnick, *J. Mol. Biol.* 281: 949–968 (1998).

The FFFs are built by iteratively superimposing the protein geometries from a series of functionally related proteins with known structures. The FFFs are not overly specific, however, and the degree to which the descriptors can be relaxed is explored. In essence, conserved and functionally important residues for a desired response are identified and a set of geometric and conformational constraints for a specific function are defined in the form of a computer algorithm. The program then searches experimentally determined protein structures from a protein structural database for sets of residues that satisfy the specified constraints. In this manner, homologous three-dimensional structures can be compared and degrees (e.g., percentages of three-dimensional homology) can be ascertained. The ability to search three-dimensional structure databases for structural similarity to a protein of interest can also be accomplished by employing the Insight II using modules such as Biopolymer, Binding Site Analysis, and Profiles-3D.

By using this computational protocol, genome sequence data bases such as maintained by various organizations including: www.tigr.org/tdb; www.genetics.wisc.edu; www.stanford.edu/~ball; hiv-web.lanl.gov; www.ncbi.nlm-.nih.gov; www.ebi.ac.uk; pasteur.fr/other/biology; and www.genome.wi.mit.edu, can be rapidly screened for specific protein active sites and for identification of the residues at those active sites which resemble a desired molecule. Several other groups have developed databases of short sequence patterns or motifs designed to identify a given function or activity of a protein. These databases, notably Prosite (expasy.hcuge.ch/sprot/prosite.html); Blocks (www.blocks.fhcrc.org); and Prints (www.biochem.ucl.ac.uk/bsm/dbbrowser/PRINTS/PRINTS.html), the Molecular Modelling Database (MMDB), and the Protein Data Bank can use short stretches of sequence information to identify sequence patterns that are specific for a given function; thus they avoid the problems arising from the necessity of matching entire sequences. In this manner, new binding partners are rationally selected for further identification by binding partner characterization assays, as described above. Rounds or cycles of functional assays on the molecules and derivatives thereof and further FFF refinement and database searching allows an investigator to more narrowly define classes of binding partners that produce a desired level of induction of a host immune response to a pathogen and/or phosphorylation of CCR5 and inhibition of HIV infection.

By a similar approach, a binding partner that interacts with an FPR class receptor can be identified and manufactured as follows. First, a molecular model of one or more known binding partners or portions of these molecules that interact with an FPR class receptor are created using one of the techniques discussed above or as known in the art. Next, chemical libraries and databases are searched for molecules similar in structure to the known binding partner. That is, a search can be made of a three dimensional data base for non-peptide (organic) structures (e.g., non-peptide analogs, and/or dipeptide analogs) having three dimensional similarity to the known structure of the target compound. See, e.g., the Cambridge Crystal Structure Data Base, Crystallographic Data Center, Lensfield Road, Cambridge, CB2 1EW, England; and Allen, F. H., et al., Acta Crystallogr., B35: 2331–2339 (1979).

It is noted that search algorithms for three dimensional data base comparisons are available in the literature. See, e.g., Cooper, et al., J. Comput.-Aided Mol. Design, 3: 253–259 (1989) and references cited therein; Brent, et al., J. Comput.-Aided Mol. Design, 2: 311–310 (1988) and references cited therein. Commercial software for such searches is also available from vendors such as Day Light Information Systems, Inc., Irvine, Calif. 92714, and Molecular Design Limited, 2132 Faralton Drive, San Leandro, Calif. 94577. The searching is done in a systematic fashion by simulating or synthesizing analogs having a substitute moiety at every residue level. Preferably, care is taken that replacement of portions of the backbone does not disturb the tertiary structure and that the side chain substitutions are compatible to retain the receptor substrate interactions.

By another approach, protein models of FPR class receptors can be made by the methods described above and these models can be used to predict the interaction of binding partners. Having identified fMLP, V3 peptide, SAA, T20, and W peptide as binding partners for FPR class receptors, the active sites or regions of the receptor can be identified. Such active sites might typically be ligand binding sites. The active site can be identified using methods known in the art including, for example, from the amino acid sequences of peptides, from the nucleotide sequences of nucleic acids, or from study of complexes of the FPR class receptor with a ligand, such as fMLP, V3 peptide, SAA, T20, or W peptide. In the latter case, chemical or X-ray crystallographic methods can be used to find the active site by finding where on the receptor the complexed ligand is found. Next, the three dimensional geometric structure of the active site is determined. This can be done by known methods, including X-ray crystallography, which can determine a complete molecular structure. On the other hand, solid or liquid phase NMR can be used to determine certain intra-molecular distances. Any other experimental method of structure determination can be used to obtain partial or complete geometric structures. The geometric structures can be measured with a complexed ligand, natural or artificial, which may increase the accuracy of the active site structure determined.

If an incomplete or insufficiently accurate structure is determined, the methods of computer based numerical modelling can be used to complete the structure or improve its accuracy. Any recognized modelling method may be used, including parameterized models specific to particular biopolymers such as proteins or nucleic acids, molecular dynamics models based on computing molecular motions, statistical mechanics models based on thermal ensembles, or combined models. For most types of models, standard molecular force fields, representing the forces between constituent atoms and groups, are necessary, and can be selected from force fields known in physical chemistry. The incomplete or less accurate experimental structures can serve as constraints on the complete and more accurate structures computed by these modeling methods.

Finally, having determined the structure of the active site of the FPR class receptor, either experimentally, by modeling, or by a combination, candidate binding partners can be identified by searching databases containing compounds along with information on their molecular structure. Such a search seeks compounds having structures that match the determined active site structure and that interact with the groups defining the active site. Such a search can be manual, but is preferably computer assisted. One program that allows for such analysis is Insight II having the Ludi module. Further, the Ludi/ACD module allows a user access to over 65,000 commercially available drug candidates (MDL's Available Chemicals Directory) and provides the ability to screen these compounds for interactions with the protein of interest.

Alternatively, these methods can be used to identify improved binding partners from an already known binding partner. The composition of the known binding partner can be modified and the structural effects of modification can be determined using the experimental and computer modelling methods described above applied to the new composition. The altered structure is then compared to the active site structure of the compound to determine if an improved fit or interaction results. In this manner systematic variations in composition, such as by varying side groups, can be quickly evaluated to obtain modified modulating compounds or ligands of improved specificity or activity. Further experimental and computer modeling methods useful to identify binding partners based upon identification of the active sites of FPR class receptors will be apparent to those of skill in the art.

A number of articles review computer modelling of drugs interactive with specific-proteins, such as Rotivinen, et al., 1988, Acta Pharmaceutical Fennica 97:159–166; Ripka, New Scientist 54–57 (Jun. 16, 1988); McKinaly and Rossmann, 1989, Annu. Rev. Pharmacol. Toxiciol. 29:111–122; Perry and Davies, OSAR: Quantitative Structure-Activity Relationships in Drug Design pp. 189–193 (Alan R. Liss, Inc. 1989); Lewis and Dean, 1989 Proc. R. Soc. Lond. 236:125–140 and 141–162; and, with respect to a model receptor for nucleic acid components, Askew, et al., 1989, J. Am. Chem. Soc. 111:1082–1090. Other computer programs that screen and graphically depict chemicals are available from companies such as BioDesign, Inc. (Pasadena, Calif.), Allelix, Inc. (Mississauga, Ontario, Canada), and Hypercube, Inc. (Cambridge, Ontario). Although these are primarily designed for application to drugs specific to particular proteins, they can be adapted to design of drugs specific to FPR class receptors.

Many more computer programs and databases can be used with embodiments of the invention to identify binding partners that induce a host immune response to a pathogen and/or inhibit HIV infection. The following list is intended not to limit the invention but to provide guidance to programs and databases that are useful with the approaches discussed above. The programs and databases that can be used include, but are not limited to: MacPattern (EMBL), DiscoveryBase (Molecular Applications Group), GeneMine (Molecular Applications Group), Look (Molecular Applications Group), MacLook (Molecular Applications Group), BLAST and BLAST2 (NCBI), BLASTN and BLASTX (Altschul et al, *J. Mol. Biol.* 215: 403 (1990), herein incorporated by reference), FASTA (Pearson and Lipman, *Proc. Natl. Acad. Sci. USA*, 85: 2444 (1988), herein incorporated by reference), Catalyst (Molecular Simulations Inc.), Catalyst/SHAPE (Molecular Simulations Inc.), Cerius$^2$.DBAccess (Molecular Simulations Inc.), HypoGen (Molecular Simulations Inc.), Insight II, (Molecular Simulations Inc.), Discover (Molecular Simulations Inc.), CHARMm (Molecular Simulations Inc.), Felix (Molecular Simulations Inc.), DelPhi, (Molecular Simulations Inc.), QuanteMM, (Molecular Simulations Inc.), Homology (Molecular Simulations Inc.), Modeler (Molecular Simulations Inc.), Modeller 4 (Sali and Blundell J. Mol. Biol. 234:217–241 (1997)), ISIS (Molecular Simulations Inc.), Quanta/Protein Design (Molecular Simulations Inc.), WebLab (Molecular Simulations Inc.), WebLab Diversity Explorer (Molecular Simulations Inc.), Gene Explorer (Molecular Simulations Inc.), SeqFold (Molecular Simulations Inc.), Biopendium (Inpharmatica), SBdBase (Structural Bioinformatics), the EMBL/Swissprotein database, the MDL Available Chemicals Directory database, the MDL Drug Data Report data base, the Comprehensive Medicinal Chemistry database, Derwents's World Drug Index database, and the BioByteMasterFile database. Many other programs and data bases would be apparent to one of skill in the art given the present disclosure.

Once candidate agents have been identified, desirably, they are analyzed in a binding partner characterization assay. Further cycles of modeling and binding partner characterization assays can be employed to more narrowly define the parameters needed in a binding partner. Each binding partner and its response in a binding partner characterization assay can be recorded on a computer readable media and a database or library of binding partners and respective responses in a binding partner characterization assay can be generated. These databases or libraries can be used by researchers to identify important differences between active and inactive molecules so that compound libraries are enriched for binding partners that have favorable characteristics. The section below describes several binding partner characterization assays that can be used to identify molecules that induce a host immune response to a pathogen and/or inhibit HIV infection.

Binding Partner Characterization Assays

The binding partners described above are preferably analyzed in binding partner characterization assays to determine their ability to induce a host immune response to a pathogen and/or inhibit HIV infection. As a starting point for many binding partner characterization assays, binding partners and/or FPR class receptors are disposed on a support so as to create multimeric agents. These multimeric agents are biotechnological tools that can be used in binding partner characterization assays and can also be components for pharmaceuticals. Alternatively, binding partner characterization assays can be conducted in a liquid phase, the reaction products separated from unreacted components, and ligand/receptor complexes detected; e.g., using an immobilized antibody specific for a binding partner or FPR class receptor.

While a natural monomeric compound (e.g., fMLP, W peptide, V3 peptide, T20, SAA, or fragments thereof) is sufficient to interact with an FPR class receptor, synthetic ligands or multimeric ligands (e.g., fMLP, W peptide, V3 peptide, T20, SAA, or fragments thereof appearing as multiple units disposed on a support) can have far greater ability to interact with cells expressing FPR class receptors. It should be noted that the term "multimeric" is meant to refer to the presence of more than one binding partner on a support, as distinguished from the term "multimerized" which refers to the presence of more than binding partner joined in tandem as a single discrete unit, which can also be joined to a support.

A multimeric agent (synthetic or natural) can be obtained by joining a binding partner to a macromolecular support. A "support" can also be termed a carrier, a resin or any macromolecular structure used to attach or immobilize a binding partner. Solid supports include, but are not limited to, the walls of wells of a reaction tray, test tubes, polystyrene beads, magnetic beads, nitrocellulose strips, membranes, microparticles such as latex particles, cell membranes, artificial cells and others. A support can also be fabricated by self-aggregation of binding partners. For example, heated proteins or hydrophobic proteins aggregate so as to create macromolecular structure that, for the purposes of this disclosure, is referred to as a support. Advantageously, this type of support is also a multimeric agent by the very nature of its creation.

The macromolecular support (e.g., a resin or bead) can also have a hydrophobic surface that interacts with a portion of the binding partner by hydrophobic non-covalent interaction. The hydrophobic surface of the support can be a polymer such as plastic or any other polymer in which hydrophobic groups have been linked such as polystyrene, polyethylene or polyvinyl. Alternatively, the binding partner can be covalently bound to carriers including proteins and oligo/polysaccharides (e.g. cellulose, starch, glycogen, chitosane or aminated sepharose). In these later embodiments, a reactive group on the binding partner, such as a hydroxy or an amino group, can be used to join to a reactive group on the carrier so as to create the covalent bond. The support can also have a charged surface that interacts with the binding partner. Additionally, the support can have other reactive groups which can be chemically activated so as to attach a binding partner. For example, cyanogen bromide activated matrices, epoxy activated matrices, thio and thiopropyl gels, nitrophenyl chloroformate and N-hydroxy succinimide chlorformate linkages, and oxirane acrylic supports are common in the art. (Sigma).

The support can also comprise an inorganic carrier such as silicon oxide material (e.g. silica gel, zeolite, diatomaceous earth or aminated glass) to which the binding partner is covalently linked through a hydroxy, carboxy or amino group and a reactive group on the carrier. Furthermore, in some embodiments, a liposome or lipid bilayer (natural or synthetic) is contemplated as a support and binding partners are attached to the membrane surface or are incorporated into the membrane by techniques in liposome engineering. By one approach, liposome multimeric supports comprise a binding partner that is exposed on the surface of the bilayer and a second domain which anchors the binding partner to the lipid bilayer. The anchor can be constructed of hydrophobic amino acid residues, resembling known transmembrane domains, or can comprise ceramides that are attached to the first domain by conventional techniques.

Carriers for use in the body, (i.e. for prophylactic or therapeutic applications) are desirably physiological, non-toxic and preferably, non-immunoresponsive. Suitable carriers for use in the body include poly-L-lysine, poly-D, L-alanine, liposomes, and Chromosorb® (Johns-Manville Products, Denver Colo.). Ligand conjugated Chromosorb® (Synsorb-Pk) has been tested in humans for the prevention of hemolytic-uremic syndrome and was reported as not presenting adverse reactions. (Armstrong et al. *J. Infectious Diseases* 171:1042–1045 (1995)). For some embodiments, a "naked" carrier (i.e., lacking an attached binding partner) that has the capacity to attach a binding partner in the body of a subject is administered. By this approach, a "prodrug-type" therapy is envisioned in which the naked carrier is administered separately from the binding partner and, once both are in the body of the subject, the carrier and the binding partner are assembled into a multimeric complex.

The insertion of linkers, such as linkers (e.g., "λ linkers" engineered to resemble the flexible regions of λ phage) of an appropriate length between the binding partner and the support are also contemplated so as to encourage greater flexibility of the binding partner and thereby overcome any steric hindrance that can be presented by the support. The determination of an appropriate length of linker that allows for an optimal cellular response or lack thereof, can be determined by screening the binding partner s with varying linkers in the assays detailed in the present disclosure.

A composite support comprising more than one type of binding partner is also envisioned. A "composite support" can be a carrier, a resin, or any macromolecular structure used to attach or immobilize two or more different binding partners that induce a host immune response to a pathogen and/or inhibit HIV infection. In some embodiments, a liposome or lipid bilayer (natural or synthetic) is contemplated for use in constructing a composite support and binding partners are attached to the membrane surface or are incorporated into the membrane using techniques in liposome engineering.

As above, the insertion of linkers, such as λ linkers, of an appropriate length between the binding partner and the support is also contemplated so as to encourage greater flexibility in the molecule and thereby overcome any steric hindrance that can occur. The determination of an appropriate length of linker that allows for an optimal cellular response or lack thereof, can be determined by screening the ligands with varying linkers in the assays detailed in the present disclosure.

In other embodiments of the invention, the multimeric and composite supports discussed above can have attached multimerized ligands so as to create a "multimerized-multimeric support" and a "multimerized-composite support", respectively. A multimerized ligand can, for example, be obtained by coupling two or more binding partners in tandem using conventional techniques in molecular biology. The multimerized form of the ligand can be advantageous for many applications because of the ability to obtain an agent with a better ability induce a host immune response to a pathogen and/or inhibit HIV infection. The incorporation of linkers or spacers, such as flexible λ linkers, between the individual domains that make-up the multimerized agent can also be advantageous for some embodiments. The insertion of λ linkers of an appropriate length between protein binding domains, for example, can encourage greater flexibility in the molecule and can overcome steric hindrance. Similarly, the insertion of linkers between the multimerized ligand and the support can encourage greater flexibility and limit steric hindrance presented by the support. The determination of an appropriate length of linker that allows for an optimal induction of a host immune response to a pathogen and/or inhibition of HIV infection, can be determined by screening the binding partners with varying linkers in the assays detailed in this disclosure.

In preferable embodiments, the various types of supports discussed above are created using fMLP, W peptide, V3 peptide, T20, SAA, or fragments, derivatives, or modifications thereof or a peptidomimetic that resembles these molecules. Additionally, preferred multimeric supports include supports having FPR or FPRL1. The multimeric supports, composite supports, multimerized-multimeric supports, or multimerized-composite supports having a binding partner are collectively referred to as "support-bound binding partners". The multimeric supports, composite supports, multimerized-multimeric supports, or multimerized-composite supports, having an FPR class receptor are referred to as "support-bound receptors".

The support-bound binding partners and support-bound receptors can be used as biotechnological tools in rational drug design and approaches in dynamic combinatorial chemistry. (See e.g., Angnew, Chem. Int. Ed., 37:2828 (1998)). For example, a target biomolecule, such as an FPR class receptor, is joined to a support and is bound by the candidate binding partners from the libraries generated by the rational drug design approaches described above or by candidate binding partners obtained from a random combinatorial chemistry library. The FPR class receptor-containing resin that is bound with one or more candidate binding partner is removed from the binding reaction, the binding partners are eluted from the support, and are then identified. Cycles of immobilized target binding assays are conducted, classes of binding partners that exhibit desired binding characteristics are identified, and this data is recorded on a computer readable media and is used to select additional binding partners that produce a desired response.

Additionally, binding partners identified by the approaches described above can be synthesized on solid support beads by split-and-pool synthesis, a multistage process for producing very large numbers of compounds, to facilitate testing. The support-bound binding partners can be screened in binding partner characterization assays or "free mixtures" are created by cleaving the binding partners from the support and these free mixtures are screened in the binding partner characterization assays. Compounds that produce desirable responses are identified, recorded on a computer readable media, and the process can be repeated to select optimal binding partners.

The association of a binding partner with the support-bound receptor can be measured using many techniques common to molecular biology. The binding partner or FPR class receptor, for example, can be detectably labeled (e.g., radioactivity, magnetism, or fluorescence), so that the ligand/receptor complex can be directly determined by detecting the signal. Alternatively, the association of a ligand/receptor complex can be determined indirectly by employing a detectably labeled antibody that has an epitope that corresponds to a region of the binding partner or receptor.

Molecules that interact with FPR class receptors and, thereby, induce a host immune response to a pathogen and/or inhibit HIV infection can also be identified and characterized by using other methods for detecting protein-protein interactions. Among the traditional methods that can be employed are co-immunoprecipitation, crosslinking and co-purification through gradients or chromatographic columns of cell lysates or proteins obtained from cell lysates and the FPR class receptor to identify proteins in the lysate that interact with the FPR class receptor. For these assays, the FPR class receptor can be a full length receptor or a fragment or derivative thereof. Once isolated, the binding partner can be identified and can, in turn, be used, in conjunction with techniques in rational drug design to identify candidate binding partners.

One method that detects protein-protein interactions in vivo, the two-hybrid system, is described in detail for illustration only and not by way of limitation. Other similar assays that can be can be adapted to identify binding partners include:

(1) the two-hybrid systems (Field & Song, *Nature* 340:245–246 (1989); Chien et al., *Proc. Natl. Acad. Sci. USA* 88:9578–9582 (1991); and Young KH, *Biol. Reprod.* 58:302–311 (1998), all references herein expressly incorporated by reference);

(2) reverse two-hybrid system (Leanna & Hannink, *Nucl. Acid Res.* 24:3341–3347 (1996), herein incorporated by reference);

(3) repressed transactivator system (Sadowski et al., U.S. Pat. No. 5,885,779), herein incorporated by reference);

(4) phage display (Lowman H B, *Annu. Rev. Biophys. Biomol. Struct.* 26:401–424 (1997), herein incorporated by reference); and (5) GST/HIS pull down assays, mutant operators (Granger et al., WO 98/01879) and the like (See also Mathis G., *Clin. Chem.* 41:139–147 (1995); Lam K. S. *Anticancer Drug Res.*, 12:145–167 (1997); and Phizicky et al., *Microbiol Rev.* 59:94–123 (1995), all references herein expressly incorporated by reference).

An adaptation of the system described by Chien et al., 1991, Proc. Natl. Acad. Sci. USA, 88:9578–9582, herein incorporated by reference), which is commercially available from Clontech (Palo Alto, Calif.) is as follows. Plasmids are constructed that encode two hybrid proteins: one plasmid consists of nucleotides encoding the DNA-binding domain of a transcription activator protein fused to a nucleotide sequence encoding an FPR class receptor or fragment thereof, and the other plasmid consists of nucleotides encoding the transcription activator protein's activation domain fused to a cDNA encoding an unknown protein which has been recombined into this plasmid as part of a cDNA library. The DNA-binding domain fusion plasmid and the cDNA library are transformed into a strain of the yeast *Saccharomyces cerevisiae* that contains a reporter gene (e.g., HBS or lacZ) whose regulatory region contains the transcription activator's binding site. Either hybrid protein alone cannot activate transcription of the reporter gene: the DNA-binding domain hybrid cannot because it does not provide activation function and the activation domain hybrid cannot because it cannot localize to the activator's binding sites. Interaction of the two hybrid proteins reconstitutes the functional activator protein and results in expression of the reporter gene, which is detected by an assay for the reporter gene product.

The two-hybrid system or related methodology may be used to screen activation domain libraries for proteins that interact with the "bait" gene product. By way of example, and not by way of limitation, FPR class receptors can be used as the bait gene product. Total genomic or cDNA sequences are fused to the DNA encoding an activation domain. This library and a plasmid encoding a hybrid of a bait gene encoding the FPR class receptor product fused to the DNA-binding domain are cotransformed into a yeast reporter strain, and the resulting transformants are screened for those that express the reporter gene. For example, and not by way of limitation, a bait gene sequence encoding an FPR class receptor can be cloned into a vector such that it is translationally fused to the DNA encoding the DNA-binding domain of the GAL4 protein. These colonies are purified and the library plasmids responsible for reporter gene expression are isolated. DNA sequencing is then used to identify the proteins encoded by the library plasmids.

A cDNA library of the cell line from which proteins that interact with bait FPR class receptor are to be detected can be made using methods routinely practiced in the art. According to the particular system described herein, for example, the cDNA fragments can be inserted into a vector such that they are translationally fused to the transcriptional activation domain of GAL4. This library can be co-transformed along with the bait FPR class receptor gene-GAL4 fusion plasmid into a yeast strain which contains a lacZ gene driven by a promoter which contains GAL4 activation sequence. A cDNA encoded protein, fused to GAL4 transcriptional activation domain, that interacts with bait FPR class receptor gene product will reconstitute an active GAL4 protein and thereby drive expression of the lacZ gene. Colonies that express lacZ can be detected and the cDNA can then be purified from these strains, and used to produce and isolate the binding partner bytechniques routinely practiced in the art.

By another approach, a binding partner that induces a host immune response to a pathogen and/or inhibit HIV infections can be identified by using a cell-based assay. Accordingly, cells that express CCR5 and CD4, either naturally or by expression of an exogeous construct, are transfected with a construct comprising a nucleic acid sequence encoding an FPR class receptor. Positive transfectants are brought in contact with labeled candidate binding partners obtained from the approaches in rational drug design described above or from a random library of compounds. Activation of the FPR class receptor can then be determined by monitoring $Ca^{+2}$ mobilization and migration of the cells. Further, the ability to inhibit HIV infection can be determined by monitoring the phosphorylation of CCR5, the downregulation of CCR5 at the cell surface or by monitoring the products of HIV infection, such as p24, cell lysis, or production of viral progeny. Additionally, the ability of a binding partner to inhibit HIV infection can be determined microscopically (e.g., observing the lack of syncitia formation in the presence of the binding partner.) Many other ways to determine if a binding partner inhibits HIV infection will be apparent to one of skill in light of this disclosure. In the discussion below, several embodiments of the invention that have therapeutic and/or prophylactic application are described.

Therapeutic and Prophylactic Applications

In the therapeutic and prophylactic embodiments, the binding partners identified as inducing a host immune response to a pathogen and/or inhibiting HIV infection are incorporated into a pharmaceutical product and are administered to a subject in need. The pharmaceuticals of the invention can be formulated with an adjuvant or can be free and desirable embodiments provide the binding partner in a support-bound form. Optionally, the binding partner can be provided in an aggregated form as created, for example, by heating. A novel class of binding partners that bind an FPR class receptor with high avidity and inhibit HIV infection but fail to induce a cellular response associated with induction of a host immune response to a pathogen are other embodiments. For example, BOC-fMLP is one such candidate binding partner. These pharmaceuticals can also be formulated in adjuvant or free and are provided in the form of a support-bound agent. As above, an aggregated form of this embodiment can be created by heating the proteins and can administered to subjects in need.

The ligands can be administered in the form of a support-bound agent or in a pro-drug form that interacts with a support so as to create a support-bound agent in the body of the subject. Further, the manufacture of pharmaceuticals or therapeutic agents that deliver the binding partner and/or a nucleic acid sequence encoding the binding partner by several routes is another aspect of the invention. For example, and not by way of limitation, the use of DNA, RNA, and viral vectors having sequence encoding the binding partner is contemplated. Nucleic acids encoding a desired binding partner can be administered alone or in combination with binding partners.

These pharmacologically active compounds can be processed in accordance with conventional methods of galenic pharmacy to produce medicinal agents for administration to subjects, e.g., mammals including humans. The active ingredients can be incorporated into a pharmaceutical product with and without modification. Further, the manufacture of pharmaceuticals or therapeutic agents that deliver the pharmacologically active compounds of this invention by several routes are aspects of the invention. For example, and not by way of limitation, DNA, RNA, and viral vectors having sequence encoding the binding partners are used with embodiments. Nucleic acids encoding binding partners can be administered alone or in combination with other active ingredients.

The compounds of this invention can be employed in admixture with conventional excipients, i.e., pharmaceutically acceptable organic or inorganic carrier substances suitable for parenteral, enteral (e.g., oral) or topical application that do not deleteriously react with the pharmacologically active ingredients of this invention. Suitable pharmaceutically acceptable carriers include, but are not limited to, water, salt solutions, alcohols, gum arabic, vegetable oils, benzyl alcohols, polyetylene glycols, gelatine, carbohydrates such as lactose, amylose or starch, magnesium stearate, talc, silicic acid, viscous paraffin, perfume oil, fatty acid monoglycerides and diglycerides, pentaerythritol fatty acid esters, hydroxy methylcellulose, polyvinyl pyrrolidone, etc. Many more suitable vehicles are described in *Remmington's Pharmaceutical Sciences*, 15th Edition, Easton: Mack Publishing Company, pages 1405–1412 and 1461–1487 (1975) and The National *Formulary XIV*, 14th Edition, Washington, American Pharmaceutical Association (1975), herein incorporated by reference. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like that do not deleteriously react with the active compounds.

The effective dose and method of administration of a particular pharmaceutical formulation can vary based on the individual patient and the type and stage of the disease, as well as other factors known to those of skill in the art. Therapeutic efficacy and toxicity of such compounds can be determined by standard pharmaceutical procedures in cell cultures or experimental animals, e.g., ED50 (the dose therapeutically effective in 50% of the population). The data obtained from cell culture assays and animal studies is used in formulating a range of dosage for human use. The dosage of such compounds lies preferably within a range of circulating concentrations that include the ED50 with no toxicity.

The dosage varies within this range depending upon type of binding partner, the dosage form employed, sensitivity of the patient, and the route of administration.

Normal dosage amounts may vary from approximately 1 to 100,000 micrograms, up to a total dose of about 10 grams, depending upon the route of administration. Desirable dosages include 250 µg, 500 µg, 1 mg, 50 mg, 100 mg, 150 mg, 200 mg, 250 mg, 300 mg, 350 mg, 400 mg, 450 mg, 500 mg, 550 mg, 600 mg, 650 mg, 700 mg, 750 mg, 800 mg, 850 mg, 900 mg, 1 g, 1.1 g, 1.2 g, 1.3 g, 1.4 g, 1.5 g, 1.6 g, 1.7 g, 1.8 g, 1.9 g, 2 g, 3 g, 4 g, 5, 6 g, 7 g, 8 g, 9 g, and 10 g. Additionally, the concentrations of the binding partners can be quite high in embodiments that administer the agents in a topical form. Molar concentrations of binding partners can be used with some embodiments. Desirable concentrations for topical administration and/or for coating medical equipment range from 100 µM to 800 mM. Preferable concentrations for these embodiments range from 500 µM to 500 mM. For example, preferred concentrations for use in topical applications and/or for coating medical equipment include 500 µM, 550 µM, 600 µM, 650 µM, 700 µM, 750 µM, 800 µM, 850 µM, 900 µM, 1 mM, 5 mM, 10 mM, 15 mM, 20 mM, 25 mM, 30 mM, 35 mM, 40 mM, 45 mM, 50 mM, 60 mM, 70 mM, 80 mM, 90 mM, 100 mM, 120 mM, 130 mM, 140 mM, 150 mM, 160 mM, 170 mM, 180 mM, 190 mM, 200 mM, 300 mM, 325 mM, 350 mM, 375 mM, 400 mM, 425 mM, 450 mM, 475 mM, and 500 mM.

In some embodiments, the dose of binding partner preferably produces a tissue or blood concentration or both from approximately 0.1 µM to 500 mM. Desirable doses produce a tissue or blood concentration or both of about 1 to 800 µM. Preferable doses produce a tissue or blood concentration of greater than about 10 µM to about 500 µM. Preferable doses are, for example, the amount of binding partner required to achieve a tissue or blood concentration or both of 10 µM, 15 µM, 20 µM, 25 µM, 30 µM, 35 µM, 40 µM, 45 µM, 50 µM, 55 µM, 60 µM, 65 µM, 70 µM, 75 µM, 80 µM, 85 µM, 90 µM, 95 µM, 100 µM, 110 µM, 120 µM, 130 µM, 140 µM, 145 µM, 150 µM, 160 µM, 170 µM, 180 µM, 190 µM, 200 µM, 220 µM, 240 µM, 250 µM, 260 µM, 280 µM, 300 µM, 320 µM, 340 µM, 360 µM, 380 µM, 400 µM, 420 µM, 440 µM, 460 µM, 480 µM, and 500 µM. Although doses that produce a tissue concentration of greater than 800 µM are not preferred, they can be used with some embodiments of the invention. A constant infusion of the binding partner can also be provided so as to maintain a stable concentration in the tissues as measured by blood levels.

The exact dosage is chosen by the individual physician in view of the patient to be treated. Dosage and administration are adjusted to provide sufficient levels of the active moiety or to maintain the desired effect. Additional factors that can be taken into account include the severity of the disease state of the patient, age, and weight of the patient; diet, time and frequency of administration, drug combination(s), reaction sensitivities, and tolerance/response to therapy. Short acting pharmaceutical compositions are administered daily whereas long acting pharmaceutical compositions are administered every 2, 3 to 4 days, every week, or once every two weeks. Depending on half-life and clearance rate of the particular formulation, the pharmaceutical compositions of the invention are administered once, twice, three, four, five, six, seven, eight, nine, ten or more times per day.

Routes of administration of the pharmaceuticals of the invention include, but are not limited to, transdermal, topical, parenteral, gastrointestinal, transbronchial, and transalveolar. Transdermal or topical administration is accomplished by application of a cream, rinse, gel, etc. capable of allowing the pharmacologically active compounds to penetrate the skin or mucosa. Parenteral routes of administration include, but are not limited to, electrical or direct injection such as direct injection into a central venous line, intravenous, intramuscular, intraperitoneal, intradermal, or subcutaneous injection. Gastrointestinal routes of administration include, but are not limited to, ingestion and rectal. Transbronchial and transalveolar routes of administration include, but are not limited to, inhalation, either via the mouth or intranasally.

Compositions having the pharmacologically active compounds of this invention that are suitable for transdermal or topical administration include, but are not limited to, pharmaceutically acceptable suspensions, oils, creams, and ointments applied directly to the skin or incorporated into a protective carrier such as a transdermal device ("transdermal patch"). Examples of suitable creams, ointments, etc. can be found, for instance, in the Physician's Desk Reference. Examples of suitable transdermal devices are described, for instance, in U.S. Pat. No. 4,818,540 issued Apr. 4, 1989 to Chinen, et al., herein incorporated by reference.

Compositions having the pharmacologically active compounds of this invention that are suitable for parenteral administration include, but are not limited to, pharmaceutically acceptable sterile isotonic solutions. Such solutions include, but are not limited to, saline and phosphate buffered saline for injection into a central venous line, intravenous, intramuscular, intraperitoneal, intradermal, or subcutaneous injection.

Compositions having the pharmacologically active compounds of this invention that are suitable for transbronchial and transalveolar administration include, but not limited to, various types of aerosols for inhalation. Devices suitable for transbronchial and transalveolar administration of these are also embodiments. Such devices include, but are not limited to, atomizers and vaporizers. Many forms of currently available atomizers and vaporizers can be readily adapted to deliver compositions having the pharmacologically active compounds of the invention.

Compositions having the pharmacologically active compounds of this invention that are suitable for gastrointestinal administration include, but not limited to, pharmaceutically acceptable powders, pills or liquids for ingestion and suppositories for rectal administration. Due to the ease of use, gastrointestinal administration, particularly oral, is a preferred embodiment. Once the pharmaceutical comprising the binding partner has been obtained, it can be administered to a subject in need to treat or prevent HIV infection.

Aspects of the invention also include a coating for medical equipment such as prosthetics, implants, and instruments. Coatings suitable for use in medical devices can be provided by a gel or powder containing the binding partners or by polymeric coating into which the binding partners are suspended. Suitable polymeric materials for coatings or devices are those that are physiologically acceptable and through which a therapeutically effective amount of the binding partner can diffuse. Suitable polymers include, but are not limited to, polyurethane, polymethacrylate, polyamide, polyester, polyethylene, polypropylene, polystyrene, polytetrafluoroethylene, polyvinyl-chloride, cellulose acetate, silicone elastomers, collagen, silk, etc. Such coatings are described, for instance, in U.S. Pat. No. 4,612,337, issued Sep. 16, 1986 to Fox et al. that is incorporated herein by reference in its entirety.

In several aspects of the invention, binding partners, in particular pharmaceuticals having binding partners, are provided to a subject in need of an agent that interacts with an FPR class receptor so as to induce a host immune response to a pathogen. In other embodiments, pharmaceuticals having binding partners are provided to subjects in need of an agent that inhibits HIV infection. Methods to formulate pharmaceuticals for the induction of a host immune response to a pathogen and/or the inhibition of HIV are embodiments of the invention.

One embodiment, for example, concerns a method of inducing a host immune response to a pathogen in a subject. Accordingly, a subject in need of an agent that interacts with an FPR class receptor and, thereby, induces a host immune response is identified and said subject is provided a therapeutically sufficient amount of V3 peptide or W peptide. Such subjects in need can include individuals afflicted with chronic pathogenic infection (e.g., chronic viral disease, bacterial disease, or fungal disease). These individuals can be identified by clinical or biochemical techniques.

Other embodiments involve methods to treat or prevent HIV infection. By one approach, a subject in need of an agent that inhibits HIV infection is identified and said subject is provided a therapeutically sufficient amount of a binding partner. Such subjects in need can include individuals at risk of contracting HIV infection or are already afflicted with HIV infection. These individuals can be identified by clinical or biochemical techniques. In the section below, several examples that detail the materials and methods that were used in many of the experiments are provided.

EXAMPLE 1 fMLP Experiments

CCR5 Phosphorylation

Monocytes were isolated by counter-flow elutriation from the peripheral blood of normal donors (NIH Clinical Center, Transfusion Medicine Department, Bethesda, Md.) and enriched for mononuclear cells by using counter-flow elutriation. The purity of the cell preparations was examined by morphology after cytospin, and was >90%. The cells were stimulated with different concentrations of chemokines for indicated time periods at 37° C. and lysed for 20 min on ice with periodic mixing in lysis buffer (1% Triton X-100, 20 mM, Tris-HCl pH 8.0, 137 mM NaCl, 15% glycerol, 5 mM EDTA) containing phosphatase and protease inhibitors (1 mM phenylmethylsulfonyl fluoride, 5 µg/ml aprotinin, 5 µg/ml leupeptin, 1 mM sodium orthovanadate, 1 mM EGTA). Cell lysates were precleared with 30 □l of washed Protein-A sepherose beads (Pharmacia Biotech. Piscataway, N.J.), 1 µg of polyclonal anti-phospho-serine antibody (Zymed Laboratory Inc. South San Francisco, Calif.) was added to 200 µg cell lysates diluted with 2×immunoprecipitation (IP) buffer (1×buffer contains 1%Triton X-100, 10 mM Tris-HCl pH 7.4, 137 mM NaCl, 1 mM EDTA, 1 mM EGTA, 0.2 mM sodium orthovanadate, 0.2 mM PMSF, 0.5% NP-40). The reaction mixture was incubated at 4° C. overnight under constant rocking. The immune complex was captured by adding 50 µl of washed Protein-A sepharose beads (25 µl packed beads) and incubation of the reaction mixture at 4° C. for additional 2 hours. The beads were spun down (10 seconds at 14,000 rpm), the pellets were washed 3 times with ice-cold IP buffer, resuspended in 30 µl of 2×Laemmli sample buffer (126 mM Tris-HCl, 20% Glycerol, 4% SDS, 0.005% bromophenol blue with or without addition of 1% 2-mercaptoethanol, Novex, San Diego, Calif.) and boiled for 5 min to elute the immune complex. After electrophoresis on 4–12% SDS-PAGE precast gel (Novex), the proteins were transferred to Immobilon P membranes (Millipore, Bedford, Mass.). The membranes were blocked in freshly prepared PBS containing 3% dry milk 2 h, then were incubated with 1 µg/ml of polyclonal anti-CCR5 antibody (Millenium Biotechnology, Ramona, Calif.) overnight at 4° C. followed by washing 3 times with PBS containing 0.05% Tween 20. The membranes were incubated with a horse radish-peroxidase conjugated goat anti-rabbit IgG (1:5000) (Sigma, St. Louis, Mo.) in PBS containing 3% dry milk for 1 hour at room temperature with agitation. After washing 3 times with PBS-0.05% Tween 20, the membranes were incubated with Super Signal Chemiluminescent Substrate Stable Peroxide Solution (Pierce, Rockford, Ill.) for 1 min, and exposed to BIOMAX-MR film (Eastman Kodak Company, Rochester, N.Y.).

Binding Assays

Binding assays were performed by preincubating duplicate samples of monocytes ($2\times10^6$) with $10^{-6}$ M of fMLP for 60 min at 37° C. for 1 h in a volume of 200 µl/sample of binding medium (RPMI 1640 with 1% BSA, 25 mM Hepes, and 0.05% NaN3). After washing, the cells were incubated with 0.2 ng of $^{125}$I-labeled MIP-1β (specific activity: 2200 Ci/mmole, Dupont NEN, Boston, Mass.) for 40 min at room temperature to measure total cell binding. The nonspecific binding was determined by parallel incubation of cells in the presence of 1,000-fold excess of unlabeled MIP-1β (Pepro Tech Inc. Rocky Hill, N.J.). After incubation, the cells were washed with DPBS and centrifuged through a 10% sucrose/DPBS cushion. The tips of tubes containing cell pellets were cut and the cell-associated radioactivity was determined in a gamma counter. The results were presented as counts per minute (cpm) on $2\times10^6$ monocyte and were representative of at least three experiments performed.

Chemotaxis Assays

Monocyte migration was assessed by a 48-well microchemotaxis chamber technique. 25 µl MIP-1β diluted in assay medium (RPMI 1640 with 1% BSA and 25 mM Hepes) was placed in the lower compartment of the chemotaxis chamber. 50 µl cell suspension ($1\times10^6$ cell/ml) was placed in the upper compartment of the chamber. The upper and lower compartments were separated by a polycarbonate filter (5 µm pore-size, Neuroprobe, Cabin John, Md.). The chamber was incubated at 37° C. for 90 min in humidified air with 5% CO2. At the end of the incubation, the filter was removed, fixed and stained with Diff-Quik (Harlew, Gibbstown, N.J.). The migrated cells in three high-powered fields (HPF) obtained in triplicates (400×) were counted by light microscopy after coding the samples. The results are expressed as the net mean (±SD) number of migrated cells in 3 HPF after subtraction of spontaneous migration. At least three experiments were performed with same results.

Calcium Mobilization

Calcium mobilization was measured by incubating monocytes ($2\times10^7$/ml) in loading medium (DMEM, 10% FCS) with 5 µM Fura-2 AM (Molecular Probes, Eugene, Oreg.) for 30 min at room temperature in the dark. The dye-loaded cells were washed 3 times and resuspended in saline buffer (138 mM NaCl, 6 mM KCl, 1 mM CaCl2, 10 mM Hepes pH 7.4, 5 mM glucose, 0.1% BSA). The cells were then transferred into quartz cuvettes ($2\times10^6$ cells in 2 ml) which were placed in a luminescence spectrometer (LS-50B, Perkin-Elmer, Beaconsfield, UK). Stimulants at different concentrations were added in a volume of 20 µl to each cuvette at the indicated time points. The ratio of fluorescence at 340 and 380 nm was calculated using a FL-WinLab program (Perkin Elmer). To examine the effect of fMLP, monocytes were preincubated with $10^{-6}$ M fMLP or with medium alone for 60 min at 37° C. The cells were thoroughly washed and then were stained with Fura-2 for the calcium mobilization desensitization. The results are representative of at least three experiments performed.

CCR5 Expression

The change of surface expression of CCR5 on monocytes was monitored by FACS analyses (courtesy of L. Finch, SAIC Frederick, National Cancer Institute Frederick Cancer Research and Development Center, Frederick, Md.). $1 \times 10^6$ of monocytes were pretreated with medium or $10^{-6}$ M fMLP (Sigma) for 60 min at 37° C. After incubation, the cells were washed and stained with a FITC-conjugated monoclonal anti-CCR5 antibody 2D7 (20 μl/test) (PharMingen, San Diego, Calif.) on ice for 60 min. For protein kinase C inhibitor treatment, cells suspended in binding medium were incubated with 1.4 ng/ml staurosporine (Sigma) for 30 min at 37° C. or 50 ng/ml of Calphostine C (Sigma) for 2.5 h at 37° C. with an 8-watt fluorescent light source, followed by incubation with fMLP and anti-CCR5 antibodies. The cells were then washed twice with DPBS containing 2% BSA and fixed with 1% Paraformaldehyde (Sigma). The fluorescence was measured by flow cytometer (Becton Dickinson, San Jose, Calif.). Results are presented as the percentage of cells stained with anti-CCR5 antibody.

HIV-1 Env Fusion and Viral Infection

HIV-1 env fusion assays were performed as previously described. (Nussbaum et al., *J Virol*, 68:5411 (1994)). Briefly, human osteosarcoma cells transfected to express CD4 and CCR5 (HOS/CCR5/CD4 cells, a kind gift from the NIH AIDS Research and Reference Reagents Program) were further transfected to co-express FPR, a high affinity receptor for the bacterial chemotactic peptide fMLP. Control cells were transfected with plasmic vector pcDNA3 alone (Mock/CCR5/CD4). HeLa cells (ATCC, Rockville, Md.) were first infected with a recombinant vaccinia viruse vBC43 expressing monocyte tropic HIV-1env (BAL 31) and vBC21R containing a T7 promoter linked to the LacZ reporter gene. HOS cells expressing CCR5/CD4 in the absence or presence of FPR were infected with recombinant vaccinia virus vTF7-3 encoding the bacteriophage T7 RNA polymerase under the control of the natural P7.5 early-late vaccinia promoter. After infection overnight at 31° C., $1 \times 10^5$ infected HeLa cells were mixed with $1 \times 10^5$ infected HOS cells and seeded in triplicates in the wells of 96-well tissue culture plates. Chemokines or fMLP were added simultaneously when two cell types were mixed. After incubation at 37° C. for 12 h, the cells were lysed with 0.05% Nonidet P-40 and spun at 2500 rpm for 5 min. 50 μl of cell lysate were mixed with 50 μl of 16 mM chlorophenol red-β-galactopyranoside (CPRG, Boerhinger Mannheim) dissolved in 2×phosphate buffer (0.12 M $Na_2HPO_4$, 0.08 M $NaH_2PO_4$, 0.02 M KCl, 0.002 M $MgSO_{4, 0.01}$ M β-mercaptoethanol). The reactions were kept at room temperature for 2–4 h before the color was measured with a ELISA reader for absorbance at 570 nm. The same procedure was used in assays with human monocytes. For studies of viral infection of macrophages, peripheral blood mononuclear cells were allowed to adhere to plastic for 2 h and the non-adherent cells were removed. The adherent cells were cultured in rhM-CSF (100 ng/ml) for 7 days to induce macrophage differentiation. The monocyte-derived macrophages were then treated with fMLP at the designated concentrations, and after 1 h, the treated cells were infected with $HIV_{JRFL}$ at a MOI of 1.0. 4 h after HIV-infection, the cells were washed with PBS and fresh medium was added. HIV p24 antigen levels were then measured on day 6 using an enzyme-linked immunosorbent assay. fMLP treatment did not affect the viability of macrophages as compared to cells treated with medium alone.

EXAMPLE 2

V3 Peptide Experiments

Reagents and cells

Synthetic V3 peptide (33 amino acid) of the HIV-1 gp120 (MN) (TRPNYNKRKRIHIGPGRAFYTTKNIIGTIRQAH-$NH_2$ (SEQ. ID. No. 3) was kindly provided by the NIH AIDS Research and Reference Reagents Program (Bethesda, Md.). This peptide was also synthesized on a preparative scale (0.25 mmol) by Fmoc chemistry on a 433A peptide synthesizer (PE Biosystem, Foster City, Calif.) (Proost et al., *Cytokine*, 7:97 (1995)) and purified by RP-HPLC on a Resource RPC column (Amersham Pharmacia Biotech, Uppsala, Sweden). The sequence of the synthetic peptide was confirmed by Edman degradation on a 477A/120A protein sequencer (PE Biosystems). Recombinant human chemokines and SAA were purchased from Pepro Tech Inc. (Rocky Hill, N.J.). The chemotactic peptide fMLP and horse radish peroxidase conjugated goat anti-rabbit IgG were purchased from Sigma (St. Louis, Mo.). Protein A Sepharose CL-4B beads were purchased from Pharmacia Biotech (Piscataway, N.J.). Polyclonal rabbit anti-phosphoserine antibody was from Zymed Laboratory Inc. (South San Francisco, Calif.). Polyclonal rabbit anti-CCR5 was from ProSci, Inc.(Poway, Calif.).

Human peripheral blood monocytes and neutrophils were separated from Buffy-Coats (NIH Clinical Center, Transfusion Medicine Department, Bethesda, Md.) as described previously. (Deng et al., *Blood*, 94:1165 (1999)). Rat basophilic leukemia cells (RBL-2H3) transfected with an epitope-tagged cDNA coding for the high affinity fMLP receptor, FPR (designated ETFR cells), were a kind gift of Drs. H. Ali and R. Snyderman (Duke University, Durham, N.C.). Human embryonic kidney epithelial 293 cells transfected with cDNA encoding FPRL1 (FPRL1/293 cells) were established as previously described. (Gao and Murphy, *J. Biol. Chem.*, 268:25395 (1993)).

Chemotaxis Assays

The migration of cells was assessed by a 48-well microchemotaxis chamber technique as described. (Su et al., *J. Exp. Med.*, 189:395 (1999)). Chemoattractants were placed in the wells of the lower compartment of the chemotaxis chamber. Cell suspension was placed in the wells of the upper compartment. Two compartments were separated by a polycarbonate filter (Neuroprobe, CabinJohn, Md., 5 μm pore-size for monocytes and neutrophils, 10 μm pore size for receptor transfectants). The filters used for migration of cell lines transfected with receptor genes were precoated with 50 μg/ml collagen type I (Collaborative Biomedical Products, Bedford, Mass.). The chamber was incubated at 37° C. in humidified air with 5% $CO_2$. After incubation (1 h for neutrophils, 1.5 h for monocytes and 5 h for receptor transfected cell lines), the filter was removed, fixed and stained with LeukoStat™ (Fisher Scientific, Pittsburg, Pa.). The migrated cells in three high-powered fields (400×) were counted by light microscopy after coding the samples. The results are expressed as the mean (±SE) value of the migration in triplicate samples and are representatives of at least three experiments performed. Cell migration was also presented as chemotaxis index (CI) representing the fold increase in cell migration induced by stimulants over control medium.

Calcium Mobilization

Calcium mobilization was measured by incubating $2 \times 10^7$/ml cells in loading medium (DMEM, 10% FBS) with 5 μM Fura-2 AM (Molecular Probes, Eugene, Oreg.) for 30 min at room temperature in the dark. The dye-loaded cells were washed 3 times with loading medium and resuspended in saline buffer [138 mM NaCl, 6 mM KCl, 1 mM CaCl$_2$, 10 mM HEPES (pH 7.4), 5 mM Glucose, 0.1% BSA] at a concentration of 1×10$^6$/ml. The cells were then transferred into quartz cuvettes (2 ml) which were placed in a luminescence spectrometer (LS-50B, Perkin-Elmer, Beaconsfield, England). Stimulants at different concentrations were added in a volume of 20 μl to each cuvette at the indicated time points. The ratio of fluorescence at 340 and 380 nm wavelength was calculated using a FL WinLab program (Perkin-Elmer).

Phosphorylation of CCR5

Monocytes stimulated with different concentrations of stimulants for indicated time periods at 37° C. were lysed for 20 min on ice with periodic mixing in lysis buffer [1% Triton X-100, 20 mM Tris-HCl (pH 8.0), 137 mM NaCl, 15% glycerol, 5 mM EDTA] containing phosphatase and protease inhibitors (1 mM phenylmethylsulfonyl fluoride, 5 μg/ml aprotinin, 5 μg/ml leupeptin, 1 mM sodium orthovanadate, 1 mM EGTA). Cell lysates were precleaned with 30 μl of washed Protein A Sepharose beads (15 μl packed beads) at 4° C. for 1 hour and 1 μg of polyclonal anti-phosphoserine antibody was added to 200 μg cell lysates diluted with 2×immunoprecipitation (IP) buffer [1×: 1% Triton X-100, 10 mM Tris-HCl (pH 7.4), 137 mM NaCl, 1 mM EDTA, 1 mM EGTA, 0.2 mM sodium, 0.2 mM PMSF, 0.5% NP-40]. The reaction mixture was incubated at 4° C. overnight under constant rocking. The immunecomplex was captured by adding 50 μl of washed Protein A sepharose beads (25 μl packed beads) and incubating the reaction mixture at 4° C. for an additional 2 hours. The beads were spun down (10 seconds at 14,000 rpm), drained off the supernatants, washed 3 times with ice-cold 1×IP buffer, then were resuspended in 30 μl 2×Laemmli sample buffer (126 mM Tris-HCl, 20% Glycerol, 4% SDS, 0.005% Bromophenol Blue. Novex, San Diego, Calif.) and boiled for 5 min to elute the immune complex. After electrophoresis on 10% SDS-PAGE precast gel (Novex, San Diego, Calif.), the proteins were transferred to Immobilon P membranes (Millipore Corp., Bedford, Mass.). The membrane was blocked in freshly prepared PBS containing 3% dry milk at 4° C. for 2 hours, then was incubated with 1 μg/ml of polyclonal anti-CCR5 antibody overnight at 4° C. followed by washing 3 times with PBS-T (0.05% Tween 20). The membrane was incubated with a horse radish peroxidase-conjugated goat anti-rabbit IgG at 1:5000 dilution in PBS containing 3% dry milk for 1 hour at room temperature with agitation. After washing 3 times with PBS-T, the membrane was incubated with SuperSignal Chemiluminescent Substrate Stable Peroxide Solution (PIERCE, Rockford, Ill.) for 1 min, and exposed to BIOMAX-MR film (Eastman Kodak Company, Rochester, N.Y.).

Statistical Analysis

All experiments were performed at least three times and the results presented are from representative experiments. The significance of the difference between test and control groups was analyzed using the Student's t test.

EXAMPLE 3

W Peptide Experiments

Chemicals

The WKYMVM (Trp-Lys-Tyr-Met-Val-D-Met, designated W peptide) (SEQ. ID. No. 1) was synthesized and purified by the Department of Biochemistry, Colorado State University (Fort Collins, Colo.), according to the published sequence. (Seo et al., *J. Immunol.*, 158:1895–1901 (1997)). The purity was greater than 90% and the amino acid composition was verified by mass-spectrometer. The endotoxin levels in the dissolved peptide were undetectable. The synthetic formyl peptide fMLP was purchased from Sigma (St. Louis, Mo.). Tritiated ($^3$H) fMLP was purchased from Dupont NEN (Boston, Mass.).

Cells

The human peripheral blood mononuclear cells (PBMC) were isolated from leukopacks through the courtesy of Transfusion Medicine Department, NIH Clinical Center, Bethesda, Md. Monocytes were further purified by elutriation to yield >90% pure preparations. Human neutrophils were purified from the same leukopacks by 3% dextran sedimentation with a purity of >98%. Rat basophilic leukemia cells stably transfected with Epitope tagged high affinity fMLP receptor FPR (designated ETFR cells) were a kind gift of Drs. H. Ali and R. Snyderman, Duke University, NC. The FPR-like receptor 1 (FPRL1) cDNA was cloned and stably transfected into human embryonic kidney cells (HEK) 293 (designated FPRL1/293 cells) as reported previously. (Gao and Murphy, *J. Biol. Chem.*, 268:25395–25401 (1993)). All of the transfected cells were maintained in DMEM, 10% FCS and 0.8 mg/ml geneticin (G418, GibcoBRL, Rockville, Md.).

Chemotaxis

Migration of leukocytes, ETFR, and FPRL1/293 cells was assessed using a 48-well microchemotaxis chamber technique as previously described. (Gong et al., *J. Biol. Chem.*, 273:4289–4292 (1998); Gong et al., *J. Biol. Chem.*, 272:11682–11685 (1997); Ben-Baruch et al., *J. Biol. Chem.*, 270:22123–22128 (1995)). Different concentrations of stimulants were placed in wells of the lower compartment of the chamber (Neuro Probe, Cabin John, Mass.), the cell suspension was seeded into wells of the upper compartment which was separated from the lower compartment by a polycarbonate filter (Osmonics, Livermore, Calif.; 5 μm-pore size for leukocytes, 10 μm pore-size for ETFR and FPRL1/293 cells). The filters for ETFR and FPRL1/293 cell migration were precoated with 50 μg/ml collagen type I (Collaborative Biomedical Products, Bedford, Mass.) to favor cell attachment. After incubation at 37° C. (90 min for monocytes, 60 min for neutrophils, and 300 min for ETFR or FPRL1/293 cells), the filters were removed, stained and the number of cells migrating across the filter were counted by light microscopy after coding the samples. The experiments were performed at least 5 times with each cell type and the results are presented as the chemotaxis indexes (CI) representing the fold increase in the number of migrating cells in response to stimuli, over the spontaneous cell migration (in response to control medium).

Calcium mobilization

Calcium mobilization was assayed by incubating 2×10$^7$/ml of monocytes, neutrophils, FPRL1 or FPR transfectants in loading buffer containing 138 mM NaCl, 6 mM KCl, 1 mM CaCl$_2$, 10 mM HEPES (pH 7.4), 5 mM glucose, 0.1% BSA with 5 μM Fura-2 (Sigma) at 37° C. for 30 min. The dye-loaded cells were washed and resuspended in fresh loading buffer. The cells were then transferred into quartz cuvettes (10$^6$ cells in 2 ml) which were placed in a luminescence spectrometer LS50 B (Perkin-Elmer Limited, Beaconsfield, England). Stimulants at different concentrations were added in a volume of 20 μl to the cuvettes at indicated time points. The ratio of fluorescence at 340 and 380 nm wavelength was calculated using the FL WinLab program (Perkin-Elmer).

Binding Assays

A single concentration of $^3$H-fMLP was added simultaneously with different concentrations of unlabeled fMLP or W peptide to a cell suspension (FPRL1/293 or ETFR, $2\times10^6$ cells/200 µl in RPMI 1640, 1% BSA and 0.05% NaN$_3$) in duplicate samples. The samples were incubated under constant rotation for 30 minutes at 37° C. After incubation, the samples were filtered onto Whatman GF/C discs (Whatman International Ltd., Kent, UK) on a 12-well manifold followed by extensive washing with ice-cold phosphate-buffered saline (PBS). The discs were air-dried at 65° C., submerged in liquid scintillation cocktail, and counted for β emision.

Statistical Analysis

Unless specified, all experiments were performed 3–5 times and the results presented are from representative experiments. The significance of the difference between test and control groups was analyzed with a Student's t test.

Although the invention has been described with reference to embodiments and examples, it should be understood that various modifications can be made without departing from the spirit of the invention. Accordingly, the invention is limited only by the following claims. All references cited herein are hereby expressly incorporated by reference.

What is claimed is:

1. A method of identifying a binding partner for a formyl peptide receptor (FPR) class receptor that desensitizes an HIV co-receptor comprising the steps of:
   providing a cell having a CCR5 or CXCR4 receptor and an FPR class receptor;
   contacting said cell with a candidate binding partner; and
   identifying the candidate binding partner as a binding partner if the candidate binding partner binds to an FPR class receptor and induces the phosphorylation of the CCR5 or CXCR4 receptor, wherein phosphorylation identifies desensitization.

2. A method of identifying a binding partner for a formyl peptide receptor (FPR) class receptor that desensitizes an HIV co-receptor comprising the steps of:
   providing a cell having a CCR5 or CXCR4 receptor and an FPR class receptor;
   contacting said cell with a candidate binding partner; and
   identifying the candidate binding partner as a binding partner if the candidate binding partner binds to an FPR class receptor and induces the downregulation of the CCR5 or CXCR4 receptor, at the cell surface, wherein downregulation identifies desensitization.

3. A method of identifying a binding partner for a formyl peptide receptor (FPR) class receptor that desensitizes an HIV co-receptor comprising the steps of:
   providing a cell having a CCR5 or CXCR4 receptor and an FPR class receptor;
   contacting said cell with a candidate binding partner; and
   identifying the candidate binding partner as a binding partner if the candidate binding partner binds to an FPR class receptor and inhibits HIV env-mediated fusion, wherein inhibition identifies desensitization.

4. A method of claim 1, further comprising
   incorporating the binding partner into a composition upon observation of the presence of phosphorylation of the HIV co-receptor.

5. A method of claim 2, further comprising
   incorporating the binding partner into a composition upon observation of the downregulation of the HIV co-receptor at the cell surface.

6. A method of claim 3, further comprising
   incorporating the binding partner into a composition upon observation of the inhibition of HIV env-mediated fusion.

7. A method of claims 1–3 or 4–6 wherein, in said step of providing a cell having a CCR5 or CXCR4 receptor, the receptor is a CCR5 receptor.

8. A method of claims 1–3 or 4–6 wherein said candidate binding partner is W peptide (SEQ ID NO:1).

9. A method of claims 1–3 or 4–6 wherein said candidate binding partner is V3 peptide (SEQ ID NO:3).

* * * * *

SEQUENCE LISTING

```
<160> NUMBER OF SEQ ID NOS: 4

<210> SEQ ID NO 1
<211> LENGTH: 6
<212> TYPE: PRT
<213> ORGANISM: Artificial Sequence
<220> FEATURE:
<221> NAME/KEY: VARIANT
<222> LOCATION: 6
<223> OTHER INFORMATION: Xaa=D-methionine
<220> FEATURE:
<223> OTHER INFORMATION: Artificial Peptide

<400> SEQUENCE: 1

Trp Lys Tyr Met Val Xaa
 1               5

<210> SEQ ID NO 2
<211> LENGTH: 5
<212> TYPE: PRT
<213> ORGANISM: Artificial Sequence
<220> FEATURE:
<223> OTHER INFORMATION: Artificial Peptide

<400> SEQUENCE: 2

Met Ile Leu Phe Phe
 1               5

<210> SEQ ID NO 3
<211> LENGTH: 33
<212> TYPE: PRT
<213> ORGANISM: Artificial Sequence
<220> FEATURE:
<223> OTHER INFORMATION: Artificial Peptide

<400> SEQUENCE: 3

Thr Arg Pro Asn Tyr Asn Lys Arg Lys Arg Ile His Ile Gly Pro Gly
 1               5                  10                  15

Arg Ala Phe Tyr Thr Thr Lys Asn Ile Ile Gly Thr Ile Arg Gln Ala
                20                  25                  30

His

<210> SEQ ID NO 4
<211> LENGTH: 6
<212> TYPE: PRT
<213> ORGANISM: Artificial Sequence
<220> FEATURE:
<223> OTHER INFORMATION: Artificial Peptide
```

```
<400> SEQUENCE: 4

Trp Lys Tyr Met Tyr Met
 1               5
```